US008123719B2

(12) United States Patent
Edwards et al.

(10) Patent No.: US 8,123,719 B2
(45) Date of Patent: Feb. 28, 2012

(54) DEVICES, SYSTEMS AND METHODS FOR MEDICAMENT DELIVERY

(75) Inventors: Eric Shawn Edwards, Midlothian, VA (US); Evan Thomas Edwards, Fredericksburg, VA (US); Mark J. Licata, Doswell, VA (US); Paul F. Meyers, Fishers, IN (US)

(73) Assignee: Intelliject, Inc., Richmond, VA (US)

( * ) Notice: Subject to any disclaimer, the term of this patent is extended or adjusted under 35 U.S.C. 154(b) by 1371 days.

(21) Appl. No.: 11/692,359

(22) Filed: Mar. 28, 2007

(65) Prior Publication Data
US 2008/0103490 A1 May 1, 2008

Related U.S. Application Data

(60) Provisional application No. 60/787,046, filed on Mar. 29, 2006.

(51) Int. Cl.
*A61M 37/00* (2006.01)
(52) U.S. Cl. ............... 604/82; 604/89; 604/92; 604/518
(58) Field of Classification Search .............. 604/82, 604/84, 89–92, 518
See application file for complete search history.

(56) References Cited

U.S. PATENT DOCUMENTS

| 2,960,087 A | 11/1960 | Uytenbogaart |
| 3,055,362 A | 9/1962 | Uytenbogaart |
| 3,115,133 A | 12/1963 | Morando |
| 3,426,448 A | 2/1969 | Sarnoff |
| 3,688,765 A | 9/1972 | Gasaway |
| 3,768,472 A | 10/1973 | Hodosh et al. |
| 3,795,061 A | 3/1974 | Sarnoff et al. |
| 3,945,379 A | 3/1976 | Pritz et al. |
| 4,108,177 A | 8/1978 | Pistor |
| 4,226,235 A | 10/1980 | Sarnoff et al. |
| 4,360,019 A | 11/1982 | Portner et al. |
| 4,424,057 A | 1/1984 | House |
| 4,441,629 A | 4/1984 | Mackal |
| 4,484,910 A | 11/1984 | Sarnoff |
| 4,573,976 A | 3/1986 | Sampson et al. |
| 4,596,556 A | 6/1986 | Morrow et al. |
| 4,610,666 A | 9/1986 | Pizzino |

(Continued)

FOREIGN PATENT DOCUMENTS

EP 1 712 178 A2 10/2006

(Continued)

OTHER PUBLICATIONS

Examination Report for New Zealand Patent Application No. NZ 589864, mailed Dec. 14, 2010.

(Continued)

*Primary Examiner* — Kevin C Sirmons
*Assistant Examiner* — Emily Schmidt
(74) *Attorney, Agent, or Firm* — Cooley LLP

(57) ABSTRACT

An apparatus includes a housing, a medicament container disposed within the housing, a first energy storage member and second energy storage member. The medicament container includes a first plunger disposed within a proximal end portion of the medicament container and a second plunger disposed within the medicament container spaced apart from the first plunger. The first energy storage member is configured to produce a force when actuated to move at least the second plunger within the medicament container. The second energy storage member is configured to produce a force when actuated to move the first plunger and the second plunger within the medicament container. The second energy storage member is different than the first energy storage member.

30 Claims, 29 Drawing Sheets

U.S. PATENT DOCUMENTS

| | | | |
|---|---|---|---|
| 4,617,557 A | 10/1986 | Gordon | |
| 4,624,660 A | 11/1986 | Mijers et al. | |
| 4,640,686 A | 2/1987 | Dalling et al. | |
| 4,643,721 A | 2/1987 | Brunet | |
| 4,666,430 A | 5/1987 | Brown et al. | |
| 4,673,657 A | 6/1987 | Christian | |
| 4,689,042 A | 8/1987 | Sarnoff et al. | |
| 4,693,708 A | 9/1987 | Wanderer et al. | |
| 4,755,169 A * | 7/1988 | Sarnoff et al. | 604/511 |
| 4,781,697 A | 11/1988 | Slaughter | |
| 4,782,841 A | 11/1988 | Lopez | |
| 4,784,652 A | 11/1988 | Wikström | |
| 4,795,433 A | 1/1989 | Sarnoff | |
| 4,853,521 A | 8/1989 | Claeys et al. | |
| 4,874,381 A | 10/1989 | Vetter | |
| 4,874,382 A | 10/1989 | Lindemann et al. | |
| 4,894,054 A | 1/1990 | Miskinyar | |
| 4,906,235 A | 3/1990 | Roberts | |
| 4,915,695 A | 4/1990 | Koobs | |
| 4,941,880 A | 7/1990 | Burns | |
| 4,959,056 A | 9/1990 | Dombrowski et al. | |
| 4,968,302 A | 11/1990 | Schluter et al. | |
| 4,983,164 A | 1/1991 | Hook et al. | |
| 5,000,736 A | 3/1991 | Kaufhold, Jr. et al. | |
| 5,024,656 A | 6/1991 | Gasaway et al. | |
| 5,037,306 A | 8/1991 | van Schoonhoven | |
| 5,038,023 A | 8/1991 | Saliga | |
| 5,041,088 A | 8/1991 | Ritson et al. | |
| 5,062,603 A | 11/1991 | Smith et al. | |
| 5,064,413 A | 11/1991 | McKinnon et al. | |
| 5,071,353 A | 12/1991 | van der Wal | |
| 5,080,649 A | 1/1992 | Vetter | |
| 5,085,642 A | 2/1992 | Sarnoff et al. | |
| 5,092,843 A | 3/1992 | Monroe et al. | |
| 5,125,898 A | 6/1992 | Kaufhold, Jr. et al. | |
| 5,139,490 A | 8/1992 | Vetter et al. | |
| 5,167,641 A | 12/1992 | Schmitz | |
| 5,199,949 A | 4/1993 | Haber et al. | |
| 5,224,936 A | 7/1993 | Gallagher | |
| 5,240,146 A | 8/1993 | Smedley et al. | |
| 5,281,198 A | 1/1994 | Haber et al. | |
| 5,286,258 A | 2/1994 | Haber et al. | |
| 5,298,023 A | 3/1994 | Haber et al. | |
| 5,312,326 A | 5/1994 | Myers et al. | |
| 5,314,412 A | 5/1994 | Rex | |
| 5,343,519 A | 8/1994 | Feldman | |
| 5,344,407 A | 9/1994 | Ryan | |
| 5,354,284 A | 10/1994 | Haber et al. | |
| 5,356,376 A | 10/1994 | Milijasevic et al. | |
| 5,363,842 A | 11/1994 | Mishelevich et al. | |
| 5,380,281 A | 1/1995 | Tomellini et al. | |
| 5,383,851 A | 1/1995 | McKinnon, Jr. et al. | |
| 5,399,163 A | 3/1995 | Peterson et al. | |
| 5,417,660 A | 5/1995 | Martin | |
| 5,466,217 A | 11/1995 | Myers et al. | |
| 5,514,135 A | 5/1996 | Earle | |
| 5,558,679 A | 9/1996 | Tuttle | |
| 5,567,160 A | 10/1996 | Massino | |
| 5,568,555 A | 10/1996 | Shamir | |
| 5,569,192 A | 10/1996 | van der Wal | |
| 5,584,815 A | 12/1996 | Pawelka et al. | |
| 5,615,771 A | 4/1997 | Hollister | |
| 5,616,132 A | 4/1997 | Newman | |
| 5,645,534 A | 7/1997 | Chanoch | |
| 5,681,291 A | 10/1997 | Galli | |
| 5,695,476 A | 12/1997 | Harris | |
| 5,697,916 A | 12/1997 | Schraga | |
| 5,716,338 A | 2/1998 | Hjertman et al. | |
| 5,743,886 A | 4/1998 | Lynn et al. | |
| 5,772,635 A | 6/1998 | Dastur et al. | |
| 5,792,190 A | 8/1998 | Olson et al. | |
| 5,800,397 A | 9/1998 | Wilson et al. | |
| 5,805,423 A | 9/1998 | Wever et al. | |
| 5,809,997 A | 9/1998 | Wolf | |
| 5,813,397 A | 9/1998 | Goodman et al. | |
| 5,814,020 A | 9/1998 | Gross | |
| 5,832,488 A | 11/1998 | Eberhardt | |
| 5,837,546 A | 11/1998 | Allen et al. | |
| RE35,986 E | 12/1998 | Ritson et al. | |
| 5,846,089 A | 12/1998 | Weiss et al. | |
| 5,848,988 A | 12/1998 | Davis | |
| 5,852,590 A | 12/1998 | de la Huerga | |
| 5,853,292 A | 12/1998 | Eggert et al. | |
| 5,868,713 A | 2/1999 | Klippenstein | |
| 5,868,721 A | 2/1999 | Marinacci | |
| D407,487 S | 3/1999 | Greubel et al. | |
| 5,925,021 A | 7/1999 | Castellano et al. | |
| 5,928,195 A | 7/1999 | Malamud | |
| 5,941,857 A | 8/1999 | Nguyen et al. | |
| 5,964,739 A | 10/1999 | Champ | |
| 5,970,457 A | 10/1999 | Brant et al. | |
| 5,971,953 A | 10/1999 | Bachynsky | |
| 6,015,438 A | 1/2000 | Shaw | |
| 6,039,713 A | 3/2000 | Botich et al. | |
| 6,045,534 A | 4/2000 | Jacobsen et al. | |
| 6,062,901 A | 5/2000 | Liu et al. | |
| 6,063,053 A | 5/2000 | Castellano et al. | |
| 6,074,213 A | 6/2000 | Hon | |
| 6,077,106 A | 6/2000 | Mish | |
| 6,084,526 A | 7/2000 | Blotky et al. | |
| 6,086,562 A | 7/2000 | Jacobsen et al. | |
| 6,096,002 A | 8/2000 | Landau | |
| 6,099,504 A | 8/2000 | Gross et al. | |
| 6,102,896 A | 8/2000 | Roser | |
| 6,119,684 A | 9/2000 | Nöhl et al. | |
| 6,149,626 A | 11/2000 | Rachynsky et al. | |
| 6,158,613 A | 12/2000 | Novosel et al. | |
| 6,161,281 A | 12/2000 | Dando et al. | |
| 6,165,155 A | 12/2000 | Jacobsen et al. | |
| 6,175,752 B1 | 1/2001 | Say | |
| 6,179,812 B1 | 1/2001 | Botich et al. | |
| 6,192,891 B1 | 2/2001 | Gravel et al. | |
| 6,193,695 B1 | 2/2001 | Rippstein, Jr. | |
| 6,202,642 B1 | 3/2001 | McKinnon et al. | |
| 6,210,359 B1 | 4/2001 | Patel et al. | |
| 6,210,369 B1 | 4/2001 | Wilmot et al. | |
| 6,219,587 B1 | 4/2001 | Ahlin et al. | |
| 6,221,045 B1 | 4/2001 | Duchon et al. | |
| 6,221,055 B1 | 4/2001 | Shaw et al. | |
| 6,245,046 B1 | 6/2001 | Sibbitt | |
| 6,258,063 B1 | 7/2001 | Haar et al. | |
| 6,259,654 B1 | 7/2001 | de la Huerga | |
| 6,264,629 B1 | 7/2001 | Landau | |
| 6,270,455 B1 | 8/2001 | Brown | |
| 6,312,412 B1 | 11/2001 | Saied et al. | |
| 6,317,630 B1 | 11/2001 | Gross et al. | |
| 6,334,070 B1 | 12/2001 | Nova et al. | |
| 6,364,866 B1 | 4/2002 | Furr et al. | |
| 6,371,939 B2 | 4/2002 | Bergens et al. | |
| 6,387,078 B1 | 5/2002 | Gillespie, III | |
| 6,398,760 B1 | 6/2002 | Danby | |
| 6,405,912 B2 | 6/2002 | Giannou | |
| 6,406,455 B1 | 6/2002 | Willis et al. | |
| 6,411,567 B1 | 6/2002 | Niemiec et al. | |
| 6,413,236 B1 | 7/2002 | Van Dyke | |
| 6,419,656 B1 | 7/2002 | Vetter et al. | |
| 6,425,897 B2 | 7/2002 | Overes et al. | |
| 6,428,517 B1 | 8/2002 | Hochman et al. | |
| 6,428,528 B2 | 8/2002 | Sadowski | |
| 6,475,181 B1 | 11/2002 | Potter et al. | |
| 6,478,769 B1 | 11/2002 | Parker | |
| 6,478,771 B1 | 11/2002 | Lavi et al. | |
| 6,494,863 B1 | 12/2002 | Shaw et al. | |
| 6,500,150 B1 | 12/2002 | Gross et al. | |
| 6,514,230 B1 | 2/2003 | Munk et al. | |
| 6,529,446 B1 | 3/2003 | de la Huerga | |
| 6,530,900 B1 | 3/2003 | Dailey et al. | |
| 6,530,904 B1 | 3/2003 | Edwards et al. | |
| 6,535,714 B2 | 3/2003 | Melker et al. | |
| 6,540,672 B1 | 4/2003 | Simonsen et al. | |
| 6,540,675 B2 | 4/2003 | Aceti et al. | |
| 6,544,233 B1 | 4/2003 | Fukui et al. | |
| 6,544,234 B1 | 4/2003 | Gabriel | |
| 6,551,276 B1 | 4/2003 | Mann et al. | |
| 6,551,298 B1 | 4/2003 | Zhang | |
| 6,554,798 B1 | 4/2003 | Mann et al. | |
| 6,558,320 B1 | 5/2003 | Causey, III et al. | |

| | | |
|---|---|---|
| 6,560,471 B1 | 5/2003 | Heller |
| 6,565,533 B1 | 5/2003 | Smith et al. |
| 6,569,123 B2 | 5/2003 | Alchas |
| 6,572,584 B1 | 6/2003 | Shaw et al. |
| 6,574,166 B2 | 6/2003 | Niemiec |
| 6,575,939 B1 | 6/2003 | Brunel |
| RE38,189 E | 7/2003 | Walker et al. |
| 6,585,685 B2 | 7/2003 | Staylor et al. |
| 6,585,698 B1 | 7/2003 | Packman et al. |
| 6,589,158 B2 | 7/2003 | Winkler |
| 6,595,956 B1 | 7/2003 | Gross et al. |
| 6,616,627 B2 | 9/2003 | Willis et al. |
| 6,633,796 B1 | 10/2003 | Pool et al. |
| 6,641,566 B2 | 11/2003 | Douglas et al. |
| 6,645,181 B1 | 11/2003 | Lavi et al. |
| 6,648,850 B2 | 11/2003 | Landau |
| 6,676,630 B2 | 1/2004 | Landau et al. |
| 6,689,093 B2 | 2/2004 | Landau |
| 6,702,778 B2 | 3/2004 | Hill et al. |
| 6,707,763 B2 | 3/2004 | Osberg et al. |
| 6,708,050 B2 | 3/2004 | Carim |
| 6,722,916 B2 | 4/2004 | Buccinna et al. |
| 6,723,077 B2 | 4/2004 | Pickup et al. |
| 6,726,661 B2 | 4/2004 | Munk et al. |
| 6,736,796 B2 | 5/2004 | Shekalim |
| 6,743,635 B2 | 6/2004 | Neel et al. |
| 6,749,437 B2 | 6/2004 | Chan |
| 6,752,781 B2 | 6/2004 | Landau et al. |
| 6,767,336 B1 | 7/2004 | Kaplan |
| 6,770,052 B2 | 8/2004 | Hill et al. |
| 6,783,509 B1 | 8/2004 | Landau et al. |
| 6,786,875 B2 | 9/2004 | Barker et al. |
| 6,786,885 B2 | 9/2004 | Hochman et al. |
| 6,793,646 B2 | 9/2004 | Giambattista et al. |
| 6,803,856 B1 | 10/2004 | Murphy et al. |
| 6,808,514 B2 | 10/2004 | Schneider et al. |
| 6,809,653 B1 | 10/2004 | Mann et al. |
| 6,817,986 B2 | 11/2004 | Slate et al. |
| 6,817,987 B2 | 11/2004 | Vetter et al. |
| 6,830,560 B1 | 12/2004 | Gross et al. |
| 6,839,304 B2 | 1/2005 | Niemiec et al. |
| 6,872,200 B2 | 3/2005 | Mann et al. |
| 6,875,195 B2 | 4/2005 | Choi |
| 6,883,222 B2 | 4/2005 | Landau |
| 6,923,764 B2 | 8/2005 | Aceti et al. |
| 6,936,029 B2 | 8/2005 | Mann et al. |
| 6,937,150 B2 | 8/2005 | Medema et al. |
| 6,942,646 B2 | 9/2005 | Langley et al. |
| 6,946,299 B2 | 9/2005 | Neel et al. |
| 6,949,082 B2 | 9/2005 | Langley et al. |
| 6,952,604 B2 | 10/2005 | DeNuzzio et al. |
| 6,953,445 B2 | 10/2005 | Wilmot et al. |
| 6,953,693 B2 | 10/2005 | Neel et al. |
| 6,958,691 B1 | 10/2005 | Anderson et al. |
| 6,959,247 B2 | 10/2005 | Neel et al. |
| 6,961,285 B2 | 11/2005 | Niemiec et al. |
| 6,964,650 B2 | 11/2005 | Alexandre et al. |
| 6,969,259 B2 | 11/2005 | Pastrick et al. |
| 6,979,316 B1 | 12/2005 | Rubin et al. |
| 6,979,326 B2 | 12/2005 | Mann et al. |
| 6,985,870 B2 | 1/2006 | Martucci et al. |
| 6,997,911 B2 | 2/2006 | Klitmose |
| 7,014,470 B2 | 3/2006 | Vann |
| 7,077,835 B2 | 7/2006 | Robinson et al. |
| 7,113,101 B2 | 9/2006 | Petersen et al. |
| 7,116,233 B2 | 10/2006 | Zhurin |
| 7,126,879 B2 | 10/2006 | Snyder |
| 7,158,011 B2 | 1/2007 | Brue |
| 7,191,916 B2 | 3/2007 | Clifford et al. |
| 7,229,458 B2 | 6/2007 | Boecker et al. |
| 7,278,983 B2 | 10/2007 | Ireland et al. |
| 7,299,981 B2 | 11/2007 | Hickle et al. |
| 7,351,223 B2 | 4/2008 | Call |
| 7,678,073 B2 | 3/2010 | Griffiths et al. |
| 7,708,719 B2 | 5/2010 | Wilmot et al. |
| 2001/0005781 A1 | 6/2001 | Bergens et al. |
| 2002/0074345 A1 | 6/2002 | Schneider et al. |
| 2002/0076679 A1 | 6/2002 | Aman |
| 2002/0090601 A1 | 7/2002 | Strupat et al. |
| 2003/0028145 A1 | 2/2003 | Duchon et al. |
| 2003/0040717 A1 | 2/2003 | Saulenas et al. |
| 2003/0100862 A1 | 5/2003 | Edwards et al. |
| 2003/0105430 A1 | 6/2003 | Lavi et al. |
| 2003/0106824 A1 | 6/2003 | Wilmot et al. |
| 2003/0135388 A1 | 7/2003 | Martucci et al. |
| 2003/0233070 A1 | 12/2003 | De La Serna et al. |
| 2004/0015125 A1 | 1/2004 | Alexandre et al. |
| 2004/0019326 A1 | 1/2004 | Gilbert et al. |
| 2004/0039336 A1 | 2/2004 | Amark et al. |
| 2004/0039337 A1 | 2/2004 | Letzing |
| 2004/0039368 A1 | 2/2004 | Reilly et al. |
| 2004/0054327 A1 | 3/2004 | Gillespie, III |
| 2004/0116854 A1 | 6/2004 | Abulhaj et al. |
| 2004/0138611 A1 | 7/2004 | Griffiths et al. |
| 2004/0143298 A1 | 7/2004 | Nova et al. |
| 2004/0159364 A1 | 8/2004 | Landau et al. |
| 2004/0220524 A1 | 11/2004 | Sadowski et al. |
| 2004/0249358 A1 | 12/2004 | McWethy et al. |
| 2004/0267204 A1 | 12/2004 | Brustowicz |
| 2005/0033234 A1 | 2/2005 | Sadowski et al. |
| 2005/0033386 A1 | 2/2005 | Osborn et al. |
| 2005/0062603 A1 | 3/2005 | Fuerst et al. |
| 2005/0090781 A1 | 4/2005 | Baba et al. |
| 2005/0096588 A1 | 5/2005 | Hagmann et al. |
| 2005/0134433 A1 | 6/2005 | Sweeney, II |
| 2005/0137530 A1 | 6/2005 | Campbell et al. |
| 2005/0148931 A1 | 7/2005 | Juhasz |
| 2005/0148945 A1 | 7/2005 | Chen |
| 2005/0159705 A1 | 7/2005 | Crawford et al. |
| 2005/0165360 A1 | 7/2005 | Stamp |
| 2005/0168337 A1 | 8/2005 | Mahoney |
| 2005/0171477 A1 | 8/2005 | Rubin et al. |
| 2005/0182358 A1 | 8/2005 | Veit et al. |
| 2005/0186221 A1 | 8/2005 | Reynolds et al. |
| 2005/0197654 A1 | 9/2005 | Edman et al. |
| 2005/0261742 A1 | 11/2005 | Nova et al. |
| 2005/0267403 A1 | 12/2005 | Landau et al. |
| 2005/0277891 A1 | 12/2005 | Sibbitt |
| 2006/0030819 A1 | 2/2006 | Young et al. |
| 2006/0053036 A1 | 3/2006 | Coffman et al. |
| 2006/0058848 A1 | 3/2006 | Piraino et al. |
| 2006/0111666 A1 | 5/2006 | Hommann et al. |
| 2006/0111671 A1 | 5/2006 | Klippenstein |
| 2006/0129090 A1 | 6/2006 | Moberg et al. |
| 2006/0189938 A1 | 8/2006 | Hommann et al. |
| 2006/0200077 A1 | 9/2006 | Righi et al. |
| 2006/0247579 A1 | 11/2006 | Friedman |
| 2006/0265186 A1 | 11/2006 | Holland et al. |
| 2007/0008113 A1 | 1/2007 | Spoonhower et al. |
| 2007/0074722 A1 | 4/2007 | Giroux et al. |
| 2007/0088268 A1 | 4/2007 | Edwards et al. |
| 2007/0129708 A1 | 6/2007 | Edwards et al. |
| 2007/0149925 A1 | 6/2007 | Edwards et al. |
| 2007/0184847 A1 | 8/2007 | Hansen et al. |
| 2007/0203247 A1 | 8/2007 | Phillips et al. |
| 2007/0210147 A1 | 9/2007 | Morrone et al. |
| 2007/0213598 A1 | 9/2007 | Howard et al. |
| 2007/0239114 A1 | 10/2007 | Edwards et al. |
| 2008/0033393 A1 | 2/2008 | Edwards et al. |
| 2008/0058719 A1 | 3/2008 | Edwards et al. |
| 2008/0059133 A1 | 3/2008 | Edwards et al. |
| 2008/0160492 A1 | 7/2008 | Campbell et al. |
| 2008/0249468 A1 | 10/2008 | Edwards et al. |
| 2008/0269689 A1 | 10/2008 | Edwards et al. |
| 2009/0024112 A1 | 1/2009 | Edwards et al. |
| 2010/0022963 A1 | 1/2010 | Edwards et al. |
| 2010/0211005 A1 | 8/2010 | Edwards et al. |

FOREIGN PATENT DOCUMENTS

| | | |
|---|---|---|
| JP | 51-021295 | 2/1976 |
| JP | 54-22316 | 2/1979 |
| MX | PA04009276 | 1/2005 |
| WO | WO 86/06967 | 12/1986 |
| WO | WO 91/04760 A1 | 4/1991 |
| WO | WO93/02720 | 2/1993 |
| WO | WO 94/06487 | 3/1994 |
| WO | WO 95/26009 | 9/1995 |
| WO | WO 95/35126 | 12/1995 |

| | | |
|---|---|---|
| WO | WO 01/24690 A2 | 4/2001 |
| WO | WO 01/26020 A1 | 4/2001 |
| WO | WO 01/88828 | 11/2001 |
| WO | WO 01/93926 A2 | 12/2001 |
| WO | WO 03/095001 A1 | 11/2003 |
| WO | WO 03/097133 A1 | 11/2003 |
| WO | WO 2004/054644 | 7/2004 |
| WO | WO 2005/050526 A2 | 6/2005 |
| WO | WO 2006/045525 A1 | 5/2006 |
| WO | WO 2006/109778 A1 | 10/2006 |

OTHER PUBLICATIONS

Search and Examination Report for British Patent Application No. 1105021.8, mailed May 18, 2011.
U.S. Appl. No. 11/566,422, Edwards et al.
U.S. Appl. No. 11/758,393, Edwards et al.
U.S. Appl. No. 11/572,148, Edwards et al.
U.S. Appl. No. 11/621,236, Edwards et al.
U.S. Appl. No. 11/692,359, Edwards et al.
U.S. Appl. No. 11/671,025, Edwards et al.
U.S. Appl. No. 11/679,331, Edwards et al.
Heartsine Technology, samaritan™ Pad Accessories [online] [retrieved on Jun. 1, 2007] Retrieved from the Internet <URL: http://www.heartsine.com/aboutsam-accessories.htm>.
CliniSense Corporation, "Drug delivery devices A potentially harsh environment for drugs," Stability [online] [retrieved on Jun. 1, 2007] Retrieved from the Internet <URL: http://www.clinisense.com/devices.htm>.
CliniSense Corporation, "LifeTrack Technology A new method to detect improper storage." Stability [online] [retrieved on Jun. 1, 2007] Retrieved from the Internet <URL: http://www.clinisense.com/tech.htm>.
AED Professionals™ Brochure [online] [retrieved on Jun. 1, 2007] Retrieved from the Internet <URL: http://www.aedprofessionals.com/>.
Daniel Ruppar, "Implant Technologies Expected to Remain a Niche but Effective Method of Drug Delivery," Drug Delivery Technology, Feb. 2007, vol. 7, No. 2 [online] [retrieved on Jun. 1, 2007] Retrieved from the Internet <URL: http://www.drugdeliverytech-online.com/drugdelivery/200702/templates/pageviewer_print?pg=44&pm=8 >.
"Solutions for Medical Devices," 3M Brochure, © 3M 2006 80-6201-3490-0.
Merle Tingelstad, "Revolutionary Medical Technology Increases Demand for Flexible Interconnects," [online] May 15, 2006 [retrieved on Nov. 15, 2006] Retrieved from the Internet <URL: http://www.ecnmag.com/index.asp?layout=articlePrint&ArticleID-CA6332947 >.
"Flexible circuits / Flex circuits / Flexible Technology Ltd.," Flexible Technology Limited [online] [retrieved on Aug. 28, 2006] Retrieved from the Internet <URL: http://www.flexibletechnology.com/>.
"Flexible circuits capabilities of Flexible Technology Limited," Our Flexible Circuits Capabilities [online] [retrieved on Aug. 28, 2006] Retrieved from the Internet <URL: http://www.flexibletechnology.com/Flexible_circuits_Capability.htm >.
"Flex Circuits/flexible circuits design guide," [online] [retrieved on Aug. 28, 2006] Retrieved from the Internet <URL: http://flexiblecircuit.co.uk/Flex_Circuits_Design_Guide.htm >.
"Insect Stings Auto-injector Pouches and Carry Cases," The Insect Stings On-Line Shop, [online] [retrieved on Jan. 24, 2007] Retrieved from the Internet <URL: http://www.insectstings.co.uk/acatalog/Auto_Injector_Pouches.html >.
"Anaphylaxis Canada Product Catalogue," Anaphylaxis Canada > Living with Anaphylaxis > Tools and Resources [online] [retrieved on Jan. 24, 2007] Retrieved from the Internet <URL: http://anaphylaxis.org/content/livingwith/productcatalogue.asp>.
"Microfluidics Device Provides Programmed, Long-Term Drug Dosing," nano techwire.com [online] [retrieved on Nov. 28, 2006] Retrieved from the Internet <URL: http://nanotechwire.com/news.asp?nid=3141&ntid=124&pg=1 >.
Roger Allan, "Medical Electronics: Technology Advances Will Revolutionize Healthcare," Sep. 30, 2002 [online] [retrieved on Nov. 28, 2006] Retrieved from the Internet <URL: http://www.elecdesign.com/Articles/Index.cfm?AD=I&ArticleID=2041>.
RFID Gazette, "Smart Labels in Healthcare," Sep. 29, 2005 [online] [retrieved on Nov. 28, 2006] Retrieved from the Internet <URL: http://www.rfidagazeete.org/2005/09/smart_labels_in.html >.
"Merck Serono Launches easypod(R), First Electronic Growth Hormone Injection Device," Jan. 30, 2007 [online] [retrieved on Feb. 5, 2007] Retrieved from the Internet <URL: http://www.biz.yahoo.com/prnews/070130/ukm028.html?.v=8.
Dr. Oliver Scholz, "Drug depot in a tooth," [online] [retrieved on Feb. 6, 2007] Retrieved from the Internet <URL: http://www.fraunhofer.de/fhg/EN/press/pi/2007/02Mediendienst22007Thema2.jsp?print=true.
International Search Report and Written Opinion for International Patent Application No. PCT/US06/03415 mailed Jul. 13, 2006, 10 pages.
Combined Search and Examination Report for British Patent Application No. GB 08713202.0, mailed Dec. 1, 2008.
Office Action for Japanese Patent Application No. JP2007-553358, mailed Feb. 24, 2010.
Search Report and Written Opinion for International Patent Application No. PCT/US07/007626 mailed Sep. 29, 2008.
Search Report for European Patent Application No. EP 06 71 9987, mailed Oct. 30, 2008.

\* cited by examiner

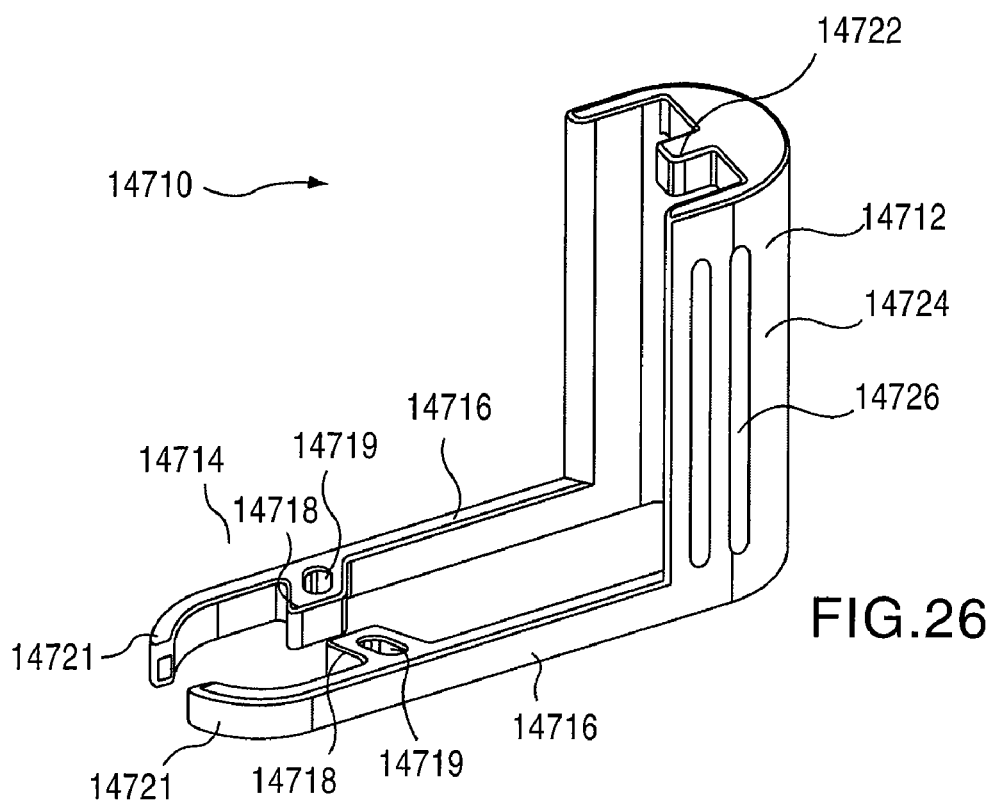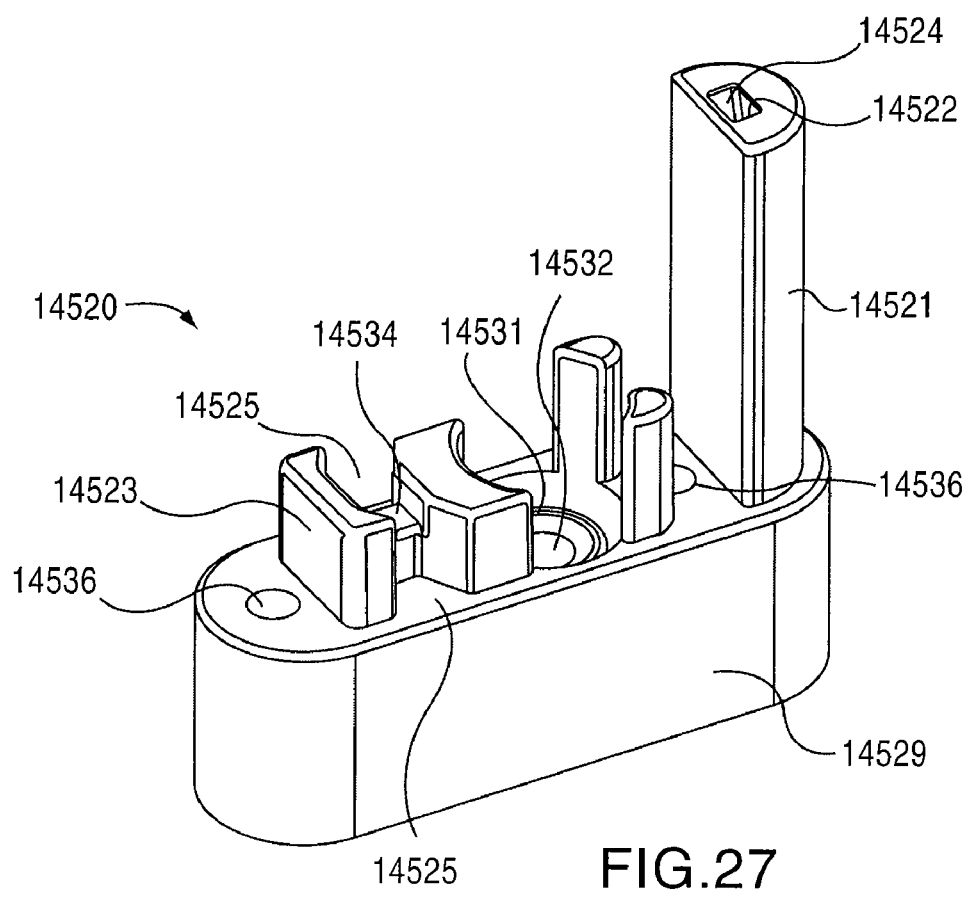

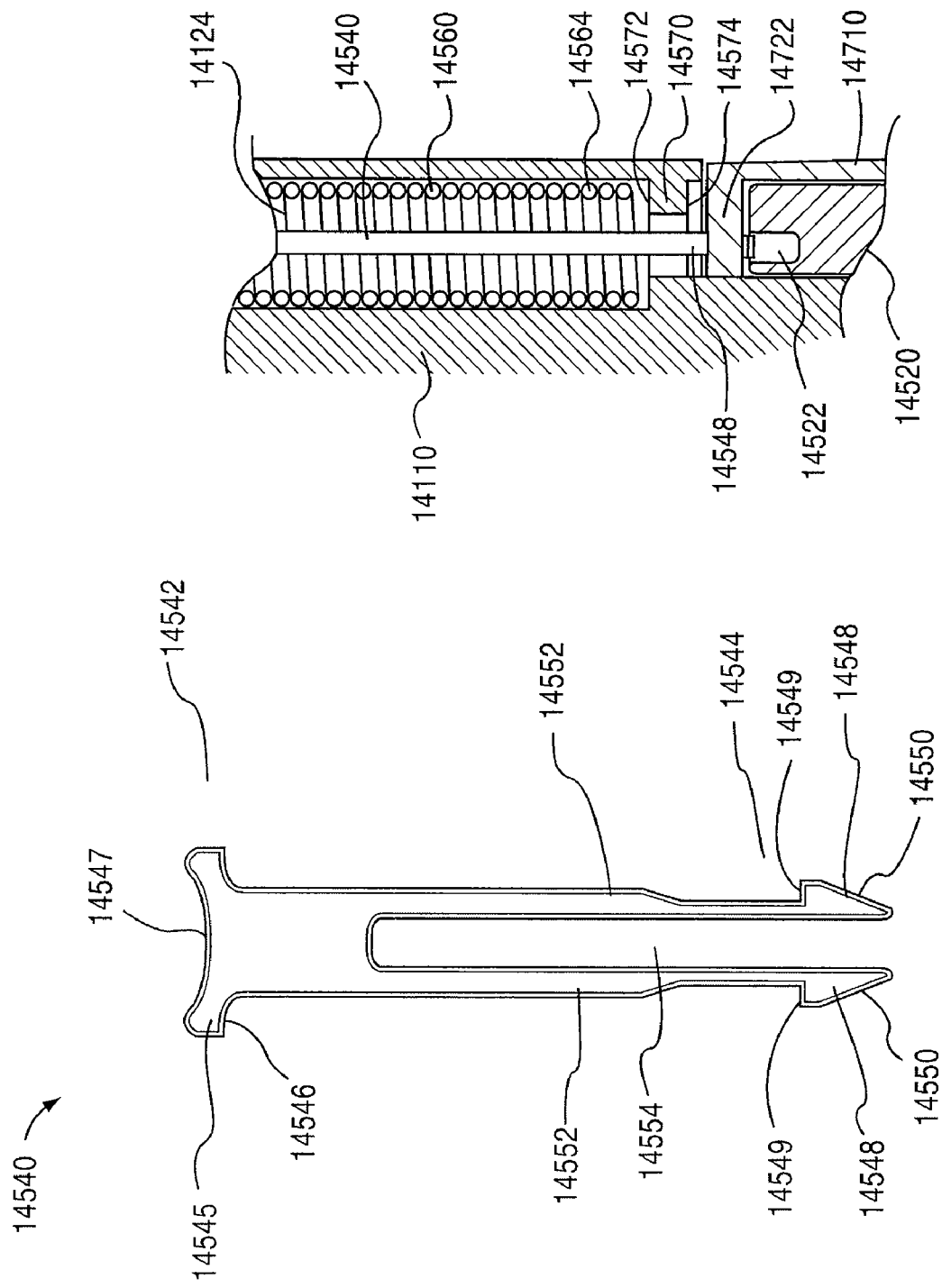

DEVICES, SYSTEMS AND METHODS FOR MEDICAMENT DELIVERY

CROSS-REFERENCE TO RELATED APPLICATIONS

This application claims priority to U.S. Provisional Application Ser. No. 60/787,046, entitled "Devices, Systems and Methods for Medicament Delivery," filed Mar. 29, 2006, which is incorporated herein by reference in its entirety.

The contents of each of the following commonly-owned patents and/or patent applications is hereby incorporated by reference in its entirety: U.S. patent application Ser. No. 11/671,025 (now U.S. Patent Publication No. 2007/0129708), entitled "Devices, Systems and Methods for Medicament Delivery," filed Feb. 5, 2007; U.S. patent application Ser. No. 11/621,236 (now U.S. Pat. No. 7,731,686), entitled "Devices, Systems and Methods for Medicament Delivery," filed Jan. 9, 2007; U.S. patent application Ser. No. 10/572,148 (now U.S. Pat. No. 7,749,194), entitled "Devices, Systems and Methods for Medicament Delivery," filed Mar. 16, 2006; International Patent Publication No. WO2006/083876, entitled "Devices, Systems and Methods for Medicament Delivery," filed Feb. 1, 2006; U.S. Provisional Application Ser. No. 60/648,822, entitled "Devices, Systems and Methods for Medicament Delivery," filed Feb. 1, 2005 and U.S. Provisional Application Ser. No. 60/731,886, entitled "Auto-Injector with Feedback," filed Oct. 31, 2005.

BACKGROUND

The invention relates generally to a medical device, and more particularly to a medicament delivery device for automatically mixing a medicament and injecting the medicament into a body of a patient.

Exposure to certain substances, such as, for example, peanuts, shellfish, bee venom, certain drugs, toxins, and the like, can cause allergic reactions in some individuals. Such allergic reactions can, at times, lead to anaphylactic shock, which can cause a sharp drop in blood pressure, hives, and/or severe airway constriction. Accordingly, responding rapidly to mitigate the effects from such exposures can prevent injury and/or death. For example, in certain situations, an injection of epinephrine (i.e., adrenaline) can provide substantial and/or complete relief from the allergic reaction. In other situations, for example, an injection of an antidote to a toxin can greatly reduce and/or eliminate the harm potentially caused by the exposure. Similarly, an injection of glucagon can reduce and/or or eliminate the harm potentially caused by reduced blood glucose levels in individuals who suffer from diabetes.

Because emergency medical facilities may not be available when an individual is suffering from a medical condition, some individuals carry an auto-injector to rapidly self-administer a medicament in response to such medical conditions. Some known auto-injectors are cylindrical in shape and include vial containing a liquid medicament and a spring loaded needle to automatically penetrate the user's skin and inject the medicament. The storage of certain medicaments in a liquid form, however, can result in a shorter shelf life and/or an unstable medicament. Accordingly, some known auto-injectors include a vial containing a first medicament and a medicament stored separately. Such auto-injectors are often referred to as "wet/dry" auto-injectors, because one medicament is often a liquid (e.g., water) and the other medicament is often a solid (e.g., glucagon powder). In use, the first medicament and the second medicament must be mixed prior to injection.

Some known wet/dry auto-injectors, however, require that the user manually actuate a mixing mechanism that must be used prior to injection. Such configurations can, however, result in incomplete mixing and/or injection occurring without mixing. Moreover, such configurations can be complicated, making them difficult for a user to operate during an emergency situation.

Some known wet/dry auto-injectors employ a single mechanism to automatically mix and inject the medicaments contained therein. Because the mixing operation is not independent from the injection operation in such configurations, however, the medicament can be injected prior to the completion of the mixing operation and/or prior to the auto-injector being properly positioned for the injection operation.

Thus, a need exists for an auto-injector that can separately store two or more medicaments and that can automatically mix and inject the medicaments in two distinct operations.

SUMMARY

Apparatuses and methods for automatic medicament injection are described herein. In some embodiments, an apparatus includes a housing and a medicament container disposed within the housing. The medicament container includes a first plunger and a second plunger, each disposed therein. The medicament container has a first configuration and a second configuration. In the first configuration, the first plunger is disposed in a first position within the medicament container and the second plunger is disposed in a second position spaced apart from the first position by a first distance. Accordingly, a first medicament containing portion is defined between the first plunger and the second plunger and a second medicament containing portion is defined between the second plunger and a distal end of the medicament container. In the second configuration, the first plunger is disposed in the first position within the medicament container and the second plunger is disposed in a third position spaced apart from the first position by a second distance. The second distance is less than the first distance. A volume of the second medicament containing portion is greater when the medicament container is in the second configuration than when the medicament container is in the first configuration.

BRIEF DESCRIPTION OF THE DRAWINGS

FIG. 26 is a perspective view of a member of the auto-injector illustrated in FIG. 14.

FIG. 27 is a perspective view of a member of the auto-injector illustrated in FIG. 14.

FIG. 29 is a front view of a member of the auto-injector illustrated in FIG. 14.

FIG. 30 is a cross-sectional front view of the portion of the auto-injector labeled as 30 in FIG. 16.

DETAILED DESCRIPTION

Figure 1:
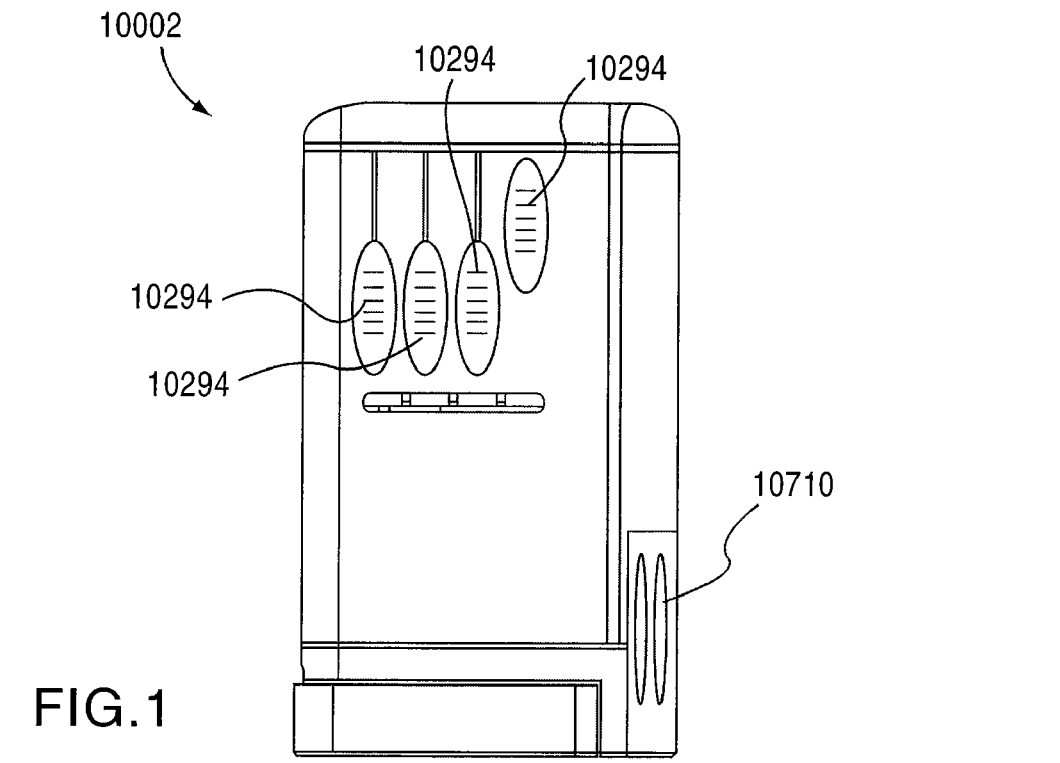
FIG. 1 is a front view of a medical device according to an embodiment of the invention.

In some embodiments, an apparatus includes a housing and a medicament container disposed within the housing. The medicament container includes a first plunger and a second plunger, each disposed therein. The medicament container has a first configuration and a second configuration. In the first configuration, the first plunger is disposed in a first position within the medicament container and the second plunger is disposed in a second position spaced apart from the first position by a first distance. Accordingly, a first medicament containing portion is defined between the first plunger and the second plunger, which can contain, for example, a liquid medicament. A second medicament containing portion is defined between the second plunger and a distal end of the medicament container, which can contain, for example, a solid medicament. In the second configuration, the first plunger is disposed in the first position within the medicament container and the second plunger is disposed in a third position spaced apart from the first position by a second distance. The second distance is less than the first distance. A volume of the second medicament containing portion is greater when the medicament container is in the second configuration than when the medicament container is in the first configuration.

In some embodiments, an apparatus includes a housing, a medicament container disposed within the housing, a first movable member and a second movable member. The medicament container has a first plunger disposed within a proximal end portion of the medicament container and a second plunger disposed therein spaced apart from the first plunger. The first movable member is configured to move the first plunger within the medicament container toward a distal end of the medicament container. The second movable member is configured to move the second plunger within the medicament container toward the proximal end portion of the medicament container. In some embodiments, for example, the second movable member can be configured to move the second plunger without moving the first plunger.

In some embodiments, an apparatus includes a housing, a medicament container disposed within the housing, a first energy storage member and a second energy storage member. The medicament container has a first plunger disposed within a proximal end portion of the medicament container and a second plunger disposed therein spaced apart from the first plunger. The first energy storage member, which can be, for example, a compressed gas container, is configured to produce a force when moved from a first configuration to a second configuration to move the first plunger within the medicament container. The second energy storage member, which is different from the first energy storage member and can be, for example, as spring, is configured to produce a force when moved from a first configuration to a second configuration to move the second plunger within the medicament container.

In some embodiments, an apparatus includes a housing, a medicament container disposed within the housing, and a movable member. The medicament container has a first plunger disposed within a proximal end portion of the medicament container and a second plunger disposed therein such that the medicament container is divided into a first medicament containing portion and a second medicament containing portion. The movable member is configured to move the second plunger within the medicament container to mix a medicament contained in the first medicament containing portion with a medicament contained in the second medicament containing portion. The movable member is offset from a longitudinal axis of the medicament container.

In some embodiments, a method includes moving a mixing plunger within a medicament container toward a proximal end of the medicament container. The mixing plunger is disposed within the medicament container between a distal end of the medicament container and an injection plunger disposed at the proximal end of the medicament container. The injection plunger is moved within the medicament container toward a distal end of the medicament container to expel a medicament contained within the medicament container.

As used in this specification and the appended claims, the term "medicament" includes any constituent of a therapeutic substance. A medicament can include such constituents regardless of their state of matter (e.g., solid, liquid or gas). Moreover, a medicament can include the multiple constituents that may be included in a therapeutic substance in a mixed state, in an unmixed state and/or in a partially mixed state. A medicament can include both the active constituents and inert constituents of a therapeutic substance. Accordingly, as used herein, a medicament can include non-active constituents such as, water, colorant or the like.

Figure 2:
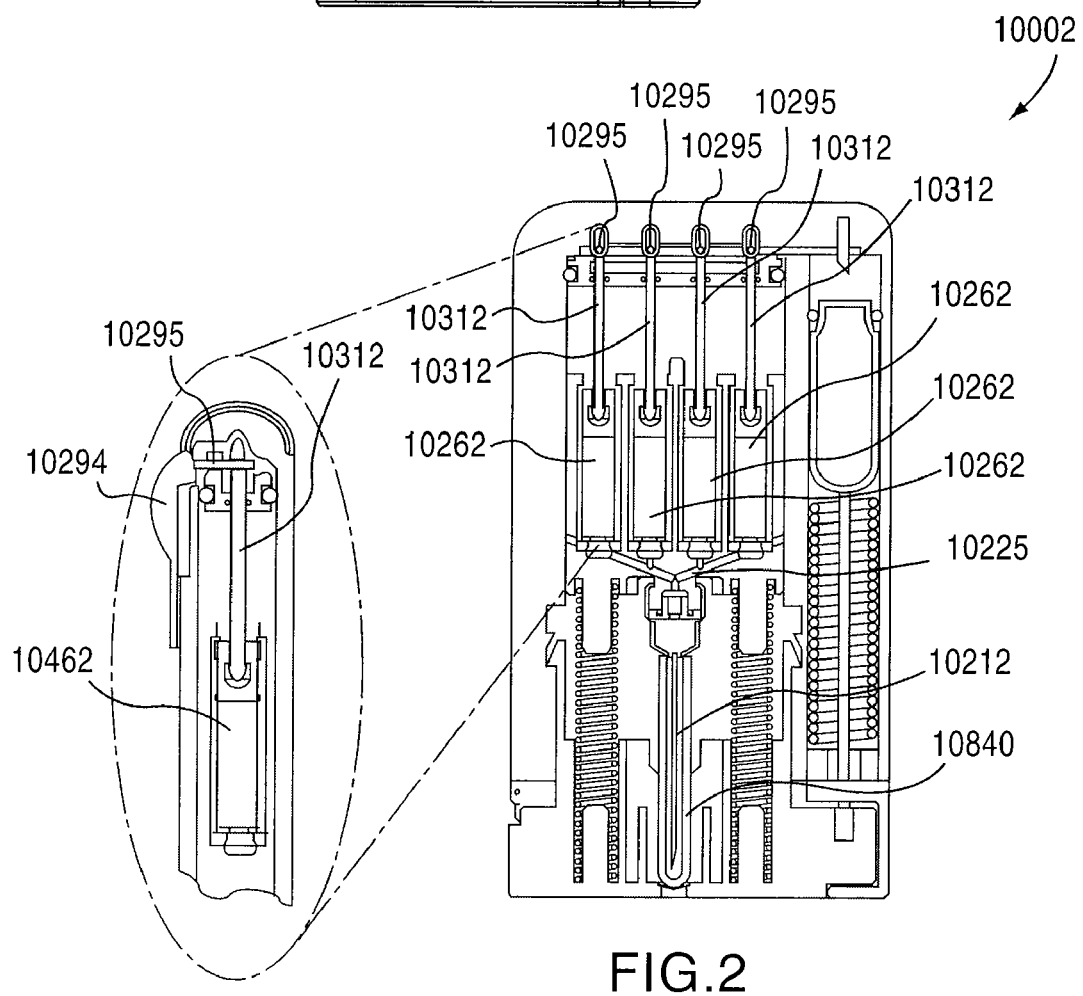
FIG. 2 is a cross-sectional view of the medical device shown in FIG. 1.

FIGS. 1 and 2 show a compact auto-injector 10002 that includes a plurality of vials 10262, allowing for multiple medicaments to be injected at one time or at different times. The auto-injector 10002 also can comprise a needle protection system 10840.

The auto-injector 10002 can include medicament selectors 10294 in order to allow the user to select which medicament to inject. The user can select the medicaments by sliding one or more selectors 10294 upward into their final position. An audible click or some other indicator may occur to alert the user to this final position. Moving the selector 10294 or multiple selectors 10294 upwards can allow a pin 10295 to snap into the plunger rod 10312 and/or into the pusher bar (not shown in FIG. 2), which can create an entire portion that can push the vial system downwards and can inject the medication through the vial 10262, the reservoir 10225 and/or needle 10212. This method can also be used with a needleless injector method as shown and described earlier in U.S. patent application Ser. No. 10/572,148, entitled "Devices, Systems and Methods for Medicament Delivery," filed Mar. 16, 2006, which is incorporated herein by reference in its entirety. Methods such as this embodiment could be extremely useful in applications for anti-nerve agents or pain therapies. The device can also include a resilient material, such as rubber, to seal the selector openings and that can also slide within the housing once the selector is pushed upward. Once the aforementioned pins 10295 are in place, the device 10002 can function and activate as described in U.S. patent application Ser. No. 11/562,061, entitled "Devices, Systems and Methods for Medicament Delivery," filed Nov. 21, 2006, which is incorporated herein by reference in its entirety. In some embodiments, a safety mechanism 10710 can be modified to eliminate the sliding selectors from being prematurely pushed upwards.

Figure 3:
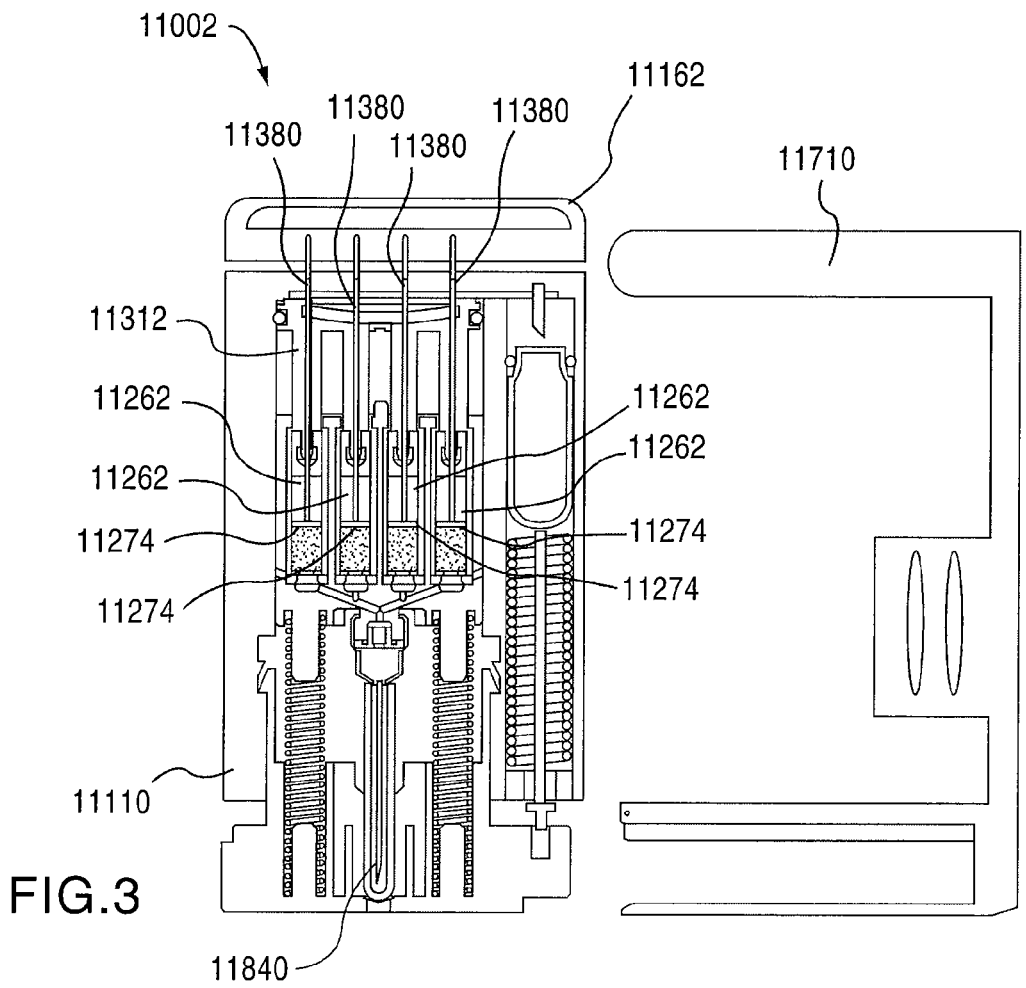
FIG. 3 is a cross-sectional view of a medical device according to an embodiment of the invention.

FIG. 3 depicts an apparatus and method for injecting lyophilized medications, and/or powdered biologics that could need to be reconstituted pre-injection. FIG. 3 shows an auto-injector 11002 including a mechanism to mix and/or create an injectable medicament from two or more separate aforementioned substances. The auto-injector 11002 includes multiple vials 11262 that could have two substances in each vial 11262 separated by a pierceable membrane 11274 and/or other frangible piece. The vials 11262 in this embodiment can have one wet substance (such as sterilized water) and one dry substance (such as glucagon powder).

The user can take off the safety tab 11710 which can prevent the user from accidental injection and/or pre-mature activation of the device. Once the safety tab 11710 is removed, the user can twist and/or rotate the twisting portion 11162 at the top of the housing 11110. By rotating this top portion 11162, the rods 11380 attached to this portion (which can be threaded rods) can move downward. The rods 11380 can be located in the vials 11262 and/or through the pusher bar 11312. The rods 11380 can have a sharp piercing portion on the distal end which can aid in puncturing the aforementioned pierceable membrane 11274 that can separate the substances in the vial 11262. Once the piercing rod 11380 punctures the frangible seal and/or pierceable membrane 11274, the substances can mix together to form one medicament. The user can also shake the entire housing 11110 in order to aid in this mixing process. Accordingly, this embodiment can comprise a compact auto-injector 11002 that can have the ability to mix two or more medicaments in either a liquid or powder form to create one injectable medicament. The device also can comprise a needle protection system 11840.

An exemplary delivery system can comprise a housing, plurality of vials, a plunger for each vial, a mixing activation mechanism, an activation chamber or vial, single needle or needle cannula, and/or a medicament or medicaments stored within each vial. Pre-injection, two or more medicaments can be stored separately in a vial and/or storage compartment and can communicate with each other once the mixing activation mechanism is initialized. The mixing activation mechanism could comprise a button, trigger, threaded rod, and or some other member that removes a piece or portion and/or punctures a piece or portion that is preventing each medicament to communicate with each other. The mixing activation mechanism may comprise a membrane, piece, and/or portion that may be removed pre-injection by the user in order to allow the separate vials and/or storage containers to communicate with each other. The mixing activation mechanism can be a piece that is manipulated in some way by the user in order to cause the contents of each compartment to mix with each other. This communication may occur by shaking the device and/or may occur automatically with the mixing activation mechanism. For instance, the mixing activation mechanism may cause each medicament to be released into an activation chamber, which may itself be a separate vial. This mixed medicament can be the medicament that will be injected into the patient.

FIGS. 4-7 are schematic illustrations of a medical device 12002 according to an embodiment of the invention in a first configuration, a second configuration, a third configuration and a fourth configuration, respectively. The medical device 12002 can be any suitable device for delivering a medicament into a body, such as for example, a syringe, a medical injector, an auto-injector or the like. The medical device 12002 includes a housing 12110 that contains a medicament container 12262. The medicament container 12262 has a proximal end portion 12264 and a distal end portion 12266. The medicament container 12262 includes a first plunger 12284 and a second plunger 12282.

Figure 4:
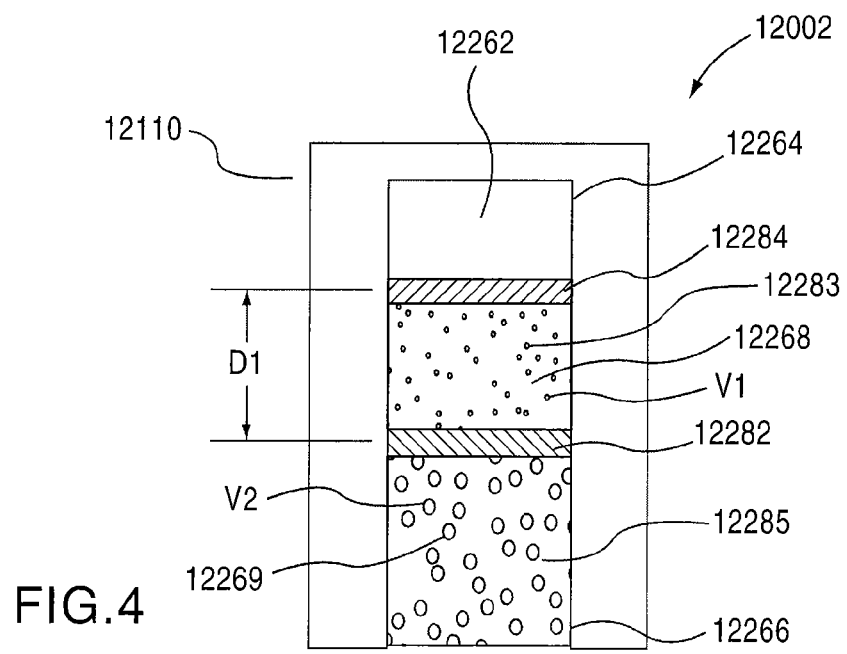
FIGS. 4-7 are schematic illustrations of a medical device according to an embodiment of the invention in a first configuration, a second configuration, a third configuration and a fourth configuration, respectively.

As shown in FIG. 4, when the medical device 12002 is in the first configuration, the first plunger 12284 is disposed in a first position within the medicament container 12262. The second plunger 12282 is disposed in a second position within the medicament container 12262. The second position is spaced apart from the first position by a first distance D1. In this manner, a first medicament containing portion 12283 having a volume V1 is defined between the first plunger 12284 and the second plunger 12282. Similarly, a second medicament containing portion 12285 having a volume V2 is defined between the second plunger 12282 and the distal end portion 12266 of the medicament container 12262. In some embodiments, the medicament container 12262 can be a cartridge, a vial, an ampule, or the like that is filled with one or more medicaments. For example, in some embodiments, the first medicament containing portion 12283 can include a liquid medicament 12268, such as a water, and the second medicament containing portion 12285 can include a second medicament 12269, such as a lyophilized powder. Similarly, in some embodiments, the first medicament containing portion 12283 can include a liquid medicament 12268 that is devoid of a gas (e.g., stored in a vacuum) and/or the second medicament containing portion 12285 can include a solid medicament 12269 that is devoid of a gas (e.g., stored in a vacuum).

Figure 5:
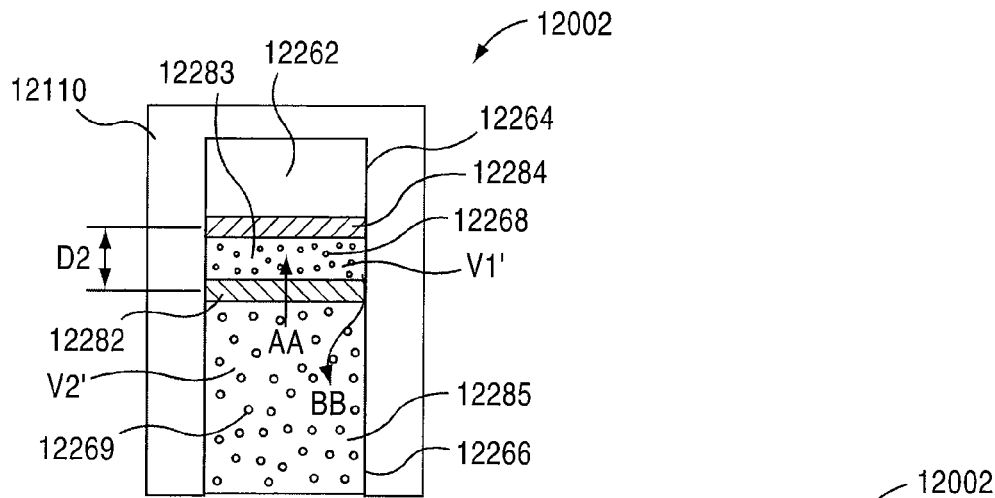

As shown in FIG. 5, when the medical device 12002 is in the second configuration, the first plunger 12284 remains disposed in the first position within the medicament container 12262. The second plunger 12282 is disposed in a third position within the medicament container 12262. The third position is spaced apart from the first position by a second distance D2 that is less than the first distance D1. Said another way, when the medical device 12002 is in the second configuration, the volume V2' of the second medicament containing portion 12285 is greater than the volume V2 when the medicament container 12262 is in the first configuration. Similarly, because the first plunger 12284 remains disposed in the first position, the total volume of the medicament container 12262 when the medical device 12002 is in the first configuration (V1+V2) is the same as the total volume of the medicament container 12262 when the medical device 12002 is in the second configuration (V1'+V2'). Said another way, the area between the first plunger 12284 and the distal end portion 12266 defines a constant volume when the second plunger 12282 moves from its first position to its second position In some embodiments, when the medical device 12002 is moved from the first configuration to the second configuration, as indicated by the arrow AA in FIG. 5, a portion of the first medicament 12268 contained in the first medicament containing portion 12283 can be conveyed to the second medicament containing portion 12285, as indicated by the arrow BB in FIG. 5. Said another way, when the second plunger 12282 moves towards the proximal end 12264 of the medicament container 12262, a portion of the contents of the first medicament containing portion 12283 can be conveyed to the second medicament containing portion 12285. In this manner, the medical device 12002 can combine and/or mix the first medicament 12268 with the second medicament 12269 contained in the second medicament containing portion 12285 to produce a mixture suitable for delivery via the medical device 12002.

In some embodiments, the first medicament containing portion 12283 can be fluidically isolated from the second medicament containing portion 12285 when the medical device 12002 is in the first configuration. The first medicament containing portion 12283 can be in fluid communication with the second medicament containing portion 12285 when the medical device 12002 is moving from the first configuration to the second configuration. In some embodiments, for example, the second plunger 12282 can form a fluid-tight seal within the medicament container 12262 when the medicament container 12262 is in the first configuration. The second plunger 12282 and/or the medicament container 12262 can further be configured to allow fluid communication between the first medicament containing portion 12283 and the second medicament containing portion 12285 when the second plunger 12282 is moving from its first position to its second position. In this manner, the medical device 12002 can be configured to store the first medicament 12268 (e.g., a liquid medicament) separately from the second medicament 12269 (e.g., a lyophilized powder) until such time as the first medicament 12268 and the second medicament 12269 are combined and/or mixed in preparation for delivery into the body.

Figure 6:
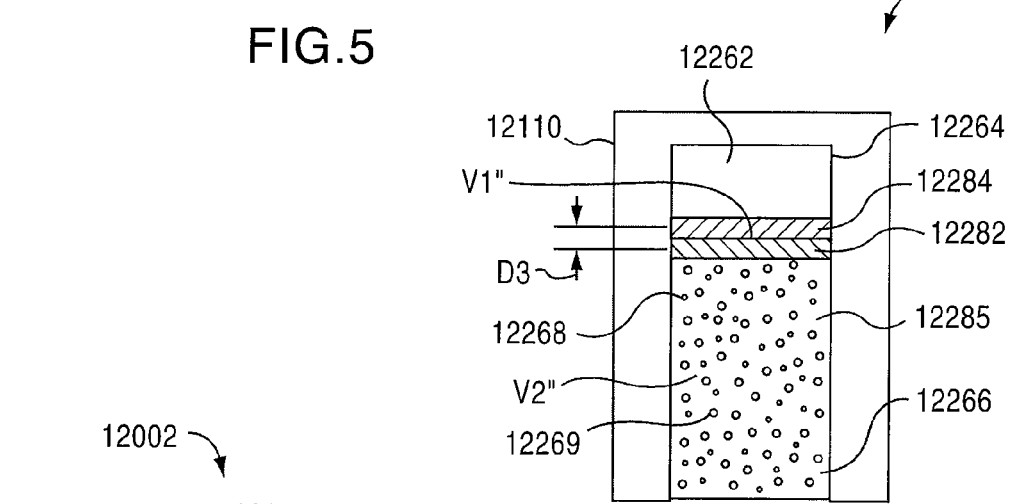

As shown in FIG. 6, when the medical device 12002 is in the third configuration, the first plunger 12284 remains disposed in the first position within the medicament container 12262. The second plunger 12282 is disposed in a fourth position within the medicament container 12262. The fourth position is spaced apart from the first position by a third distance D3 that is less than the second distance D2. Moreover, when the second plunger 12282 is in the fourth position, a portion of the second plunger 12282 is in contact with a portion of the first plunger 12284. In some embodiments, when the second plunger 12282 is in the fourth position, it engages the first plunger 12284 such that there is no space between the first plunger 12284 and the second plunger 12282 (i.e., D3 is zero). Said another way, when the medical device 12002 is in the third configuration, the volume V1" of the first medicament containing portion 12283 is substantially zero. Moreover, the volume V2" of the second medicament containing portion 12285 is substantially equal to the total volume of the medicament container 12262 when the medical device 12002 is in the first configuration (V1+V2). In this manner, when the medical device 12002 is in the third configuration, substantially all of the first medicament 12268 and substantially all of the second medicament 12269 are contained within the second medicament containing portion 12285. The first medicament 12268 and the second medicament 12269 can be contained within the second medicament containing portion 12285 in any suitable form. For example, in some embodiments, when the medical device 12002 is in the third configuration, the first medicament 12268 and the second medicament 12269 can form a non-homogenous mixture, a homogeneous mixture, a solution, a suspension and/or a combination.

Figure 7:
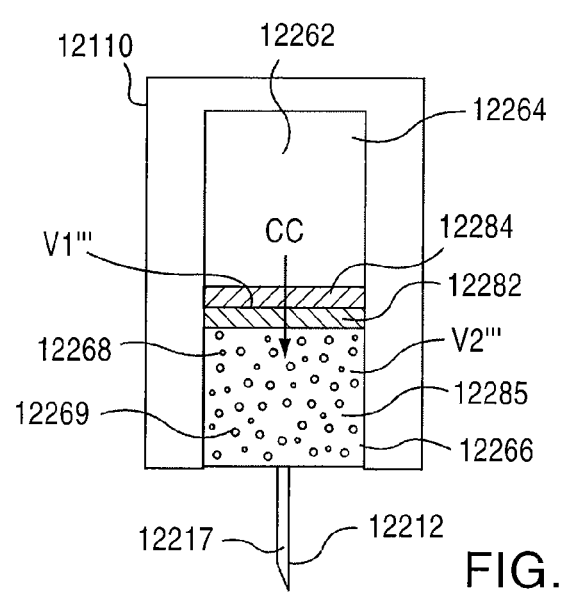

As shown in FIG. 7, when the medical device 12002 is in the fourth configuration, the first plunger 12284 is disposed in a fifth position within the medicament container 12262. The second plunger 12282 is disposed in a sixth position within the medicament container 12262, such that a portion of the second plunger 12282 is in contact with a portion of the first plunger 12284. Moreover, when the medical device 12002 is in the fourth configuration, the volume V1''' of the first medicament containing portion 12283 is substantially zero and the volume V2''' of the second medicament containing portion 12285 is less than the total volume of the medicament container 12262 when the medical device 12002 is in the first configuration (V1+V2). Said another way, when the medical device 12002 is in the fourth configuration, the first plunger 12284 and the second plunger 12282 are collectively moved distally within the medicament container 12262 as indicated by the arrow CC in FIG. 7. In this manner, the first medicament 12268 and the second medicament 12269 can be collectively expelled from the distal end portion 12266 of the medicament container 12262.

As shown in FIG. 7, in some embodiments, the medical device 12002 includes a needle 12212 that can be disposed at the distal end portion 12266 of the medicament container. When the medical device 12002 is in the first configuration, the second configuration and/or the third configuration, a lumen 12217 defined by the needle 12212 is fluidically isolated from the first medicament containing portion 12283 and/or the second medicament containing portion 12285. When the medical device 12002 is in the fourth configuration, the a lumen 12217 defined by the needle 12212 is in fluid communication with the first medicament containing portion 12283 and/or the second medicament containing portion. In this manner, when the medical device 12002 is moving between the first configuration, the second configuration and the third configuration, the first medicament 12268 and the second medicament 12269 can be combined and/or mixed without the first medicament 12268 and/or the second medicament 12269 being expelled from the medicament container. Similarly, when the medical device 12002 is in the fourth configuration, the first medicament 12268 and the second medicament 12269 can be collectively injected into a body via the needle 12212.

Figure 8:
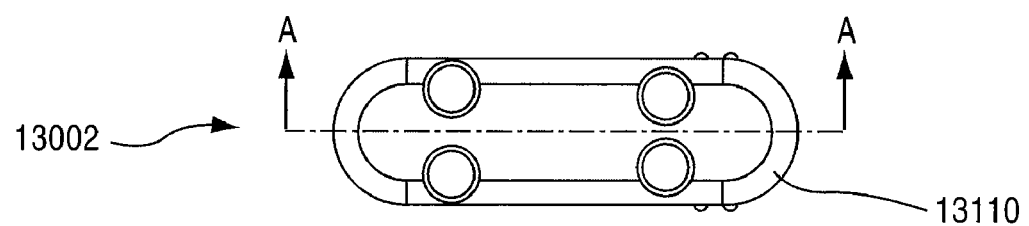
FIG. 8 is a top view of an auto-injector according to an embodiment of the invention.
Figure 9:
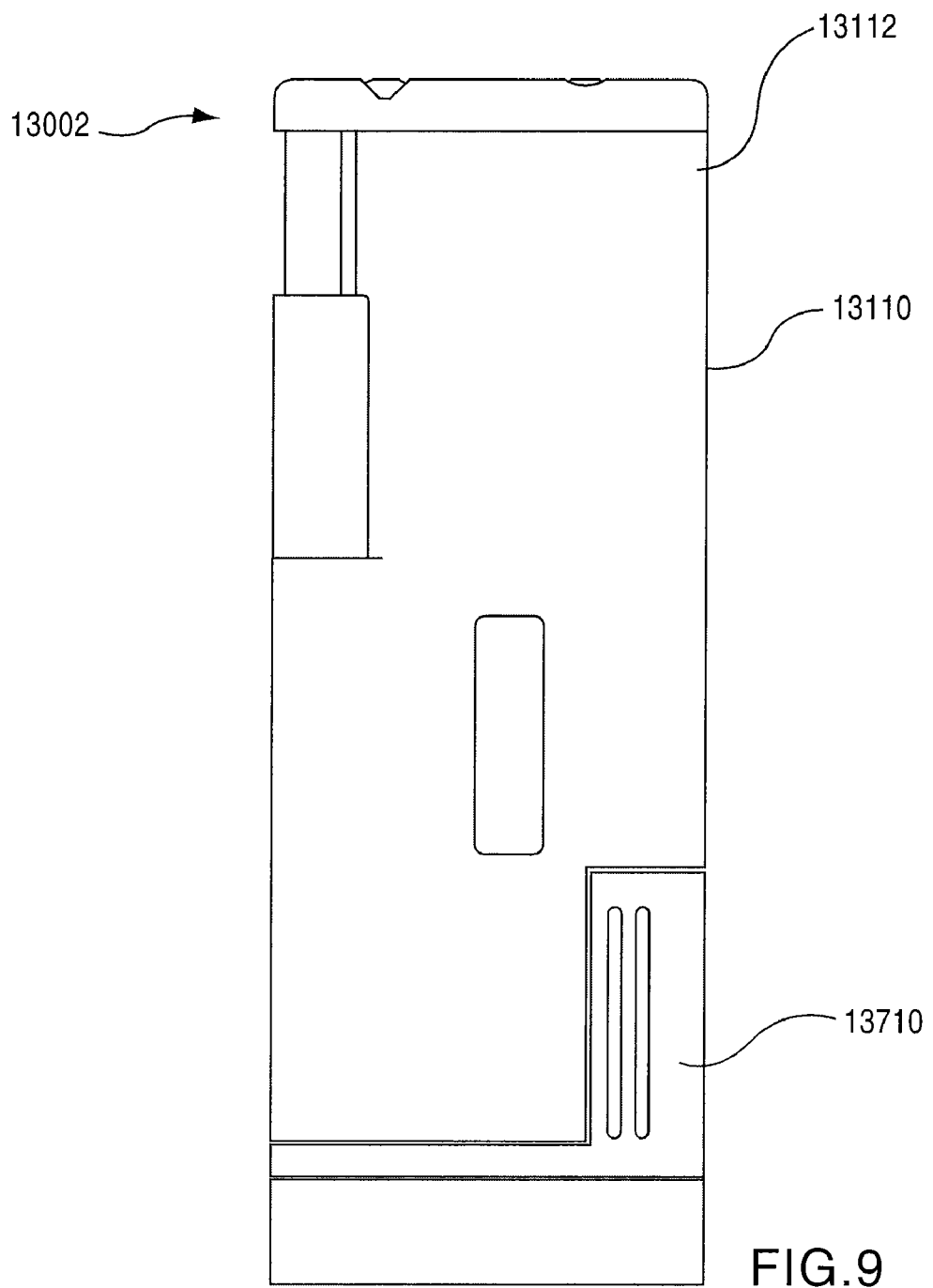
FIG. 9 is a front view of the auto-injector shown in FIG. 8.
Figure 10:
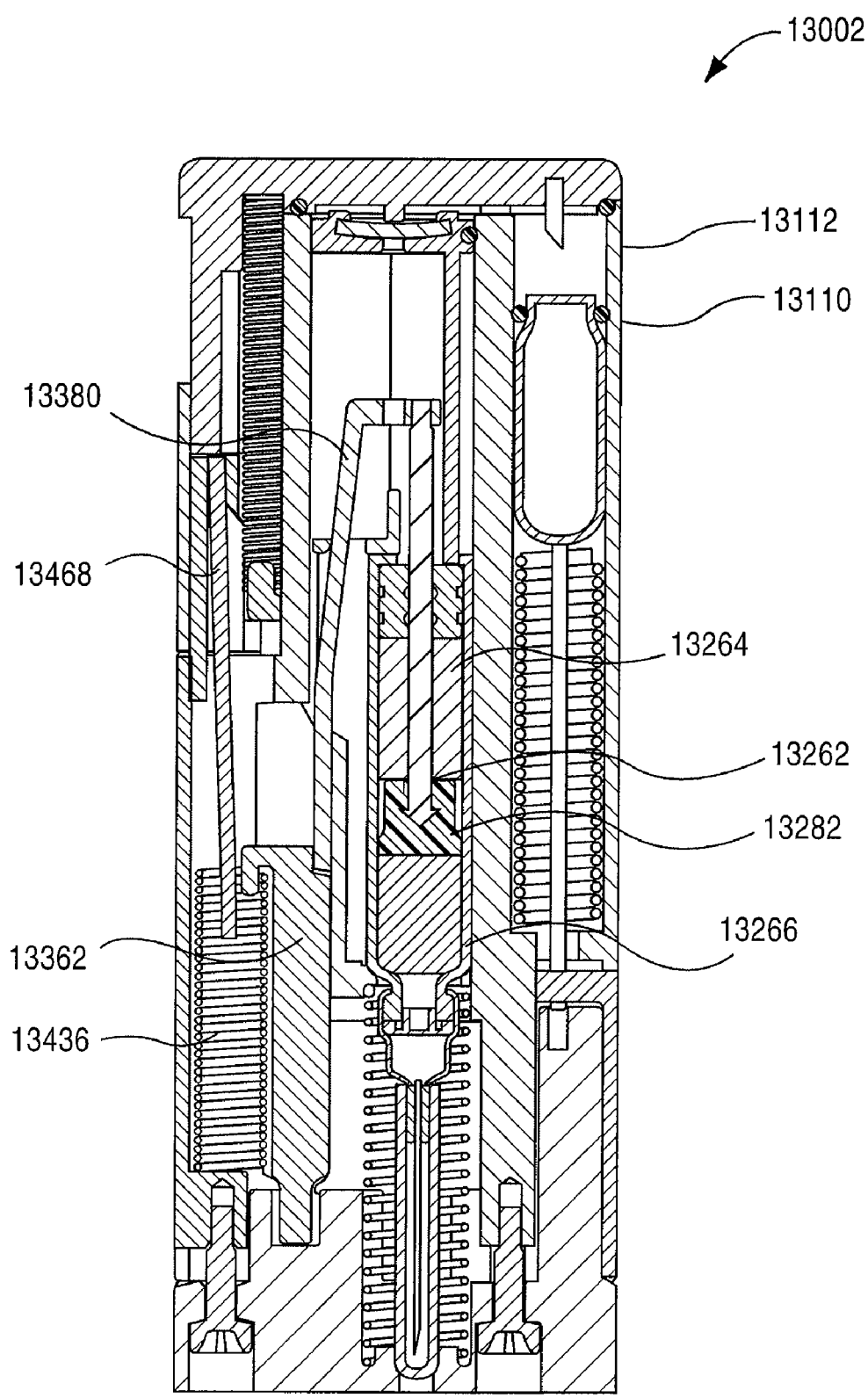
FIG. 10 is a cross-sectional view of the auto-injector shown in FIG. 8 taken along line A-A in FIG. 8.
Figure 11:
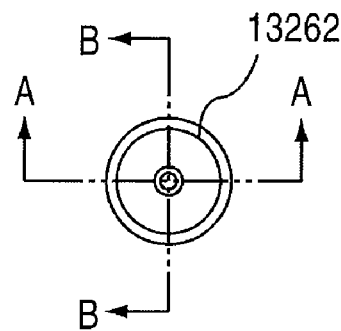
FIG. 11 is a top view of a portion of the auto-injector shown in FIG. 8.
Figure 12:
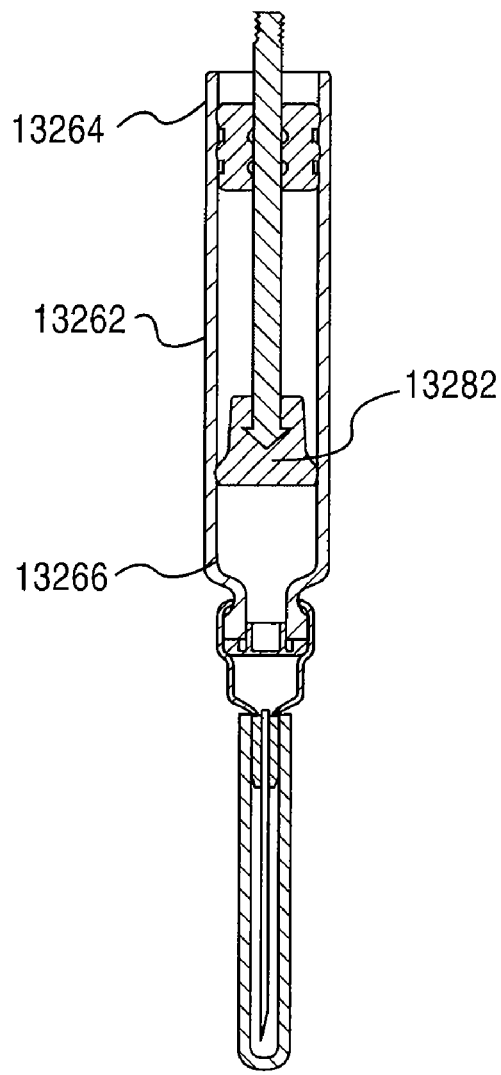
FIG. 12 is a cross-sectional view of the portion of the auto-injector shown in FIG. 11 taken along line A-A in FIG. 11.
Figure 13:
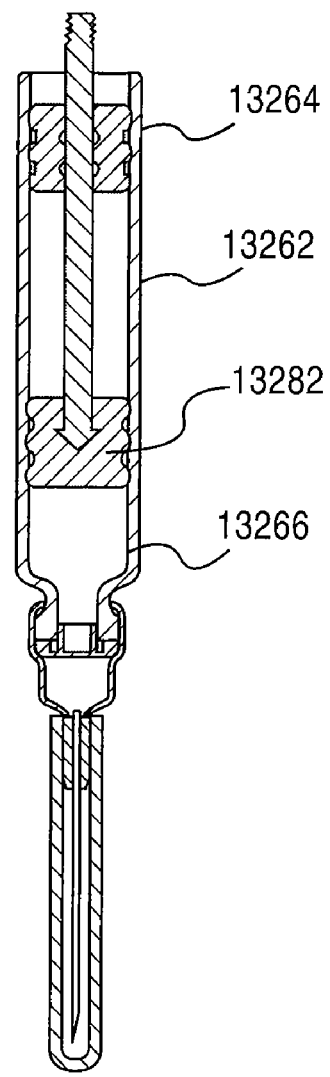
FIG. 13 is a cross-sectional view of the portion of the auto-injector shown in FIG. 11 taken along line B-B in FIG. 11.

FIGS. 8-10 depict an apparatus for injecting lyophilized medications, and/or powdered biologics that could need to be reconstituted pre-injection. FIGS. 8-10 show an auto-injector 13002 to mix and/or create an injectable medicament from two or more separate aforementioned substances. FIGS. 11-13 depict a single vial 13262 that could have two substances in the vial 13262 separated by a plunger 13282 and/or other frangible piece that may be located in the auto-injector 13002 shown in FIGS. 8-10. The vial 13262 in this embodiment can contain one wet substance (such as sterilized water) and one dry substance (such as glucagon powder).

To mix the substances, the user can push a button or trigger 13468 at the side of the housing 13110 to initiate the reconstitution and mixing of the two substances. By pushing this button or trigger 13468, a spring 13436 can be activated and forced toward the proximal end 13112 of the housing 13110. This spring 13436 can be attached to a solid member 13362 which can be attached to a member 13380 connected to the plunger 13282 or membrane in the vial 13262. As the spring 13436 is forced upward, the solid member 13362 and therefore plunger/membrane 13282 can be forced upward toward the proximal end 13264 of the vial 13262. This force can cause the wet substance to bypass the plunger/membrane 13282, moving down toward the distal end 13266 of the vial 13262 and can thereby cause the wet substance to mix with the dry substance forming the new injectable medicament. The user can shake the entire housing 13110 in order to aid in this mixing process. The user can then take off the safety tab 13710 located at the base of the auto-injector 13002 and operate the auto-injector 13002.

Some embodiments can include a method for reconstitution with an auto-injector. Some embodiments can comprise a compact auto-injector that can have the ability to mix two or more medicaments in either a liquid or powder form to create one injectable medicament. Some embodiments can use a secondary activation mechanism in order to effectively mix the two substances to form one injectable medicament. The device can comprise a needle protection system.

An exemplary delivery system can comprise a housing, vial or plurality of vials, plunger for each vial, a mixing activation mechanism, an activation chamber or vial, single needle or needle cannula, and/or a medicament or medicaments stored within each vial. Pre-injection, two or more medicaments can be stored separately in a vial and/or storage compartment and can communicate with each other once the mixing activation mechanism is initialized.

The mixing activation mechanism could comprise a button, trigger, plunger, spring and or some other member or combination of members that, once activated, can cause the two or more medicaments to interact with each other to form one injectable medicament.

The mixing mechanism can comprise a membrane, piece, plunger and/or portion that can be manipulated pre-injection by the user using the aforementioned mixing activation mechanism in order to allow the separate substances to fluidly communicate with each other. For instance, the mixing activation mechanism can activate a spring attached to solid member that is attached to a plunger in one vial. This plunger can be separating two substances (one wet and one dry) within one vial by being placed in between the two substances. The activated spring can push the solid member and plunger upwards toward the proximal end of the aforementioned vial, which can force the wet part past the plunger to interact with the dry part, forming the newly mixed injectable medicament.

The delivery system can further encompass the mixed medicament vial or plurality of mixed medicament vials in fluid communication with a reservoir that can contain a single needle or needle cannula at the distal end. The needle can be protected by some sheath/shield.

The housing can further comprise a passage that is in fluid communication with the proximal end of the plunger such that when the spring(s) is activated from the distal or proximal end, a force can be applied through the passage on the plunger at the proximal end allowing for the plunger(s), vial(s), reservoir, and/or needle to travel towards the distal end of the housing. The force provided can be caused by a spring, bar, contents from a gas cylinder, and/or other force mechanism. The plunger can slideably travel through the vial towards the distal end to allow for the appropriate dose of medicament to be delivered. Upon exit of the desired contents of the vial, the entire needle, reservoir, vial, and/or plunger assembly can retract towards the proximal end of housing by some means such as a wire, spring, o-ring, and/or rubber membrane and/or a needle protection portion slides over the needle following delivery of the medicament.

Figure 14:
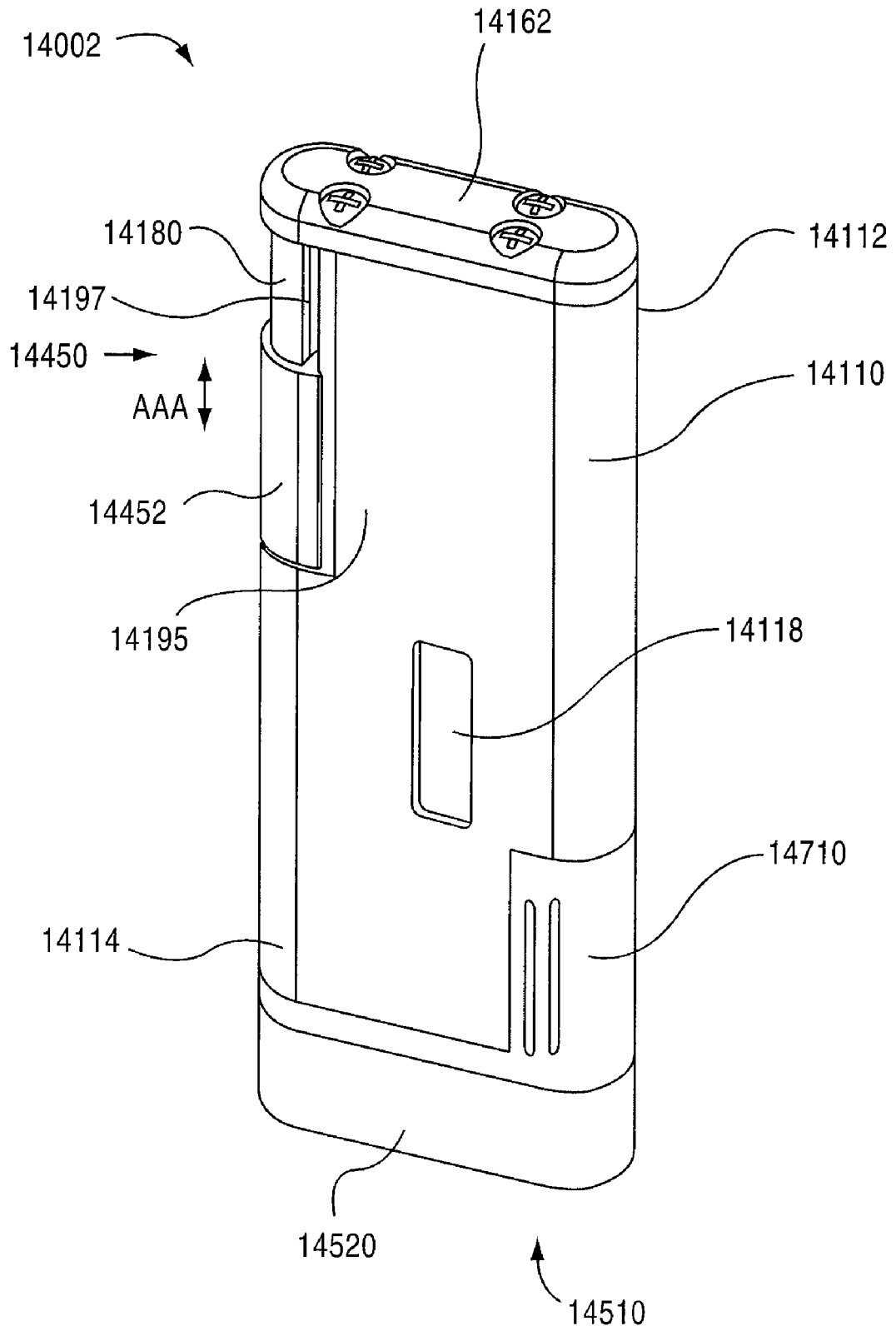
FIG. 14 is a perspective view of an auto-injector according to an embodiment of the invention.

FIG. 14 is a perspective view of an auto-injector 14002 according to an embodiment of the invention in a first configuration. The auto-injector 14002 includes a housing 14110 having a proximal end portion 14112 and a distal end portion 14114. A proximal cover 14162 is disposed at the proximal end portion 14112 of the housing 14110. A mixing actuator 14450 is disposed adjacent the proximal end portion 14112 at a side portion 14195 of the housing 14110. A safety cover 14452 is slidably coupled to the side portion 14195 of the housing 14110. Similarly, an injection actuator 14510, which includes a base 14520, is disposed at the distal end portion 14114 of the housing 14110. An actuation safety lock 14710 is removably coupled adjacent the distal end portion 14114 of the housing 14110. The housing 14110 also includes a transparent status window 14118 to allow a user to determine the status of the auto-injector 14002 and/or the medicament contained therein.

Figure 15:
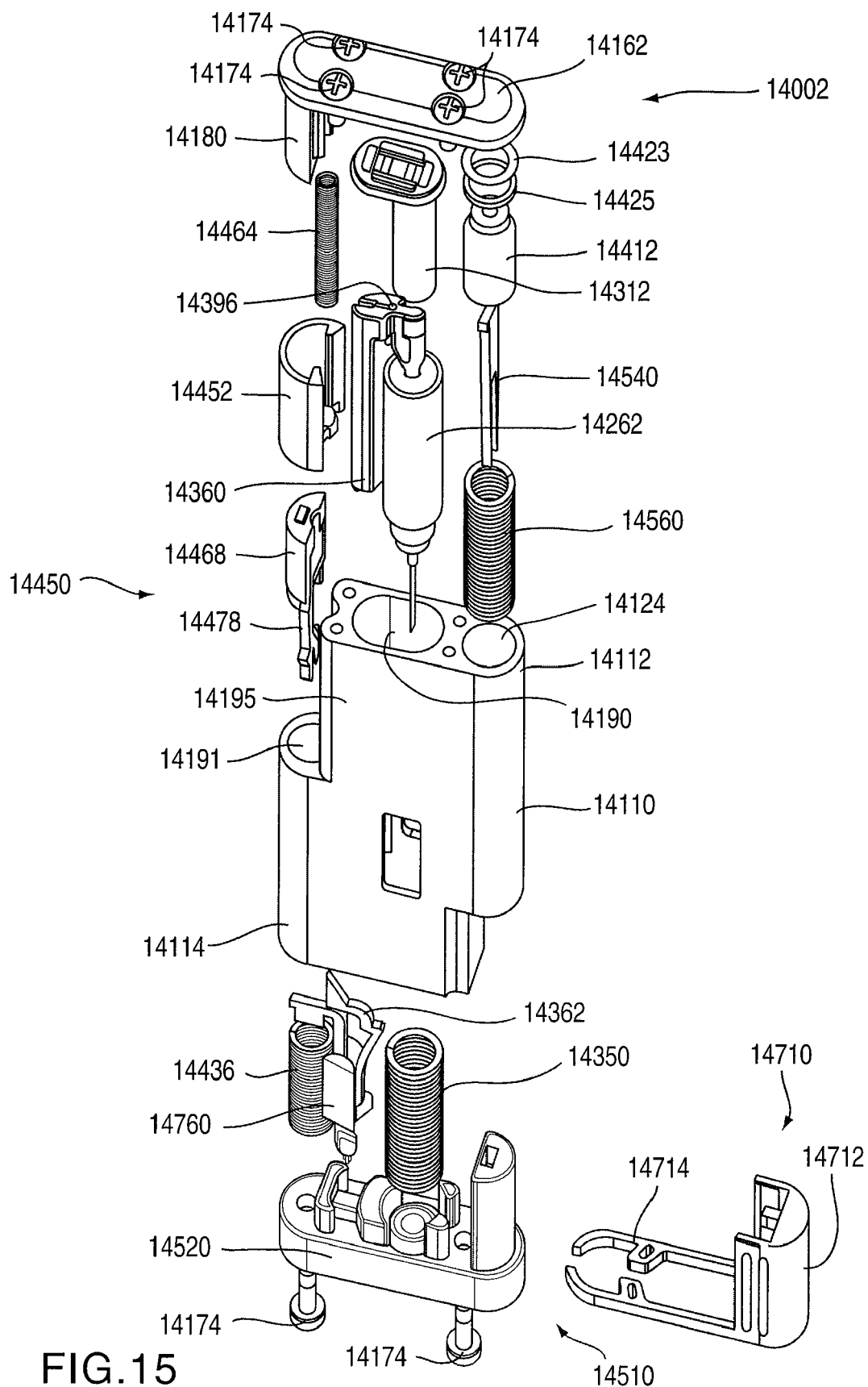
FIG. 15 is a perspective exploded view of the auto-injector shown in FIG. 14.

To inject a medicament into the body, the safety cover 14452 is moved towards the proximal end portion 14112 of the housing 14110 to uncover the mixing actuator button 14468 (see FIG. 15). The mixing actuator button 14468 is moved inwardly to actuate the medicament mixer 14360 (see FIG. 15), which can combine and/or mix different medicaments contained within the auto-injector 14002 to produce a mixture suitable for delivery via the auto-injector 14002.

After the medicament is suitably mixed, the distal end portion 14114 of the housing is oriented towards the user such that the base 14520 is in contact with the portion of the body where the injection is to be made. The base 14520 is then moved (after the removal of the actuation safety lock 14710) towards the proximal end 14112 of the housing 14110 to actuate the auto-injector 14002. Upon actuation, the medicament is injected into the body through a needle 14212 (see FIG. 16). The needle 14212 is automatically retracted when the injection is complete. The use of the auto-injector 14002 includes several discrete operations and involves many different components. Accordingly, a detailed description of the components contained in the auto-injector 14002 is presented below, followed by a step-by-step description of operation of the auto-injector 14002.

Figure 16:
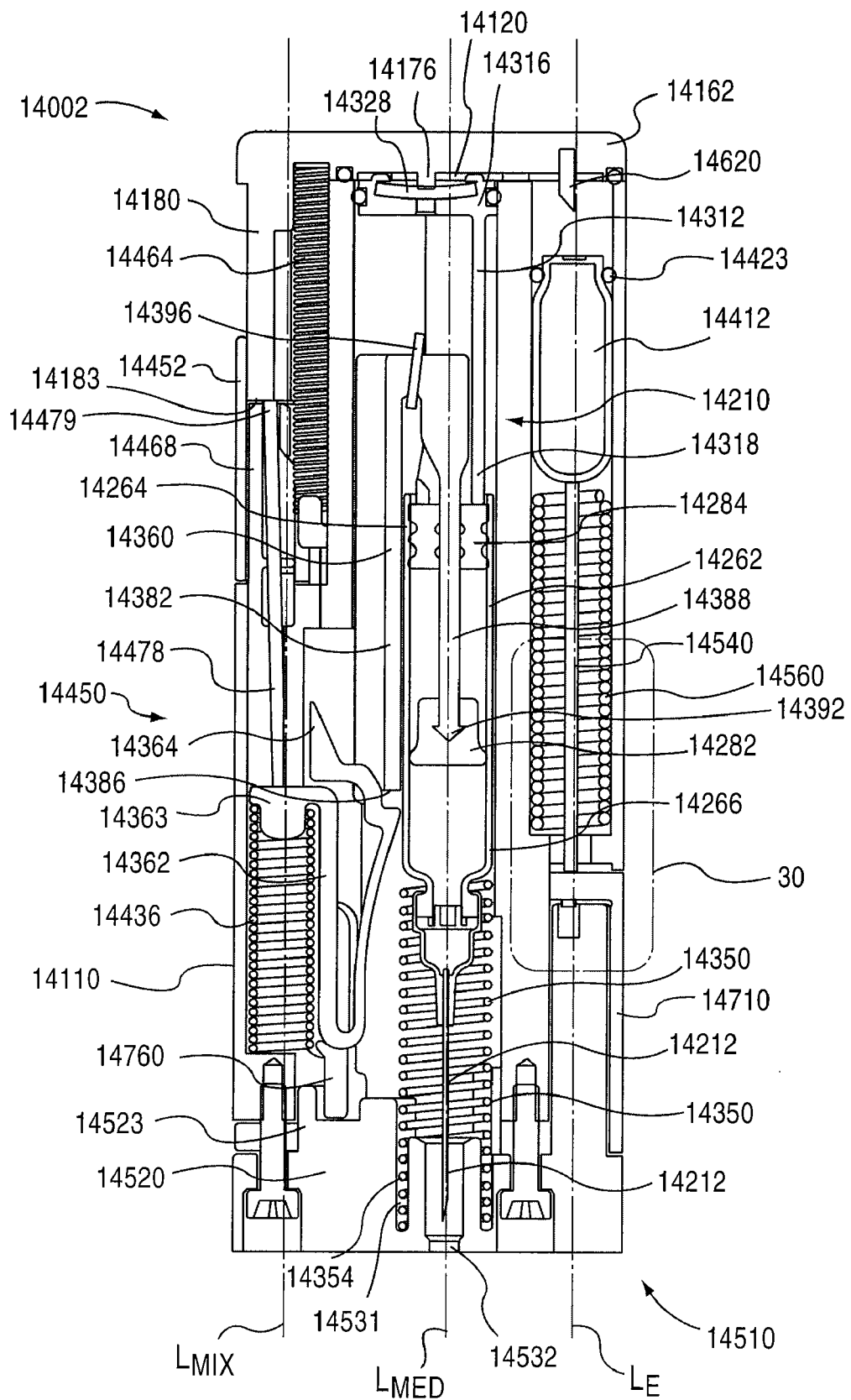
FIG. 16 is a cross-sectional front view of a portion of the auto-injector illustrated in FIG. 14 in a first configuration.

FIG. 15 is a perspective exploded view of the auto-injector 14002 showing the arrangement of the components therein. FIG. 16 is a cross-sectional front view of the auto-injector 14002 in a first configuration (i.e., the initial configuration). The auto-injector 14002 includes a medicament mixer 14360 and a medicament injector 14210, each of which are disposed within the housing 14110. The auto-injector 14002 also includes a mixing actuator 14450 and an injection actuator 14510. As described in more detail herein, the mixing actuator 14450 is configured to release a spring 14436 which is coupled to and causes the medicament mixer 14360 to move within the housing 14110 to mix the contents of the medicament container 14262. The injection actuator 14510 is configured to move a compressed gas container 14412 into engagement with a puncturing element 14620 that is coupled to the proximal cover 14162. In this manner, a compressed gas can be released into a gas chamber 14120 (see FIG. 36) to produce a force necessary to cause the medicament injector 14210 to inject the medicament.

As shown in FIGS. 17-20, the mixing actuator 14450 includes a safety cover 14452, a mixing actuator button 14468 and a retaining rod 14478. The safety cover 14452 is slidably disposed within a pair of grooves 14197 (see FIG. 14) defined by an inner surface 14185 of a slide track 14180 of the proximal cover 14162 and a side surface 14196 of the housing 14110. The safety cover 14452 has a proximal end portion 14453 and a distal end portion 14454. An outer surface 14455 of the safety cover 14452 has a curved shape corresponding to the shape of the housing 14110. An inner surface 14456 of the safety cover 14452 defines an opening 14459 that can receive at least a portion of the slide track 14180. The inner surface 14456 of the safety cover 14452 has a shape that corresponds to a shape of an outer surface 14184 of the slide track 14180 and/or a shape of an outer surface 14472 of the mixing actuator button 14468. The inner surface 14456 of the safety cover 14452 also defines two elongated protrusions 14458 that are received within the grooves 14197 and engage the inner surface 14185 of the slide track 14180 and the side surface 14196 of the housing 14110 to allow the safety cover 14452 to slide longitudinally relative to the slide track 14180, as shown by the arrow AAA in FIGS. 14 and 34, while remaining coupled to the housing 14110.

Figure 20:
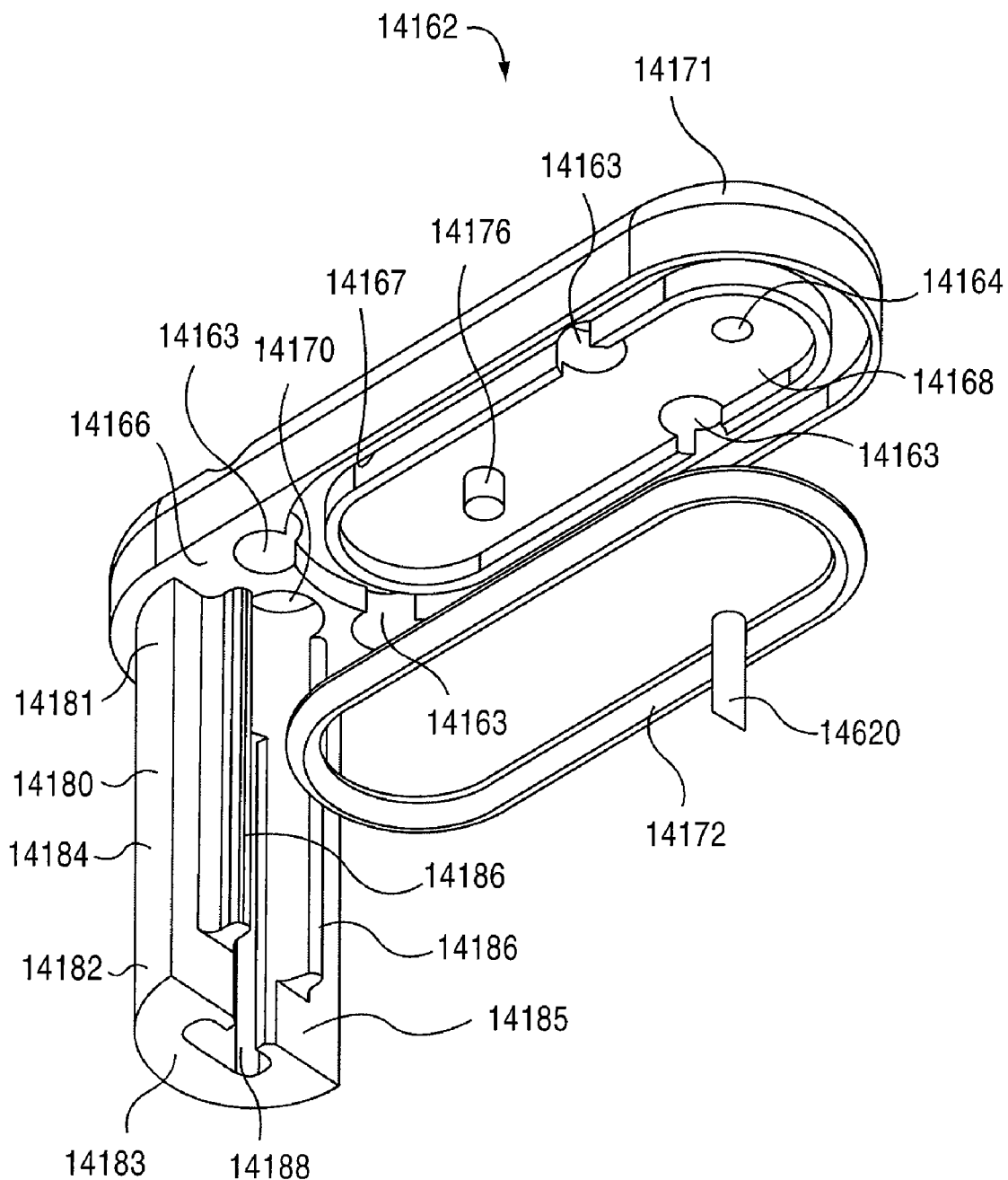
FIG. 20 is a perspective exploded view of a portion of the auto-injector shown in FIG. 14.

The distal end portion 14454 of the safety cover 14452 includes a protrusion 14462 that is received within a distal end 14466 of a safety cover spring 14464. The proximal end 14465 of the safety cover spring 14464 is received within a spring pocket 14170 defined by an interior surface 14166 of the proximal cover 14162, as shown in FIG. 20. In this manner, the safety cover 14452 is biased in a first position (i.e., towards the distal end portion 14114 of the housing 14110) by the safety cover spring 14464, as shown in FIG. 14. When the safety cover 14452 is in its first position, the mixing actuator button 14468 is received within the opening 14459 defined by the inner surface 14456 of the safety cover 14452. In this manner, the mixing actuator button 14468 is covered by the safety cover 14452.

Figure 17:
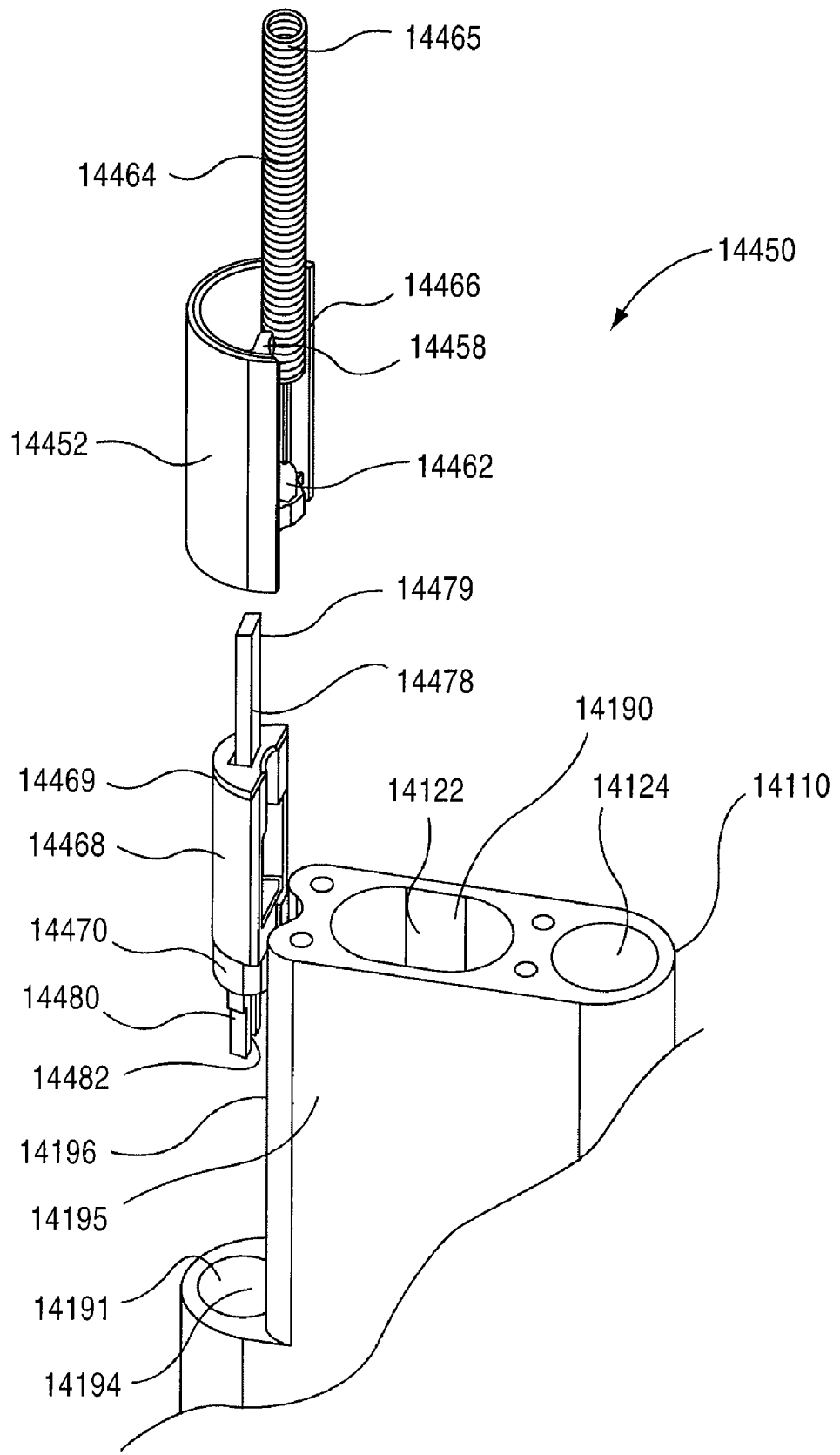
FIG. 17 is a perspective exploded view of a portion of the auto-injector shown in FIG. 14.
Figure 18:
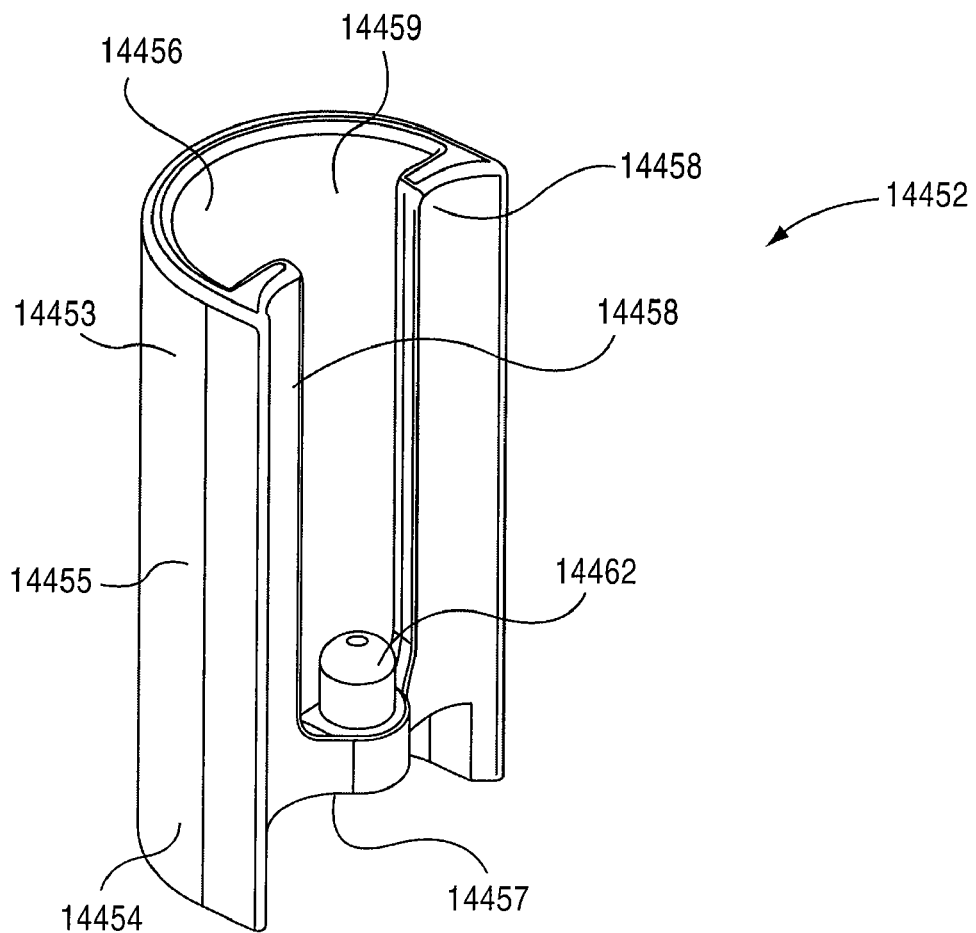
FIG. 18 is a perspective view of a member of the auto-injector illustrated in FIG. 17.
Figure 19:
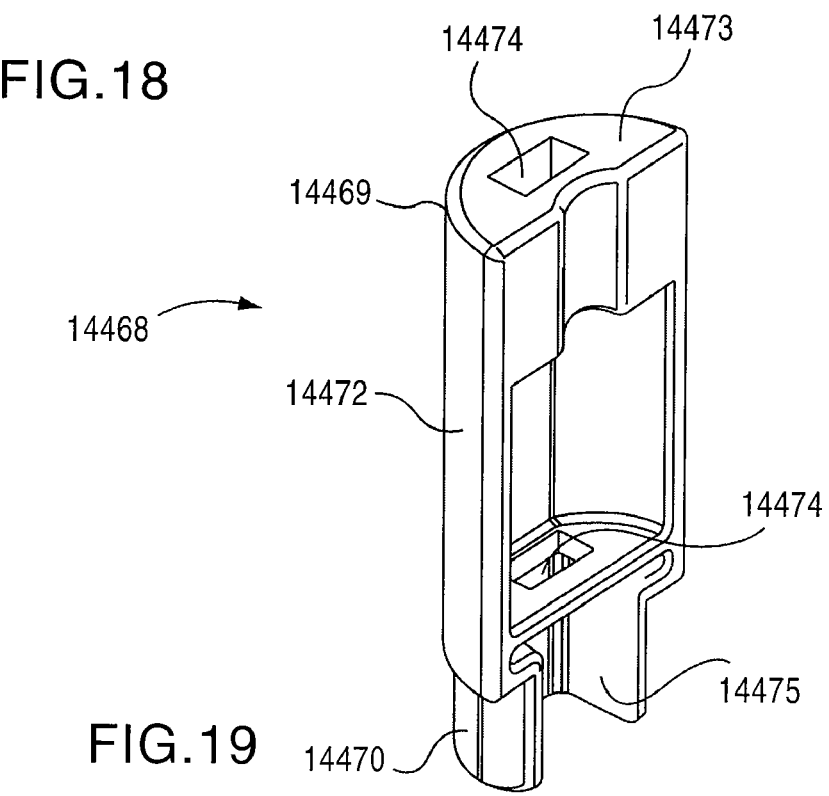
FIG. 19 is a perspective view of a member of the auto-injector illustrated in FIG. 17.

As shown in FIG. 17, the retaining rod 14478 has a proximal end portion 14479 and a distal end portion 14480. The distal end portion 14480 of the retaining rod 14478 defines a slot 14482 that receives a first end portion 14363 of a spring clip 14362 (see FIG. 25). When the auto-injector 14002 is in the first (i.e., the initial) configuration, the proximal end portion 14479 of the retaining rod 14478 is in contact with a distal surface 14183 of the slide track 14180 (see FIGS. 16 and 20). Accordingly, the retaining rod 14478 is maintained in a first (i.e., distal) position, in which the retaining rod 14458 retains the mixing spring 14436 in a compressed configuration. As shown in FIG. 16, when the auto-injector 14002 is in the first configuration, the retaining rod 14478 is angularly offset from a longitudinal axis $L_{MIX}$ of the mixing spring 14436.

The mixing actuator button 14468 has a proximal end portion 14469 and a distal end portion 14470. The distal end portion 14470 of the mixing actuator button 14468 is received within the mixing spring opening 14191 defined by the housing 14110, as shown in FIG. 17. The mixing actuator button 14468 defines two openings 14474 that receive the rod 14478, as shown in FIG. 17. In this manner, when the mixing actuator button 14468 is moved inwardly as shown by arrow BBB in FIG. 34, the retaining rod 14478 moves with the mixing actuator button 14468. Accordingly, as described in more detail herein, when the mixing actuator button 14468 is moved inwardly, the proximal end portion 14479 of the retaining rod can be aligned with groove 14188 defined in the slide track 14180 (see FIG. 20), thereby allowing the mixing spring 14436 to move from its compressed configuration to its expanded configuration along a longitudinal axis $L_{MIX}$ of the mixing spring 14436.

Figure 34:
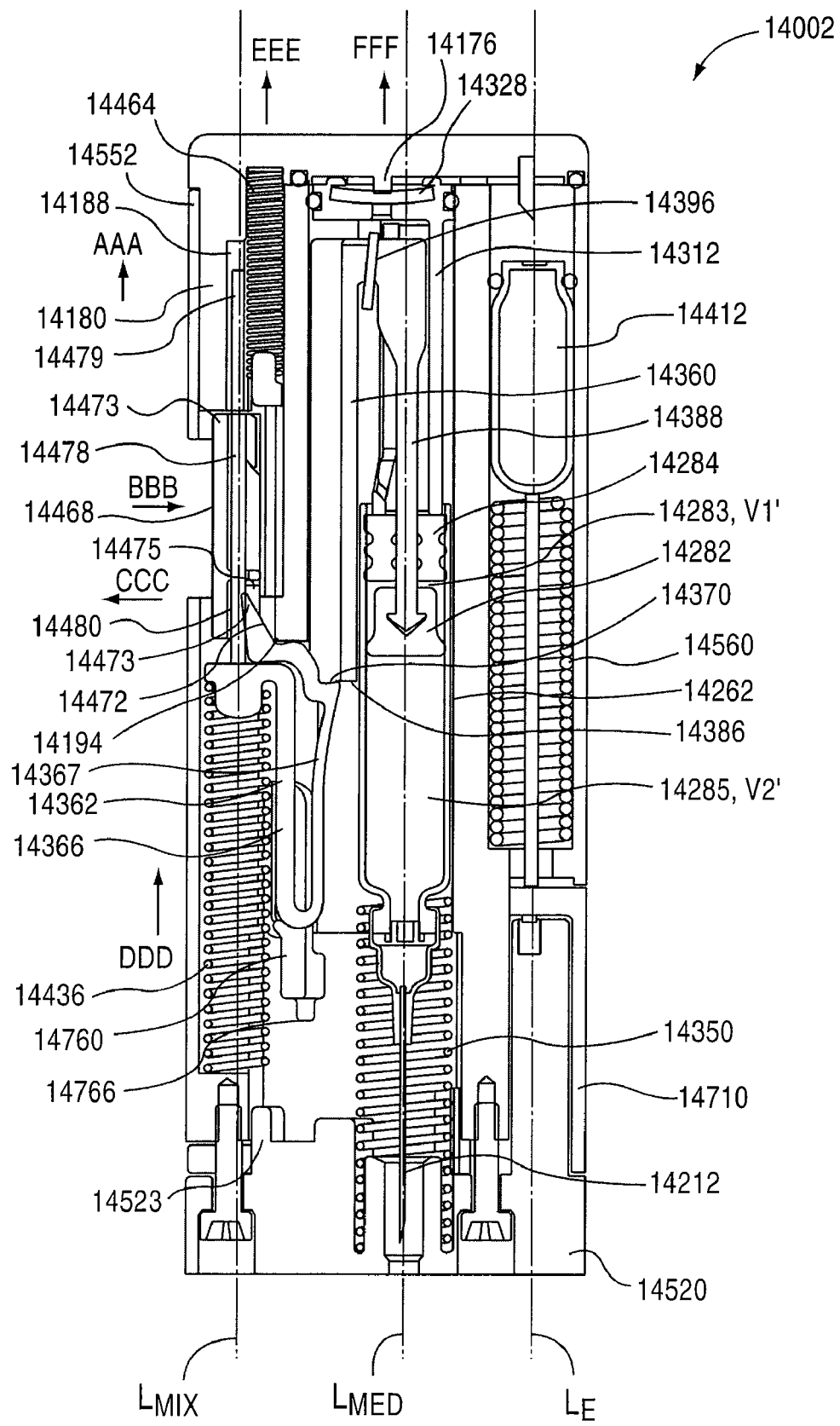
FIGS. 34-38, are cross-sectional front views of a portion of the auto-injector illustrated in FIG. 14 in a second configuration, a third configuration, a fourth configuration, a fifth configuration and a sixth configuration, respectively.

As described in more detail herein, the distal end portion 14470 of the mixing actuator button 14468 defines an opening 14475 that receives a portion of the spring clip 14362 when the mixing actuator 14450 is actuated (see e.g., FIG. 34). Similarly, the proximal end portion 14469 of the mixing actuator button 14468 has a proximal end surface 14473 that engages a distal end surface 14457 of the safety cover 14452 when the mixing actuator 14450 is actuated.

As shown in FIG. 20, the proximal cover 14162 includes a top portion 14171 and the slide track 14180. As previously described, an outer surface 14184 of the slide track 14180 has a shape that corresponds to a shape of the safety cover 14452. An inner surface 14185 of the slide track 14180, together with the side surface 14196 of the housing 14110 define the grooves 14197 within which the safety cover 14452 is slidably disposed. The inner surface 14185 of the slide track 14180 also defines two elongated protrusions 14186 that extend distally from the spring pocket 14170 defined by the interior surface 14166 of the top portion 14171 of the proximal cover 14162. Accordingly, the elongated protrusions 14186 partially enclose the safety cover spring 14464.

The slide track 14180 has a proximal end portion 14181 and a distal end portion 14182. The slide track 14180 defines a longitudinal groove 14188 that extends from the proximal end portion 14181 to the distal end portion 14182. The groove 14188 has a shape corresponding to and slightly larger than the cross-sectional shape of the retaining rod 14478. In this manner, the proximal end portion 14479 of the retaining rod 14478 can be received within the groove 14188.

The distal end portion 14182 of the slide track 14180 also includes a distal surface 14183 adjacent the groove 14188. As described above, when the auto-injector 14002 is in the first configuration, the proximal end portion 14479 of the retaining rod 14478 is in contact with the distal surface 14183 of the slide track 14180.

The top portion 14171 of the proximal cover 14162 includes an interior surface 14166 defining an opening 14164 that receives a puncturing element 14620. The opening 14164 is positioned such that the puncturing element 14620 is aligned with the compressed gas container 14412. In some embodiments, for example, a longitudinal center line of the opening 14164 is coaxial with a longitudinal axis $L_E$ defined by the compressed gas container 14412. Although the opening 14164 is shown as being a blind hole, in other embodiments, the opening 14164 can be a through hole.

The interior surface 14166 also defines a recess 14168. As described in more detail herein, the recess 14168 of the top portion 14171, the surface 14122 defining the injector opening 14190 (see FIG. 17) and the proximal end surface 14322 of the movable member 14312 (see FIG. 32) collectively define a gas chamber 14120. Said another way, the recess 14168 of the proximal cover 14162 defines a portion of a boundary of the gas chamber 14120.

A protrusion 14176 is disposed within the recess 14168. As shown in FIG. 16, when the auto-injector 14002 is in the first configuration, the protrusion 14176 engages a gas release valve 14328 to maintain the gas release valve 14328 in a closed position. Moreover, when the auto-injector 14002 is in the first configuration, the protrusion 14176 prevents the movable member 14312 from moving proximally within the housing 14110.

The interior surface 14166 of the proximal cover 14162 also defines a spring pocket 14170 and an o-ring groove 14167. As described above, the spring pocket 14170 receives the proximal end 14465 of the safety cover spring 14464. An o-ring 14172 is disposed within the o-ring groove 14167 to hermetically seal the gas chamber 14120. The proximal cover 14162 is coupled to the housing 14110 by four mounting screws 14174, as shown in FIG. 15. The top portion 14171 of the proximal cover 14162 defines four mounting holes 14163 that receive the mounting screws 14174.

Although shown and described as being monolithically formed, in some embodiments, the top portion 14171 and the slide track 14180 can be formed separately and joined together to form the proximal cover 14162. Similarly, in some embodiments the proximal cover 14162 and the housing 14110 can be joined together by any suitable means, such as, for example, sonic welding, chemical bonding, laser welding or the like.

Figure 21:
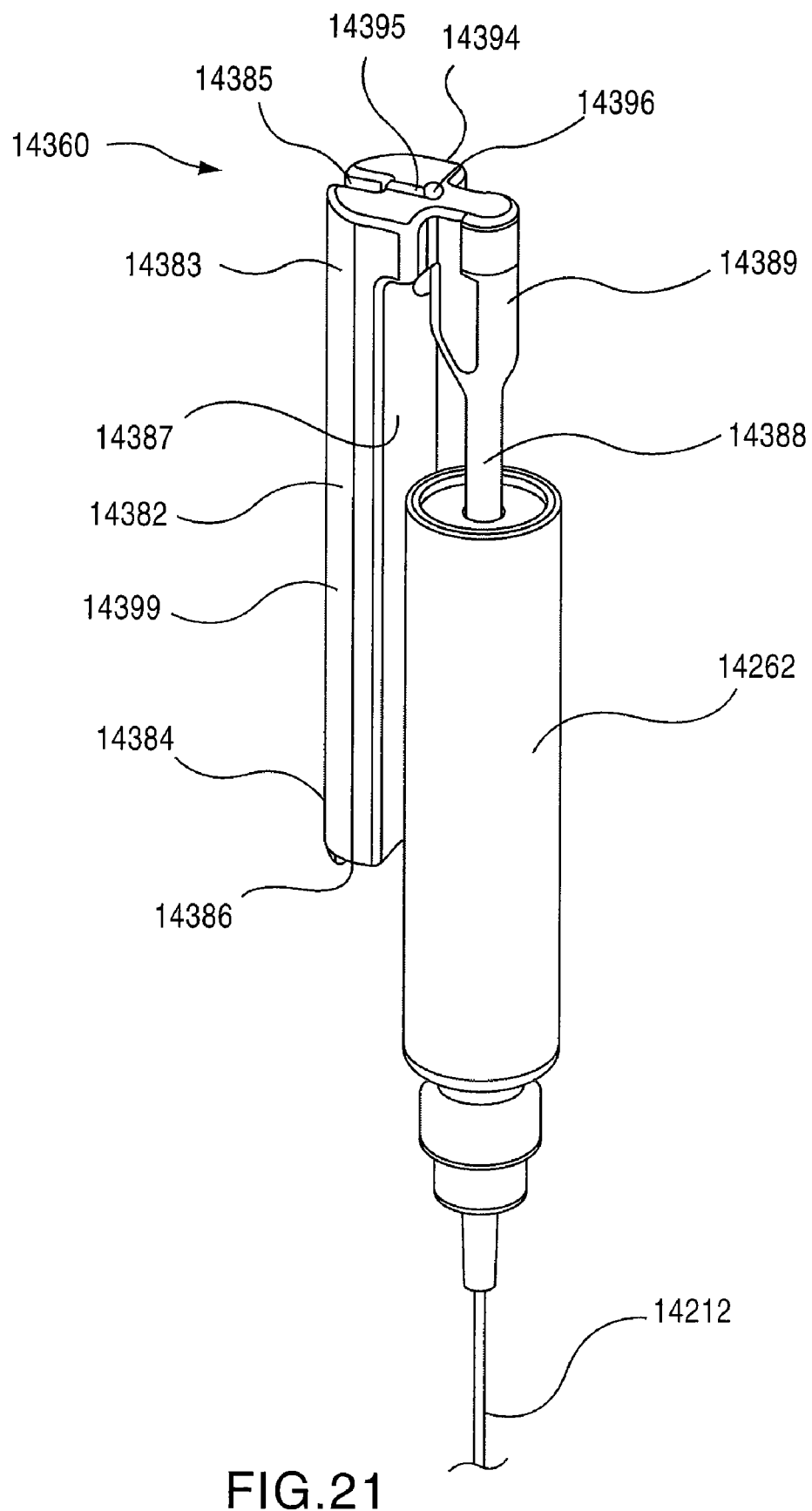
FIG. 21 is a perspective view of a portion of the auto-injector shown in FIG. 14.
Figure 22:
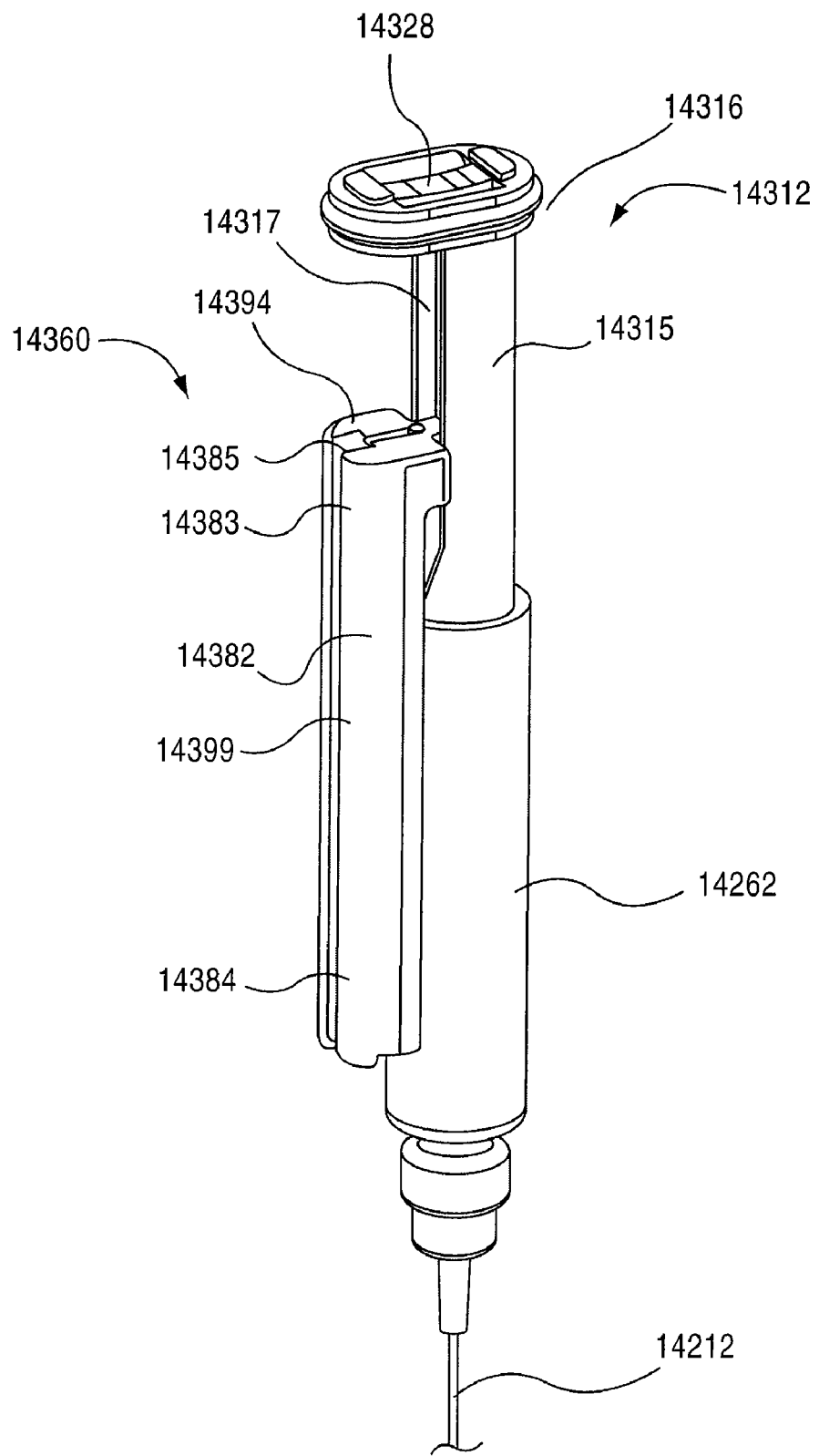
FIG. 22 is a perspective view of a portion of the auto-injector shown in FIG. 14.
Figure 23:
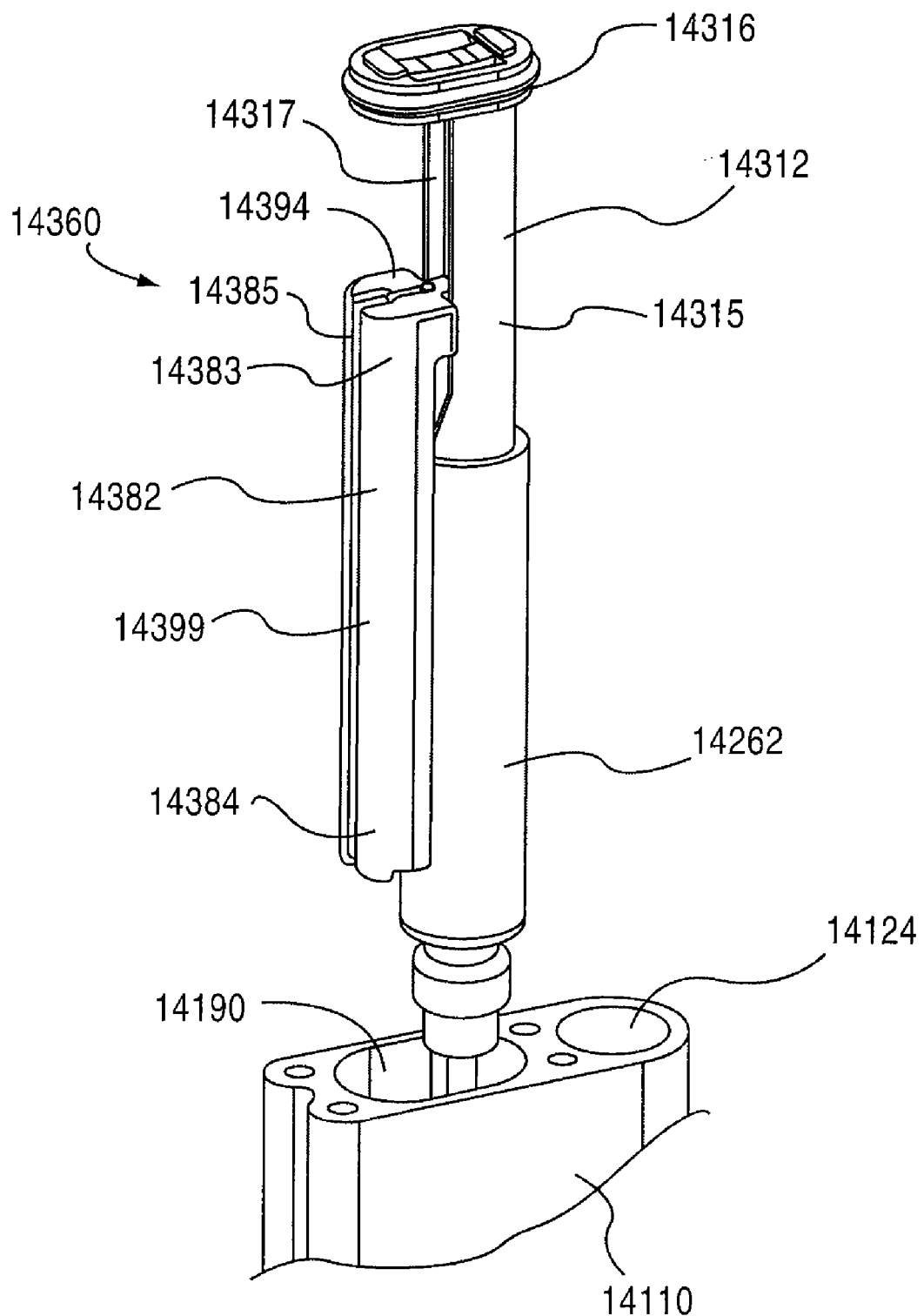
FIG. 23 is a perspective exploded view of a portion of the auto-injector shown in FIG. 14.

As shown in FIGS. 15 and 23, the medicament mixer 14360 is disposed, along with the medicament container 14262 and the movable member 14312, within the medicament injector opening 14190 defined by the housing 14110. As shown in FIGS. 16, 21 and 22, the medicament mixer 14360 includes a spring engagement portion 14382, a plunger engagement portion 14388 and a junction portion 14394. The junction portion 14394 is disposed between the spring engagement portion 14382 and the plunger engagement portion 14388. The spring engagement portion 14382 is disposed outside of and adjacent to the medicament container 14262. Said another way, the spring engagement portion 14382, and therefore the medicament mixer 14260, is offset from a longitudinal axis $L_{MED}$ of the medicament container 14262. Similarly, the medicament mixer 14360 is offset from the longitudinal axis $L_{MIX}$ of the mixing spring 14436.

An inner surface 14387 of the spring engagement portion 14382 has a curved shape that corresponds to the shape of the medicament container 14262. Similarly, an outer surface 14399 of the spring engagement portion 14382 has a curved shape that corresponds to the shape of the injector opening 14190 defined by the housing 14110. In this manner, the medicament mixer 14360 can move longitudinally within the injector opening 14190 while maintaining a constant orientation within the injector opening 14190 (e.g., without tilting and/or binding within the injector opening 14190).

The outer surface 14399 of the spring engagement portion 14382 defines an opening 14385 that extends longitudinally from a proximal end portion 14383 of the spring engagement portion 14382 to a distal end portion 14384 of the spring engagement portion 14382. As described in more detail herein, the opening 14385 is configured to receive a portion of the spring clip 14362 when the movable member 14312 of the medicament injector 14210 is moving distally within the housing 14110 (e.g., during the needle insertion and/or medicament injection process). The distal end portion 14384 of the spring engagement portion 14382 includes an engagement surface 14386 adjacent the opening 14385. As described in more detail herein, the engagement surface 14386 is configured to releasably engage a corresponding engagement surface 14370 of the spring clip 14362.

Figure 24:
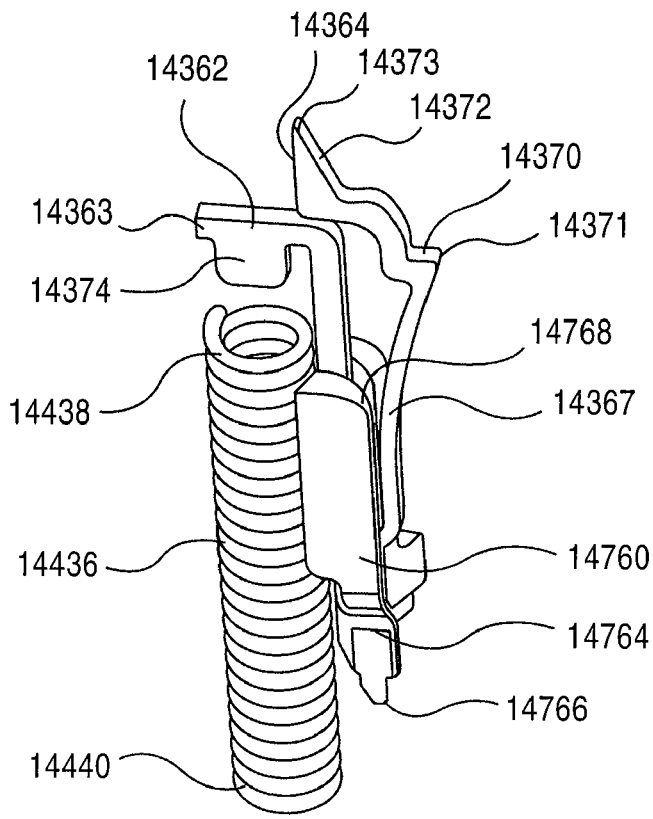
FIG. 24 is a perspective view of a portion of the auto-injector illustrated in FIG. 15.
Figure 25:
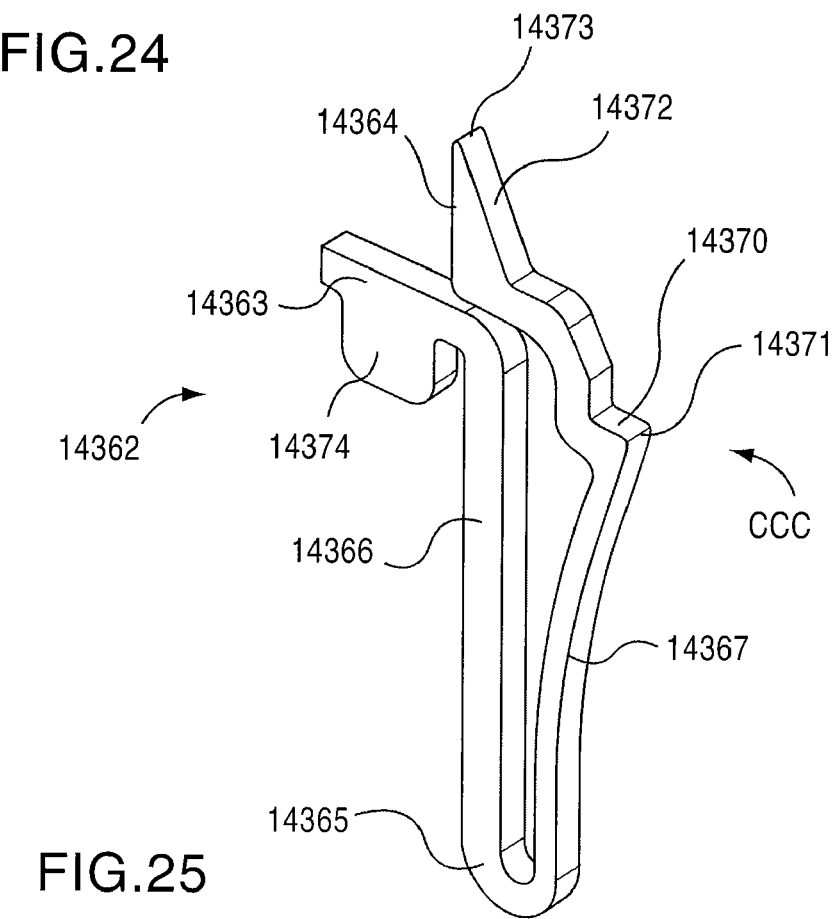
FIG. 25 is a perspective view of a member of the auto-injector illustrated in FIG. 24.

The spring engagement portion 14382 of the medicament mixer 14360 is releasably coupled to the mixing spring 14436 by the spring clip 14362. As shown in FIGS. 24 and 25, the spring clip 14362 includes a first end 14363, a second end 14364 and a U-shaped bend 14365 disposed between the first end 14363 and the second end 14364. Accordingly, the spring clip 14362 includes an outer portion 14366 disposed between the first end 14363 and the U-shaped bend 14365 and an inner portion 14367 disposed between the second end 14364 and the U-shaped bend 14365. The spring clip 14362 is constructed from a resilient material, such as, for example, brass. Accordingly, in use, the inner portion 14367 can elastically deform relative to the outer portion 14366, as indicated by the arrow CCC in FIGS. 25 and 34.

The outer portion 14366 of the spring clip 14362 includes a protrusion 14374 that is received within the proximal end portion 14438 of the mixing spring 14436. As described above, the protrusion 14374 is secured within proximal end portion 14438 of the mixing spring 14436 by the retaining rod 14478. A portion of the outer portion 14366 is received within a retaining groove 14768 defined by a mixing safety lock 14760. The details of the mixing safety lock 14760 are described in more detail herein.

The inner portion 14367 of the spring clip 14362 includes a point 14373 at the second end 14364 thereof. The inner portion 14367 of the spring clip 14362 also includes an angled surface 14372 extending distally from the point 14373, an engagement surface 14370 and a curved surface 14371. In use, the angled surface 14372 engages the surface 14194 of the housing 14110 that defines the mixing spring opening 14191 (see FIG. 17), thereby causing the inner portion 14367 to bend outwardly (as indicated by the arrow CCC in FIGS. 25 and 34). In this manner, the engagement surface 14370 of the spring clip 14362 can be disengaged from the corresponding engagement surface 14386 of the medicament mixer 14360, thereby decoupling the medicament mixer 14360 from the mixing spring 14436.

Figure 31:
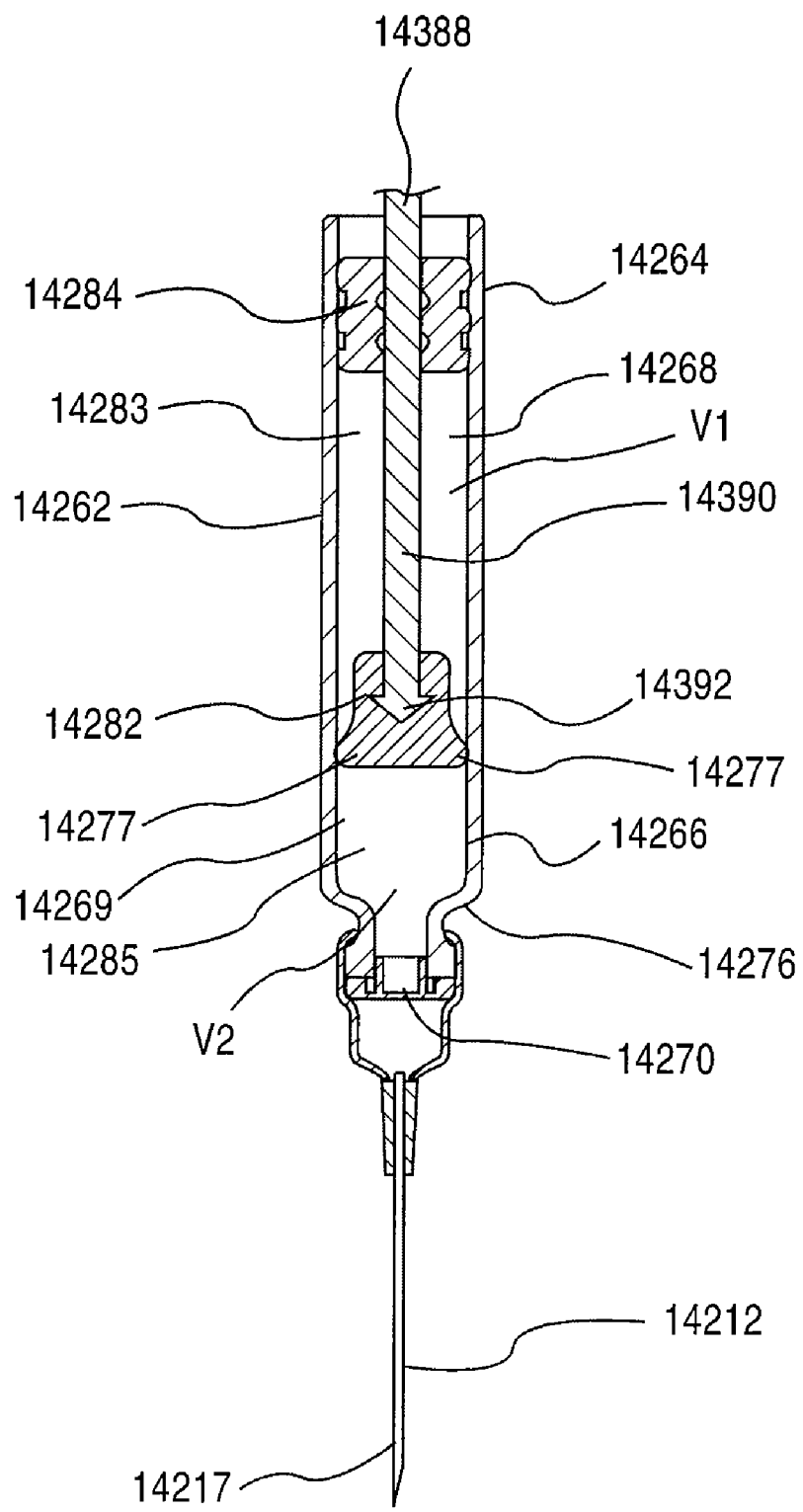
FIG. 31 is a cross-sectional front view of a portion of the auto-injector in FIG. 16.
Figure 32:
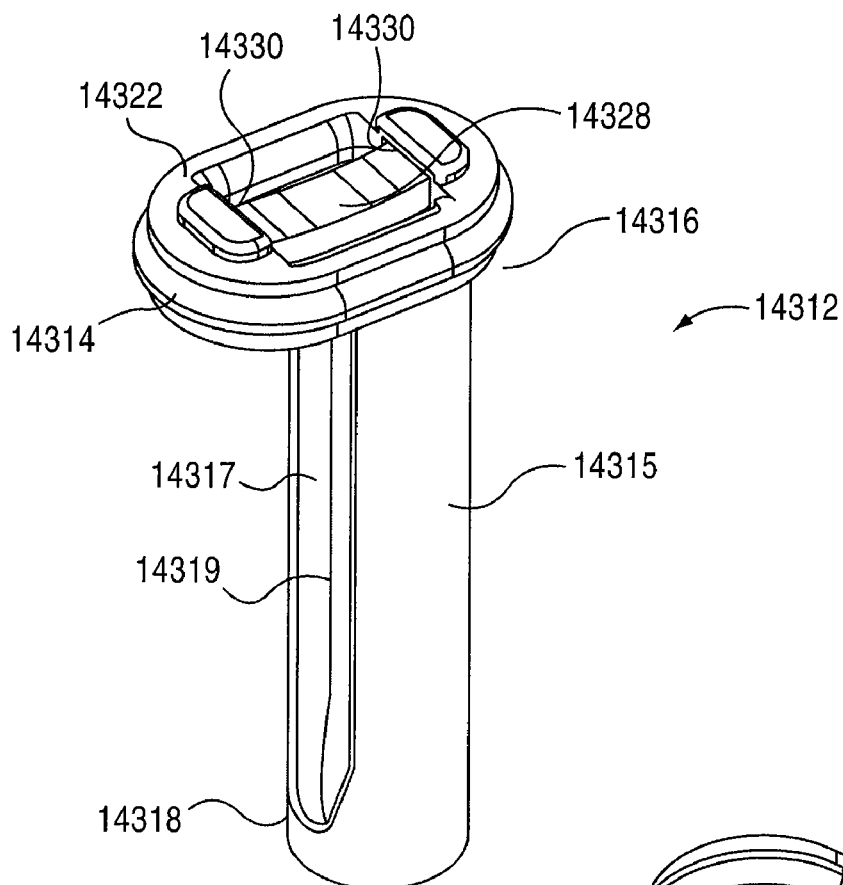
FIGS. 32 and 33 are perspective views of a member of the auto-injector illustrated in FIG. 14.

The plunger engagement portion 14388 of the medicament mixer 14360 has a proximal end portion 14389 and a distal end portion 14390. As shown in FIGS. 21, 22 and 32, the proximal end portion 14389 of the plunger engagement portion 14388 is disposed through an opening 14317 defined by a side wall 14315 of the movable member 14312 and within a lumen 14319 defined by the side wall 14315 of the movable member 14312. The plunger engagement portion 14388 is also disposed through an opening 14321 defined at the distal end portion 14318 of the movable member 14312 such that the distal end portion 14390 of the plunger engagement portion 14388 is disposed through an opening defined by the first plunger 14284 and into the medicament container 14262. As shown in FIG. 31, the second plunger 14282 is coupled to the distal end portion 14390 of the plunger engagement portion 14388 by a plunger coupling 14392.

The junction portion 14394 of the medicament mixer 14360 is disposed between the proximal end portion 14383 of the spring engagement portion 14382 and the proximal end portion 14389 of the plunger engagement portion 14388. The junction portion 14394 defines an opening 14395 within which a pin 14396 is movably disposed. As described in more detail herein, when the injection operation is completed, the pin 14396 actuates a gas release valve 14328 (see e.g., FIGS. 22 and 38) to allow the pressurized gas within the gas chamber 14120 to escape.

This arrangement of the medicament mixer 14360 and the movable member 14312 allows the medicament mixer 14360 to move with the movable member 14312, relative to the movable member 14312 and/or independently from the movable member 14312. This arrangement of the medicament mixer 14360 and the movable member 14312 also allows the medicament mixer 14360 to move in a first direction (e.g., proximally) when the movable member 14312 is moving in a second direction opposite the first direction (e.g., distally). In this manner, as described in more detail herein, the medicament mixer 14360 can combine and/or mix the different medicaments contained in the medicament container 14262 to produce a mixture suitable for delivery via the auto-injector 14002.

When the medicament and/or medicaments contained within the medicament container 14262 are suitably mixed, the auto-injector 14002 can be actuated by the system actuator 14510, which is configured to move the compressed gas container 14412 into engagement with a puncturing element 14620. As shown in FIGS. 15 and 26-30, the injection actuator 14510 include a base 14520, a retaining rod 14540, a spring 14560 and an actuation safety lock 14710.

Prior to actuation, the spring 14560 is disposed about the retaining rod 14540 in a compressed configuration, such that the spring 14560 is retained by a proximal end portion 14542 of the retaining rod 14540 and a retention shoulder 14570 defined within the gas container opening 14124 of the housing 14110. In this manner, the retaining rod 14540 is spring-loaded such that when a distal end portion 14544 of the rod 14540 is decoupled from the retention shoulder 14570, the force of the spring 14560 causes the retaining rod 14540, and therefore the compressed gas container 14412, to move proximally within the housing 14110 along the longitudinal axis $L_E$ of the compressed gas container 14412.

Figure 36:
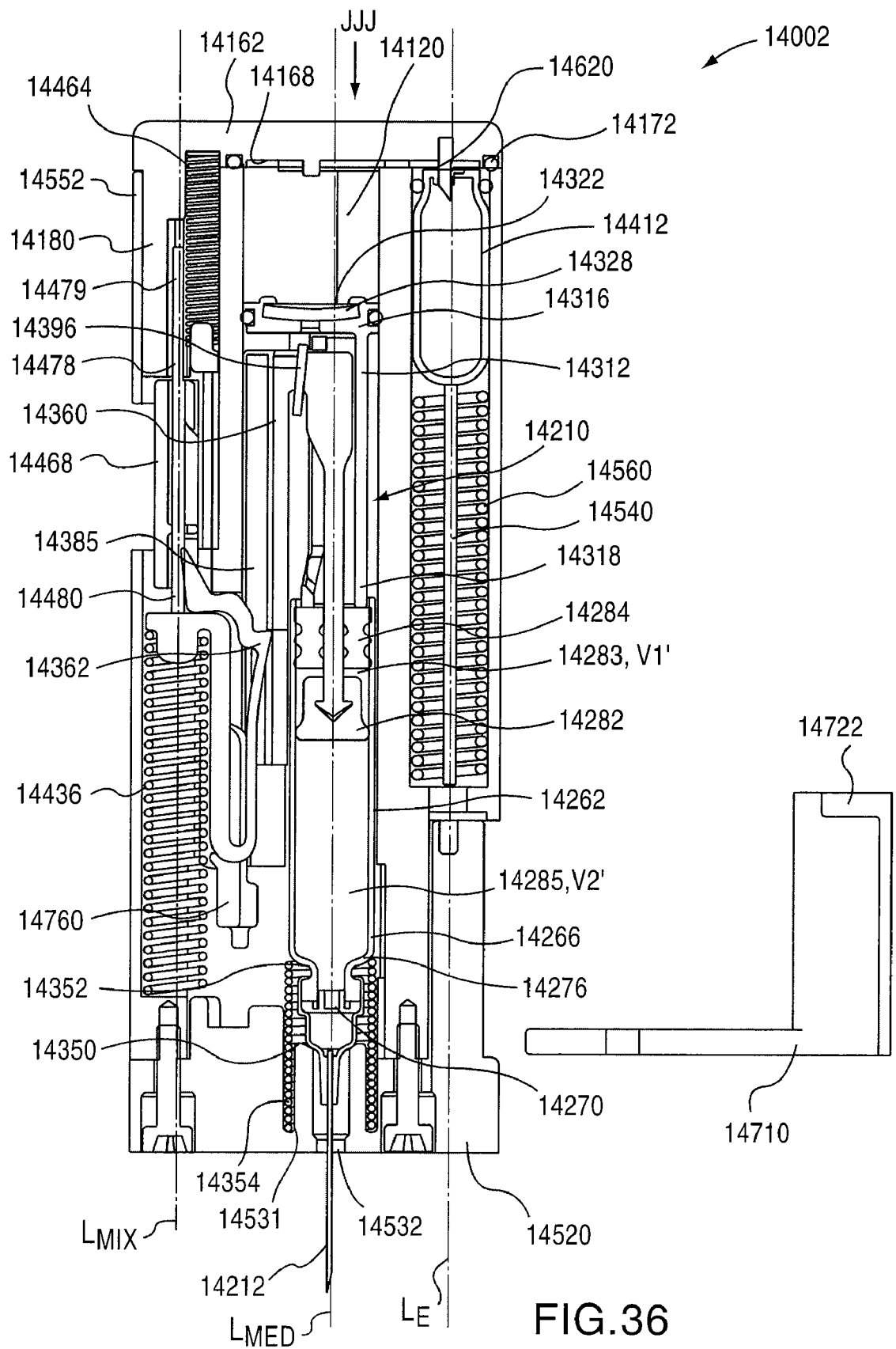

The distal end portion 14544 of the retaining rod 14540 includes two extensions 14552 disposed apart from each other to define an opening 14554 therebetween. Each extension 14552 includes a projection 14548 having a tapered surface 14550 and an engagement surface 14549. As shown in FIG. 30, when the retaining rod 14540 is in its first (or engaged) position, the engagement surfaces 14549 engage a distal surface 14574 of a retention shoulder 14570 defined within the gas container opening 14124 defined by the housing 14110. Accordingly, when the retaining rod 14540 is in its first position, the retaining rod 14540 is prevented from moving proximally along the longitudinal axis $L_E$. As described in more detail herein, when the base 14520 is moved proximally towards the housing 14110 to actuate the auto-injector 14002, the tapered surfaces 14550 of the projections 14548 cooperate with corresponding tapered surfaces 14524 defined by the base 14520 to move the extensions 14552 inwardly towards each other. The inward motion of the extensions 14552 causes the engagement surfaces 14549 to become disengaged from the distal surface 14574 of the retention shoulder 14570, thereby allowing the retaining rod 14540 to move between its first position (FIG. 16) and a second (or actuated) position (FIG. 36).

The proximal end portion 14542 of the retaining rod 14540 includes a retention portion 14545 having a first surface 14547 and a second surface 14546. The first surface 14547 of the retention portion 14545 engages the distal portion 14416 of the compressed gas container 14412. The second surface 14546 of the retention portion 14545 engages a proximal end 14562 of the spring 14560. A distal end 14564 of the spring 14560 engages a proximal surface 14572 of the retention shoulder 14570. In this manner, when the retaining rod 14540 is in its first position, the spring 14560 is compressed between the retention shoulder 14570 and the retention portion 14545 of the retaining rod 14540. Accordingly, when the retaining rod 14540 is disengaged from the retention shoulder 14570, the force imparted by the spring 14560 on the retention portion 14545 of the retaining rod 14540 causes the retaining rod 14540 to move proximally along the longitudinal axis $L_E$ into its second position (see e.g., FIGS. 30 and 35).

As shown in FIG. 27, the base 14520 includes a proximal portion 14521 and a distal portion 14529. The distal portion 14529 of the base 14520 is movably coupled to the distal end portion 14114 of the housing 14110 by two mounting screws 14174, as shown in FIG. 15. The distal portion 14529 of the base 14520 defines two openings 14536 that receive the mounting screws 14174. In this manner, the movement and/or alignment of the base 14520 relative to the housing 14110 is guided by the mounting screws 14174 and the openings 14536.

The distal portion 14529 of the base 14520 also defines a needle opening 14532 and a retraction spring pocket 14531 within the needle opening 14532. When the auto-injector 14002 is in its fourth configuration (see FIG. 36), the needle 14212 extends through the needle opening 14532. As shown in FIG. 16, a distal end 14354 of the retraction spring 14350 is retained within the retraction spring pocket 14531.

The distal portion 14529 of the base 14520 defines a proximally facing projection 14523 that defines a top opening 14523 and two side openings 14525. The top opening 14523 receives a distal end portion 14764 of the mixing safety lock 14760 (see FIG. 24). The two side openings 14525 receive the inwardly facing protrusions 14718 of the actuation safety lock 14710 (see FIG. 27). Accordingly, when the auto-injector is in its first configuration, the protrusions 14766 extending from the distal end portion 14764 of the mixing safety lock 14760 extend within the openings 14719 defined by the inwardly facing protrusions 14718 of the actuation safety lock 14710. This arrangement prevents the actuation safety lock 14710 from being removed when the mixing safety lock 14760 is in its initial position. Said another way, the mixing safety lock 14760 and the actuation safety lock 14710 are cooperatively arranged such that the actuation safety lock 14710 cannot be removed until after the mixing operation is complete.

The proximal portion 14521 of the base 14520 includes two opposing tapered surfaces 14524 (only one of the tapered surfaces is shown in FIG. 27) that define an opening 14522 configured to receive the corresponding tapered surfaces 14550 of the retaining rod 14540 when the base 14520 is moved proximally towards the housing 14110. When the projections 14548 of the retaining rod 14540 are received within the opening 14522, they are moved together, causing the distal end portion 14544 of the rod 14540 to be disengaged from the retention shoulder 14570.

As shown in FIG. 26, the actuation safety lock 14710 has a first end 14712 and a second end 14714. The second end 14714 of the actuation safety lock 14710 includes two extended portions 14716, each of which includes an inwardly facing protrusion 14718 defining an opening 14719. When the actuation safety lock 14710 is in its first (or locked) position, the extended portions 14716 extend around a portion of the base 14520 and/or housing 14110 to space the base 14520 apart from the distal end portion 14114 of the housing 14110. The ends 14721 of the extended portions 14716 are configured slightly wrap around a portion of the housing 14110, the base 14520 and/or the mounting screws 14174 to removably couple the actuation safety lock 14710 to the housing 14110 in its first position. Additionally, the inwardly facing protrusions 14718 extend within the side openings 14525 of the base 14520 to removably couple the actuation safety lock 14710 in its first position. The inwardly facing protrusions 14718 are at an acute angle with respect to the direction of motion of the actuation safety lock, as indicated by arrow GGG in FIG. 35, such that the inwardly facing protrusions 14718 provide resistance to, but do not prevent the removal of the actuation safety lock 14710.

The first end 14712 of the actuation safety lock 14710 includes a locking protrusion 14722 that extends inwardly. As shown in FIG. 30, when the actuation safety lock 14710 is in its first position, the locking protrusion 14722 extends within the opening 14554 between the projections 14548 of the retaining rod 14540 and the opening 14522 defined by the base 14520. In this manner, when the actuation safety lock 14710 is in its first position, the base 14520 cannot be moved proximally to allow the projections 14548 to be received within the opening 14522. The arrangement of the locking protrusion 14722 also prevents the projections 14548 of the retaining rod 14540 from being moved inwardly towards each other. Accordingly, when the actuation safety lock 14710 is in its first position, the auto-injector 14002 cannot be actuated.

The outer surface 14724 of the first end 14712 of the actuation safety lock 14710 includes a series of ridges 14726 to allow the user to more easily grip the actuation safety lock 14710. In some embodiments, the outer surface 14724 of the first end 14712 can include an indicia, such as, for example, a numeral, to instruct the user in operating the auto-injector 14002.

Figure 28:
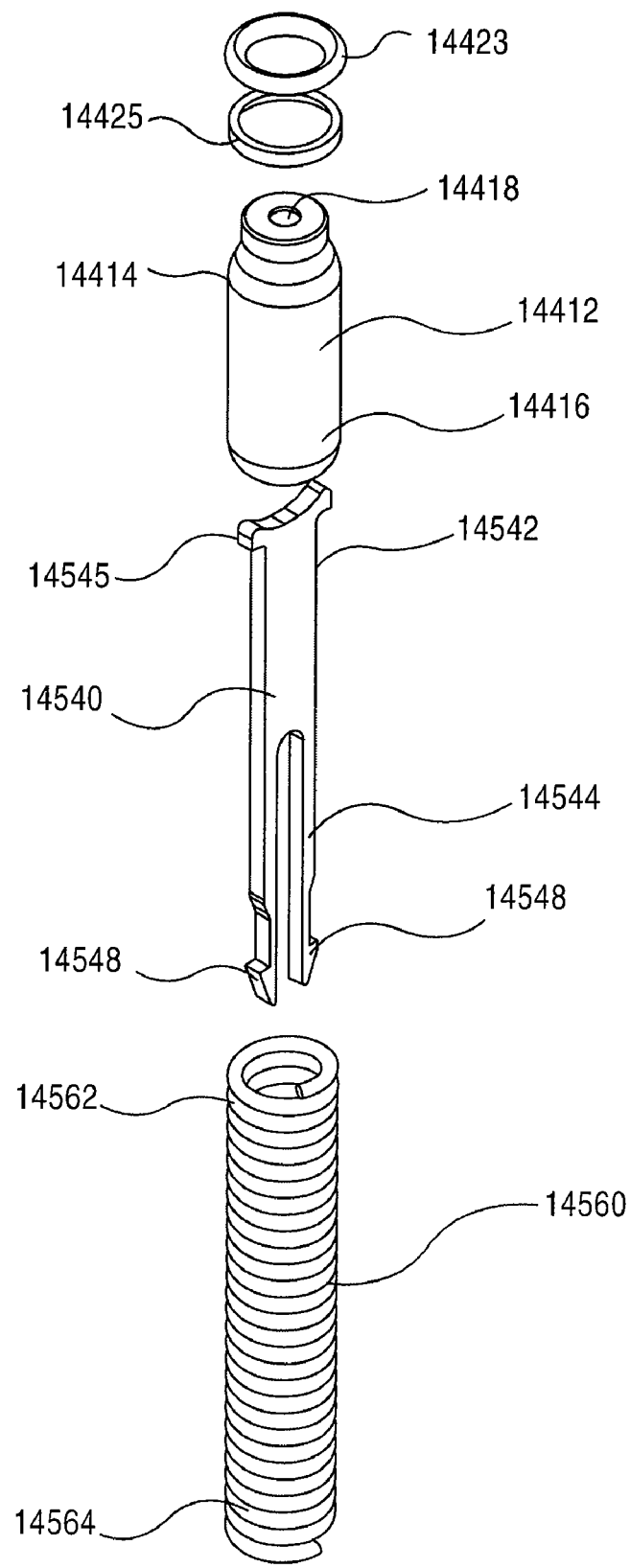
FIG. 28 is a perspective exploded view of a portion of the auto-injector shown in FIG. 14.

As described in more detail herein, upon actuation, the injection actuator 14510 is configured to move the compressed gas container 14412 into engagement with a puncturing element 14620 that is coupled to the proximal cover 14162. As shown in FIGS. 15 and 28, the compressed gas container 14412 is slidably disposed within the gas container opening 14124 of the housing 14110. The compressed gas container 14412 has a distal end portion 14416 and a proximal end portion 14414, and defines a longitudinal axis $L_E$. As described above, the distal end portion 14416 of the compressed gas container 14412 is engaged with the retention portion 14545 of the retention rod 14540.

The proximal end portion 14414 of the compressed gas container 14412 includes a frangible surface 14418. An o-ring 14423 and a spacer 14425 are disposed about the proximal end portion 14414 of the compressed gas container 14412 to hermetically seal the proximal end 14414 of the compressed gas container 14412 within the gas container opening 14124. This arrangement prevents pressurized gas from leaking around the compressed gas container 14412 to an area outside of the gas chamber 14120 after the frangible surface 14418 of the compressed gas container 14412 has been punctured.

The medicament injector 14210 includes a medicament container 14262, a needle 14212 and a movable member 14312. As described in more detail herein, the medicament container 14262 is movably disposed within the medicament injector opening 14190 defined by the housing 14110. The movable member 14312 is also movably disposed within the medicament injector opening 14190 defined by the housing 14110 and is movable relative to the medicament container 14262.

The medicament container 14262 defines a longitudinal axis $L_{MED}$ that is non-coaxial with the longitudinal axis $L_E$ of the compressed gas container 14412 and the longitudinal axis $L_{MIX}$ of the mixing spring 14436. Accordingly, the medicament container 14262, the compressed gas container 14412 and the mixing actuator 14450 are arranged substantially parallel within the housing 14110 such that the housing has a substantially rectangular shape. Moreover, the non-coaxial relationship between the medicament container 14210, the compressed gas container 14412 and the mixing actuator 14450 allows the mixing actuator 14450 and/or the injection actuator 14510 to be actuated by manipulating a portion of the auto-injector 14002 disposed apart from the proximal end portion 14112 of the housing (e.g., the mixing actuator button 14468 disposed on the side portion 14195 of the housing and the base 14520 disposed at the distal end portion 14114 of the housing 14110).

As shown in FIG. 31 the medicament container 14262 includes a proximal end portion 14264 and a distal end portion 14266. The medicament container 14262 includes a first plunger 14284 and a second plunger 14282 disposed distally from the first plunger 14284. The first plunger 14284 and the second plunger 14282 are each movably disposed within the medicament container 14262. A frangible seal 14270 is fixedly disposed within the distal end portion 14266 of the medicament container 14262. The distal end portion 14266 of the medicament container 14262 defines a shoulder portion 14276 which engages a proximal end portion 14352 of the retraction spring 14350.

When the auto-injector 14002 is in the first configuration, as shown in FIG. 31, the first plunger 14284 is disposed in a first position within proximal end portion 14264 of the medicament container 14262. The second plunger 14282 is disposed in a second position distally from the first plunger 14284 such a first medicament containing portion 14283 having a volume V1 is defined between the first plunger 14284 and the second plunger 14282. Similarly, a second medicament containing portion 14285 having a volume V2 is defined between the second plunger 14282 and the frangible seal 14270. In some embodiments, the medicament container 14262 can include a first medicament 14268 (e.g., water) within the first medicament containing portion 14283 and a second medicament 14269 (e.g., a lyophilized powder) within the second medicament containing portion 14285.

The first plunger 14284 forms a fluid-tight seal when disposed within the medicament container 14262. Accordingly, when the first plunger 14284 moves within the medicament container 14262, the portions within the medicament container 14262 distally disposed from the first plunger 14284 (e.g., the first medicament containing portion 14283 and/or the second medicament containing portion 14285) remain fluidically isolated from the portions within the medicament container 14262 proximally disposed from the first plunger 14284.

The second plunger 14282 also forms a fluid-tight seal when stationary within the medicament container 14262. However, when the second plunger 14282 moves within the medicament container 14262, the flexible portions 14277 of the second plunger 14282 can deform thereby allowing the portions within the medicament container 14262 distally disposed from the first plunger 14284 (e.g., the second medicament containing portion 14285) to be in fluid communication with portions within the medicament container 14262 proximally disposed from the first plunger 14284 (e.g., the first medicament containing portion 14283).

The needle 14212 is coupled to the distal end portion 14266 of the medicament container 14262 such that a lumen 14217 defined by the needle 14212 is in fluid communication with a portion of the medicament container disposed distally from the frangible seal 14270. Accordingly, when the frangible seal 14270 is broken, the first medicament containing portion 12283 and/or the second medicament containing portion 12285 are in fluid communication with the lumen 14217 defined by the needle 14212.

Figure 33:
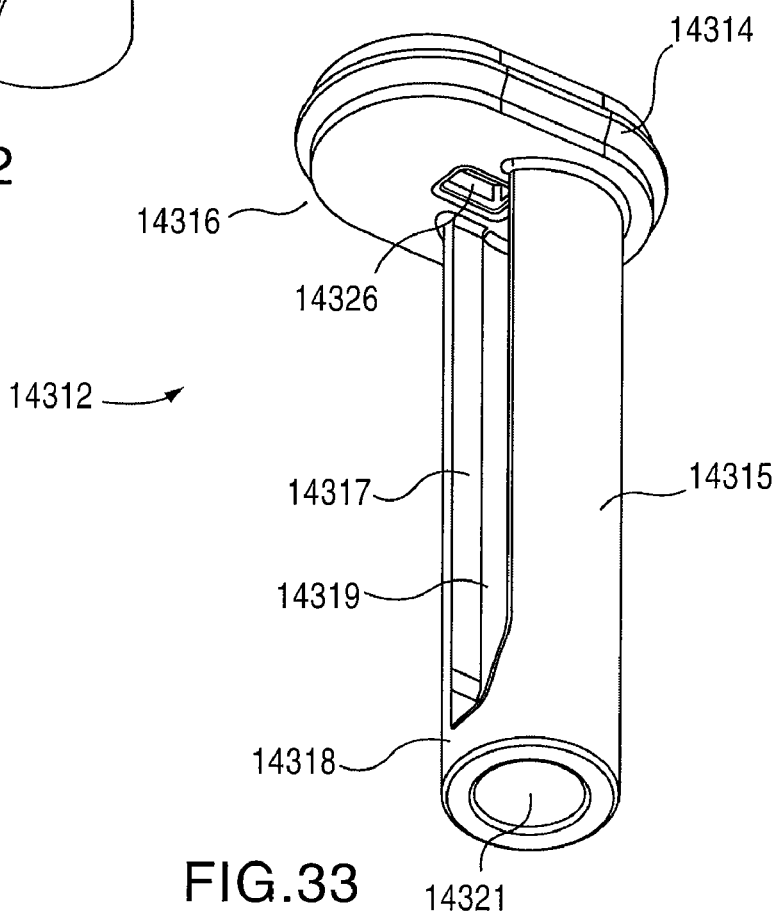

As shown in FIGS. 32 and 33, the movable member 14312 includes a proximal end portion 14316 and a distal end portion 14318. The distal end portion 14318 of the movable member 14312 is disposed within the proximal portion 14264 of the medicament container 14262 such that the distal end portion 14318 engages the first plunger 14284. The movable member 14312 includes a side wall 14315 that extends longitudinally from the proximal end portion 14316 to the distal end portion 14318. The side wall 14315 defines a lumen 14319 and an opening 14317. As described above with reference to FIGS. 22 and 23, the plunger engagement portion 14388 of the medicament mixer 14360 is disposed through the opening 14317 and within the lumen 14319. The distal end portion 14318 of the movable member 14312 also defines an opening 14321 through which the plunger engagement portion 14388 is disposed.

The proximal end portion 14316 of the movable member 14312 includes a surface 14322 that, together with the interior surface 14166 of the proximal cover 14162 (see FIG. 20) and the surface 14122 defining the injector opening 14190 (see FIG. 17), defines a gas chamber 14120. Said another way, the surface 14322 defines a portion of a boundary of the gas chamber 14120.

The proximal end portion 14316 of the movable member 14312 also includes a seal 14314 that engages a portion the inner surface 14122 of the housing 14110 (see FIG. 36) to fluidically isolate the gas chamber 14120. Although the seal 14314 is shown as being an o-ring seal, in some embodiments, the seal need not be a separate component, but can rather be a portion of the proximal end portion 14316 of the movable member 14312.

As shown in FIGS. 32 and 33, the proximal end portion 14316 of the movable member 14312 defines an opening 14326 therethrough which is in fluid communication between the gas chamber 14120 and the interior of the housing 14110 outside the gas chamber 14120. The proximal end portion 14316 further defines two slots 14330 that receive a gas relief valve 14328, which can be, for example, a flexible rubber member. The gas relief valve 14328 is positioned within the slots 14330 and adjacent the opening 14326 to selectively allow fluid communication between the gas chamber 14120 and the area outside the gas chamber 14120 through the opening 14326.

As described in more detail herein, when the injection actuator 14510 is actuated, the movable member 14312 moves towards the distal end portion 14114 of the housing 14110, in response to a force produced by a pressurized gas on the surface 14322 of the movable member 14312. As a result, the medicament container 14262 is moved towards the distal end portion 14114 of the housing 14110, thereby exposing the needle 14212 from the housing 14110. The movable member 14312 then continues to move within the medicament container 14262 break the frangible seal 14270 and expel a medicament from the medicament container 14262 through the needle 14212.

As discussed above, the use and actuation of the auto-injector 14002 includes several discrete operations, as shown in FIGS. 16 and 34-38. Although FIGS. 16 and 34-38 show the same components of the auto-injector 14002, certain reference numerals are omitted in some of the figures for clarity. First, the mixing actuator 14450 is enabled by moving the safety cover 14452 proximally to expose the mixing actuator button 14468 (see FIG. 34). Second, the medicament mixer 14360 is actuated by pressing the mixing actuator button 14468 inward (see FIG. 34). When the medicament mixer 14360 is actuated, the force from the mixing spring 14436 causes the medicament mixer 14360 to move proximally within the housing 14110. Accordingly, the second plunger 14282 moves proximally within the medicament container 14262 to mix and/or combine the first medicament 14268 and the second medicament 14269.

Figure 35:
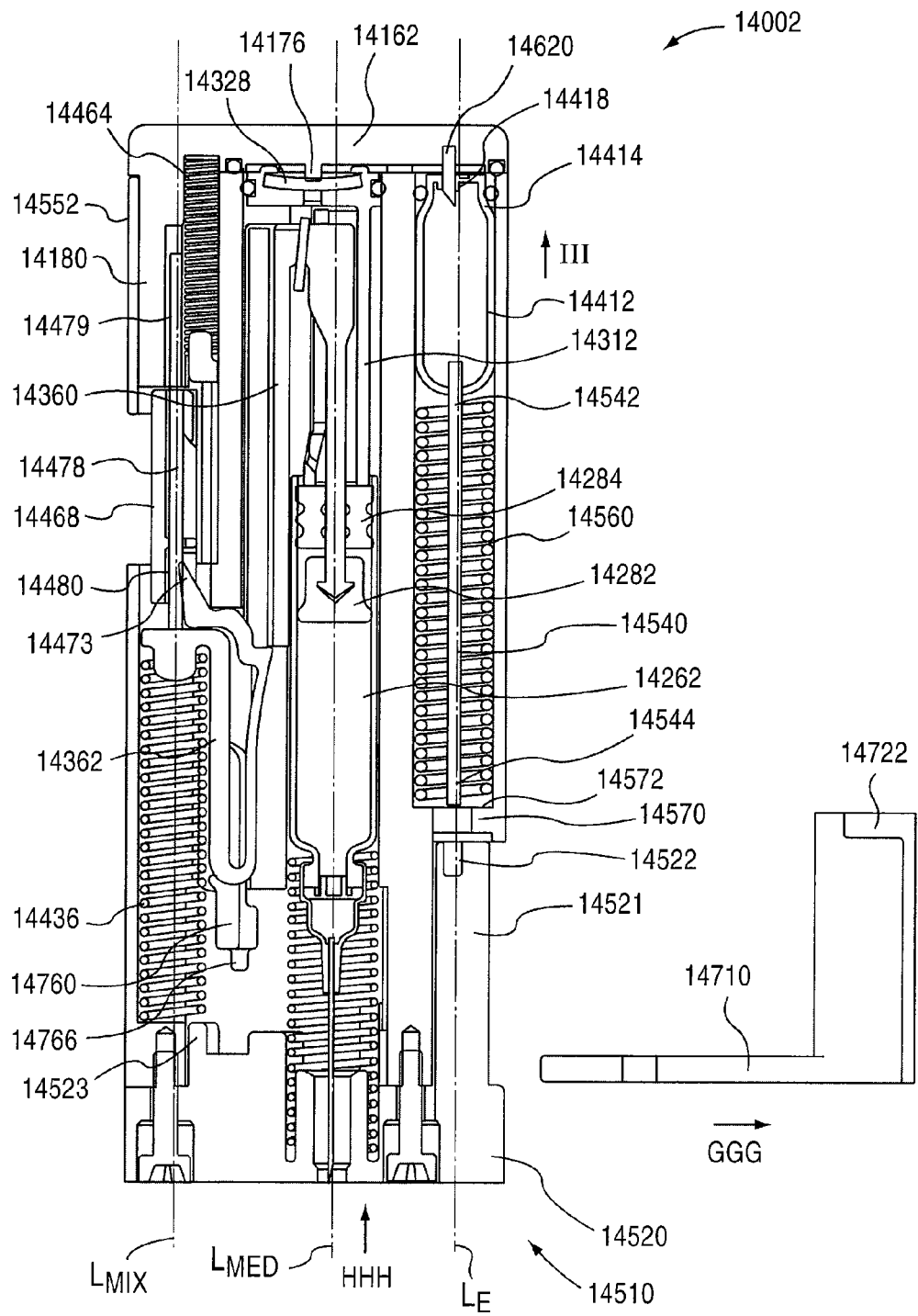

Upon completion of the mixing operation, the medicament injector 14210 is enabled by removing the safety lock 14710 (see FIG. 35). The medicament injector 14210 is then actuated by moving the base 14520 proximally towards the housing 14110. When the medicament injector 14210 is actuated, the compressed gas container 14412 is moved into engagement with the puncturing member 14620, which causes the pressurized gas to be released into the gas chamber 14120 (see FIG. 36). The pressurized gas produces a force that causes the movable member 14312 and the medicament container 14262 to move distally within the housing 14110 to extend the needle 14212 from distal end portion 14114 of the housing 14110 and the base 14520 (see FIG. 36). This operation can be referred to as the "needle insertion" operation. When the medicament container 14262 has completed its distal movement (i.e., the needle insertion operation is complete), the force from the movable member 14312 on the first plunger 14284 causes the frangible seal 14270 to break, thereby placing the second medicament containing portion 14285 in fluid communication with the needle 14212. Accordingly, the movable member 14312 moves within the medicament container 14262, thereby expelling the mixed medicament through the needle 14212 (see FIG. 37). This operation can be referred to as the "injection operation." Upon completion of the injection, the pressurized gas is released from the gas chamber 14120, thereby allowing the medicament container 14262 to be moved proximally within the housing (i.e., retracted, see FIG. 38). A detailed description of each of these operations is provided below.

FIG. 34 shows the auto-injector 14002 in a second configuration, in which the mixing actuator 14450 of the auto-injector 14002 has been actuated. Prior to actuation, the mixing actuator 14450 must first be enabled by moving the safety cover 14452 proximally to expose the mixing actuator button 14468. As described above, the elongated protrusions 14458 of the safety cover 14452 slide within the grooves 14197 (not shown in FIG. 34) such that safety cover 14452 moves in a direction parallel to the longitudinal axis $L_{MIX}$, between a first (i.e., distal) position and a second (i.e., proximal) position, as shown by the arrow AAA in FIG. 34. When the safety cover 14552 is in the second position, a portion of the slide track 14180 is received within the opening 14459 of the safety cover 14452.

The medicament mixer 14360, is then actuated by pushing the mixing actuator button 14468 inwardly between a first position and a second position, as shown by the arrow BBB in FIG. 34. When the mixing actuator button 14468 is in its second position, its proximal end surface 14473 (see FIG. 19) engages the distal end surface 14457 of the safety cover 14452 (not shown in FIG. 34, see e.g. FIG. 18). Accordingly, the safety cover 14452 is prevented from moving distally (i.e., returning to its initial position) by the safety cover spring 14464 after the mixing actuator button 14468 has been pushed. This arrangement allows a user to know whether the auto-injector 14002 has been used via a quick visual examination of the position of the safety cover 14452.

When the mixing actuator button 14468 is moved between its first position and its second position, the retaining rod 14478 moves with the mixing actuator button 14468 from a first (i.e., initial) position to a second (i.e., intermediate) position. Because the distal end portion 14480 of the retaining rod 14478 remains in substantially the same position moving between its first position and its second position, the retaining rod 14478 rotates along an axis substantially normal to the longitudinal axis $L_{MIX}$ of the mixing spring when the retaining rod moving between its first position and its second position.

As shown in FIG. 16, when the retaining rod 14478 is in the first position, the proximal end portion 14479 of the retaining rod 14478 engages the distal surface 14183 of the slide track 14180 such that the mixing spring 14436 is maintained in its compressed configuration. When the retaining rod 14478 is in the second position, the proximal end portion 14479 of the retaining rod 14478 is aligned with the groove 14188 defined in the slide track 14180 (see FIG. 20). Accordingly, the mixing spring 14436 moves from its compressed configuration to its expanded configuration along the longitudinal axis $L_{MIX}$, as shown by the arrow DDD in FIG. 34.

When the mixing spring 14436 moves from its compressed configuration (FIG. 16) to its expanded configuration (FIG. 34), the retaining rod 14478 moves from its second (i.e., intermediate) position to a third (i.e., actuated) position. When the retaining rod 14478 moves from its second to its third position, the proximal end portion 14479 of the retaining rod 14478 is received within the groove 14188 defined in the slide track 14180. Accordingly, the retaining rod 14478 moves proximally along the longitudinal axis $L_{MIX}$, as shown by the arrow EEE in FIG. 34.

Because the medicament mixer 14360 is coupled to the mixing spring 14436 via the spring clip 14362, when the mixing spring 14436 moves from its compressed configuration (FIG. 16) to its expanded configuration (FIG. 34), medicament mixer 14360 moves proximally the within the medicament injector opening 14190, as shown by arrow FFF in FIG. 34. Accordingly, the second plunger 14282 moves proximally within the medicament container 14262 from the second position (see FIG. 31) to a third position. As described above, when second plunger 14282 moves proximally within the medicament container 14262, the flexible portions 14277 of the second plunger 14282 deform to place the first medicament containing portion 14283 in fluid communication with the second medicament containing portion 14285. In this manner, the first medicament 14268 can be mixed with the second medicament 14269 to produce a mixture suitable for delivery via the auto-injector 14002.

When the second plunger 14282 moves proximally within the medicament container 14262 from the second position to the third position, the protrusion 14176 of the proximal cover 14162 (see FIG. 20) remains engaged with the gas relief valve 14328. This arrangement prevents the movable member 14312 (and therefore the first plunger 14284) from moving proximally within the housing 14110. Accordingly, the first plunger 14284 remains in the first position within the medicament container 14262 when the second plunger 14282 moves proximally within the medicament container 14262 from the second position to the third position. Said another way, the second plunger 14282 moves proximally within the medicament container 14262 from the second position to the third position relative to and independently from the movable member 14312 and/or the first plunger 14284.

Although FIG. 34 shows the protrusion 14176 of the proximal cover 14162 being engaged with the gas relief valve 14328 and/or the surface 14322 of the movable member 14312, in some embodiments, the protrusion 14176 can be slightly spaced apart from the gas relief valve 14328 and/or the surface 14322 of the movable member 14312. Such a slight space can result from normal deviations in manufacturing and assembly (i.e., deviations within the manufacturing tolerance of the components). Accordingly, in some embodiments, the first plunger 14284 can move slightly proximally within the medicament container 14262 when the second plunger 14282 moves proximally within the medicament container 14262 from the second position to the third position.

As shown in FIG. 34, when the auto-injector 14002 is in the second configuration, the volume V2' of the second medicament containing portion 14285 is greater than the volume V2 when the medicament container 14262 is in the first configuration (see FIG. 31). Moreover, the total volume of the medicament container 14262 when the auto-injector 14002 is in the first configuration (V1+V2) is the same as the total volume of the medicament container 14262 when the auto-injector 14002 is in the second configuration (V1'+V2'). Although the volume V1' of the first medicament containing portion 14283 is shown as being greater than zero, substantially all of the first medicament 14268 and substantially all of the second medicament 14269 are contained within the second medicament containing portion 14285 when the auto-injector 14002 is in the second configuration.

Although the volume V1' of the first medicament containing portion 14283 is shown as being greater than zero, in some embodiments, the volume V1' of the first medicament containing portion 14283 can be substantially zero when the auto-injector 14002 is in the second configuration. Said another way, in some embodiments, the second plunger 14282 can engage the first plunger 14284 when the auto-injector 14002 is in the second configuration.

After the auto-injector 14002 is in the second configuration (FIG. 34), in some embodiments, the user can enhance the mixing, for example, by shaking the auto-injector 14002. Because the mixing process occurs at a substantially constant volume, the pressure within the first medicament containing portion 14283 and the second medicament containing portion 14285 remains substantially constant throughout the mixing process. Additionally, the medicament mixer 14360 is actuated independently from and using a separate energy storage member (e.g., the mixing spring 14436) from the medicament injector 14210. This arrangement can prevent premature breaking of the frangible seal 14270 which can result in the medicament being injected before the auto-injector 14002 is actuated. Moreover, because the mixing process occurs at a substantially constant volume, in some embodiments, the first medicament containing portion 14283 and/or the second medicament containing portion 14285 can be devoid of a gas (e.g., the first medicament 14268 and/or the second medicament 14269 can be stored in a vacuum).

Similarly, because the first plunger 14284 remains substantially in the first position within the medicament container 14262 when the second plunger 14282 moves proximally within the medicament container 14262 from the second position to the third position, the flow rate of the first medicament 14268 into the second medicament containing portion 14285 is dependent only on the velocity of the second plunger 14282 when moving between the second position and the third position. Accordingly, the flow rate of the first medicament 14268 can be adjusted by adjusting the velocity of the second plunger 14282 when moving between the second position and the third position. For example, in some embodiments, a high flow rate may be desired to enhance mixing (e.g., by creating a turbulent flow of first medicament 14268 into the second medicament containing portion 14285). The velocity of the second plunger 14282 can be adjusted, for example, by increasing the stiffness (i.e., the spring constant) of the mixing spring 14436.

The mixing safety lock 14766 (see FIG. 24) moves proximally within the housing along with the spring clip 14362 when the mixing spring 14436 moves from its compressed configuration (FIG. 16) to its expanded configuration (FIG. 34). Accordingly, when the auto-injector 14002 is in the second configuration (FIG. 34), the protrusions 14766 extending from the distal end portion 14764 of the mixing safety lock 14760 are moved outside of the openings 14719 defined by the inwardly facing protrusions 14718 of the actuation safety lock 14710 (see FIG. 26). In this manner, when the auto-injector 14002 is in the second configuration, the actuation safety lock 14710 can be removed.

During the mixing operation, when the spring clip 14362 moves proximally within the housing 14110 from a first (i.e., distal) position to a second (i.e., proximal) position. When the spring clip 14362 moves from its first position to its second position, the angled surface 14372 of the spring clip 14362 engages the surface 14194 of the housing 14110, thereby causing the inner portion 14367 to bend outwardly, as indicated by the arrow CCC in FIG. 34, when the spring clip 14362 moves proximally. Accordingly, when the spring clip 14362 is in its second position, as shown in FIG. 34, the engagement surface 14370 of the spring clip 14362 is disengaged from the engagement surface 14386 of the medicament mixer 14360, thereby decoupling the medicament mixer 14360 from the mixing spring 14436. The curved surface 14371 (see FIG. 25) of the clip 14362 improves the ease with which the medicament mixer 14360 is decoupled from the mixing spring 14436. Said another way, the curved surface 14371 helps to prevent the engagement surface 14370 of the spring clip 14362 from becoming bound with the engagement surface 14386 of the medicament mixer 14360 (e.g., by burrs, surface roughness or the like). In this manner, when the medicament mixer 14360 moves distally within the housing during the needle insertion and/or injection operations, the mixing spring 14436 is not compressed. Moreover, when the spring clip 14362 is in its second position, the point 14373 at the second end 14364 of the spring clip 14362 is received within the opening 14475 of the mixing actuator button 14468 (see FIG. 19).

FIG. 35 shows the auto-injector 14002 in a third configuration, in which the injection actuator 14510 of the auto-injector 14002 has been actuated. Before the injection actuator 14510 can be actuated, the actuation safety lock 14710 must be removed. As shown by the arrow GGG in FIG. 35, the actuation safety lock 14710 is removed by pulling it substantially normal to the longitudinal axis $L_E$ of the compressed gas container 14412. When the actuation safety lock 14710 is removed, the locking protrusion 14722 (see FIG. 26) is removed from the area between the projections 14548 of the retaining rod 14540 and the opening 14522 defined by the base 14520.

After the actuation safety lock 14710 is removed, the base 14520 can be moved proximally, as shown by the arrow HHH in FIG. 35, to actuate the medicament injector 14210. When the base 14520 is moved proximally towards the housing 14110, the tapered surfaces 14550 of the projections 14548 of the retaining rod 14540 cooperate with the corresponding tapered surfaces 14524 of the base 14520 to move the extensions 14552 of the retaining rod 14540 inwardly towards each other. The inward motion of the extensions 14552 causes the engagement surfaces 14549 to become disengaged from the distal surface 14574 of the retention shoulder 14570 defined within the gas container opening 14124 defined by the housing 14110. Accordingly, the force from the spring 14560 moves the retaining rod 14540 proximally within the housing along the longitudinal axis $L_E$ from a first position (FIG. 34) to a second position (FIG. 35).

Because the retaining rod 14540 is coupled to the compressed gas container 14412, when the rod 14540 is moved from its first (engaged) position to its second (actuated) position, the compressed gas container 14412 is moved proximally within the housing 14110 into engagement with the puncturing element 14620, as shown by the arrow III in FIG. 35. The puncturing element 14620 pierces the frangible surface 14418 at the proximal end portion 14414 of the compressed gas container 14412 thereby releasing a compressed gas into the gas chamber 14120 (see FIG. 36) to actuate the medicament injector 14210.

The pressurized gas released from the compressed gas container 14412 produces a force on the boundary of the gas chamber 14120, including the surface 14322 of the movable member 14312. This force causes the movable member 14312 and the medicament container 14262 move together distally within the injector opening 14190 of the housing 14110, as indicated by the arrow JJJ in FIG. 36, which shows the auto-injector 14002 in a fourth configuration. When in the fourth configuration, the needle 14212 is disposed through the opening 14532 defined by the base 14520 to an area outside of the auto-injector 14002. In this manner, the needle 14212 is automatically inserted into the patient (e.g., the needle insertion operation).

When the auto-injector 14002 is moving between the third configuration (FIG. 35) and the fourth configuration (FIG. 36), the frangible seal 14270 remains intact so that the needle 14212 remains fluidically isolated from the second medicament containing portion 14285 of the medicament container 14210. In this manner, the needle 14212 can be inserted into a patient as the auto-injector 14002 moves between its third configuration and its fourth configuration without injecting the medicament until after insertion is completed. Said another way, the needle insertion operation is distinct from the medicament injection operation.

When the auto-injector 14002 is moving between the third configuration (FIG. 35) and the fourth configuration (FIG. 36), a portion of the spring clip 14362 moves within the longitudinal opening 14385 of the spring engagement portion 14382 of the medicament mixer 14360 (see FIG. 22). In this manner, the medicament injector 14210 can move distally within the housing without compressing the mixing spring 14436.

During the needle insertion operation, the volume V2' of the second medicament containing portion 14285 and the volume V1' of the first medicament containing portion 14283 remain substantially constant. In this manner, the needle insertion operation is independent from the medicament injection operation. As shown in FIG. 36, when the needle insertion operation is completed, the retraction spring 14350 is fully compressed, preventing further distal movement of the medicament container 14262 within the housing 14110. Because the distal motion of the medicament container 14262 is opposed, the force exerted by the pressurized gas on the surface 14322 of the movable member 14312 increases until the frangible seal 14270 breaks, thereby placing the lumen 14217 of the needle 14212 is in fluid communication with the second medicament containing portion 14285 of the medicament container 14262.

Figure 37:
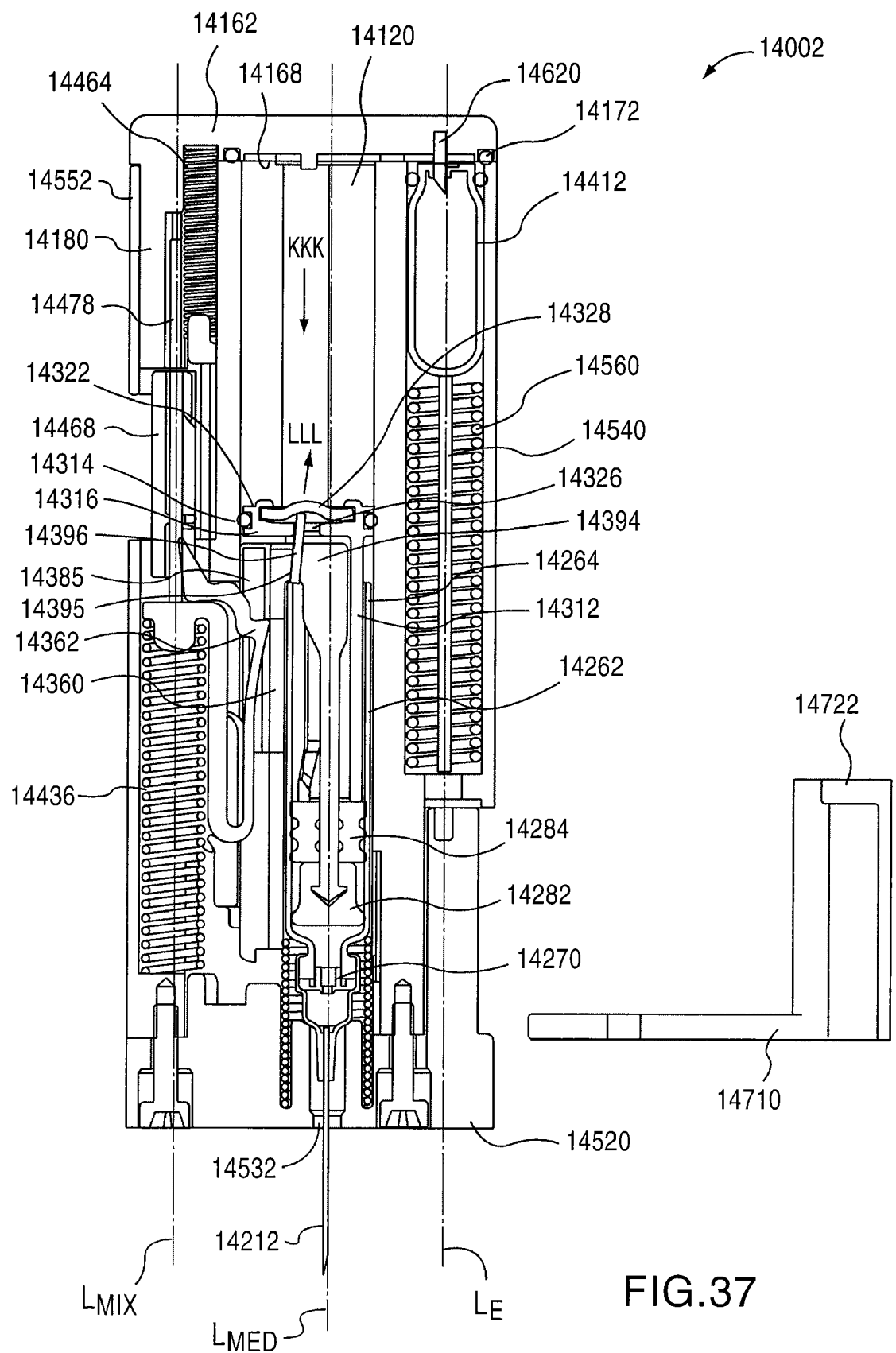

Once the needle 14212 is in fluid communication with the medicament container 14262, the force from the pressurized gas causes the movable member 14312 to collectively move the first plunger 14284 and the second plunger 14282 within the medicament container 14262, as shown by arrow KKK in FIG. 37, thereby expelling the medicament through the needle 14212. The movable member 14312 moves a predetermined distance within the medicament container 14262, at which point the pin 14396 (see FIG. 21) contacts the proximal portion 14264 of the medicament container 14262. The continued distal movement of the movable member 14212 and the medicament mixer 14360 moves the pin 14396 proximally within the opening 14395, as shown by the arrow LLL in FIG. 37. In this manner, the pin 14396 actuates the gas release valve 14328 to allow the pressurized gas within the gas chamber 14120 to escape via the opening 14326 in the movable member 14312.

Figure 38:
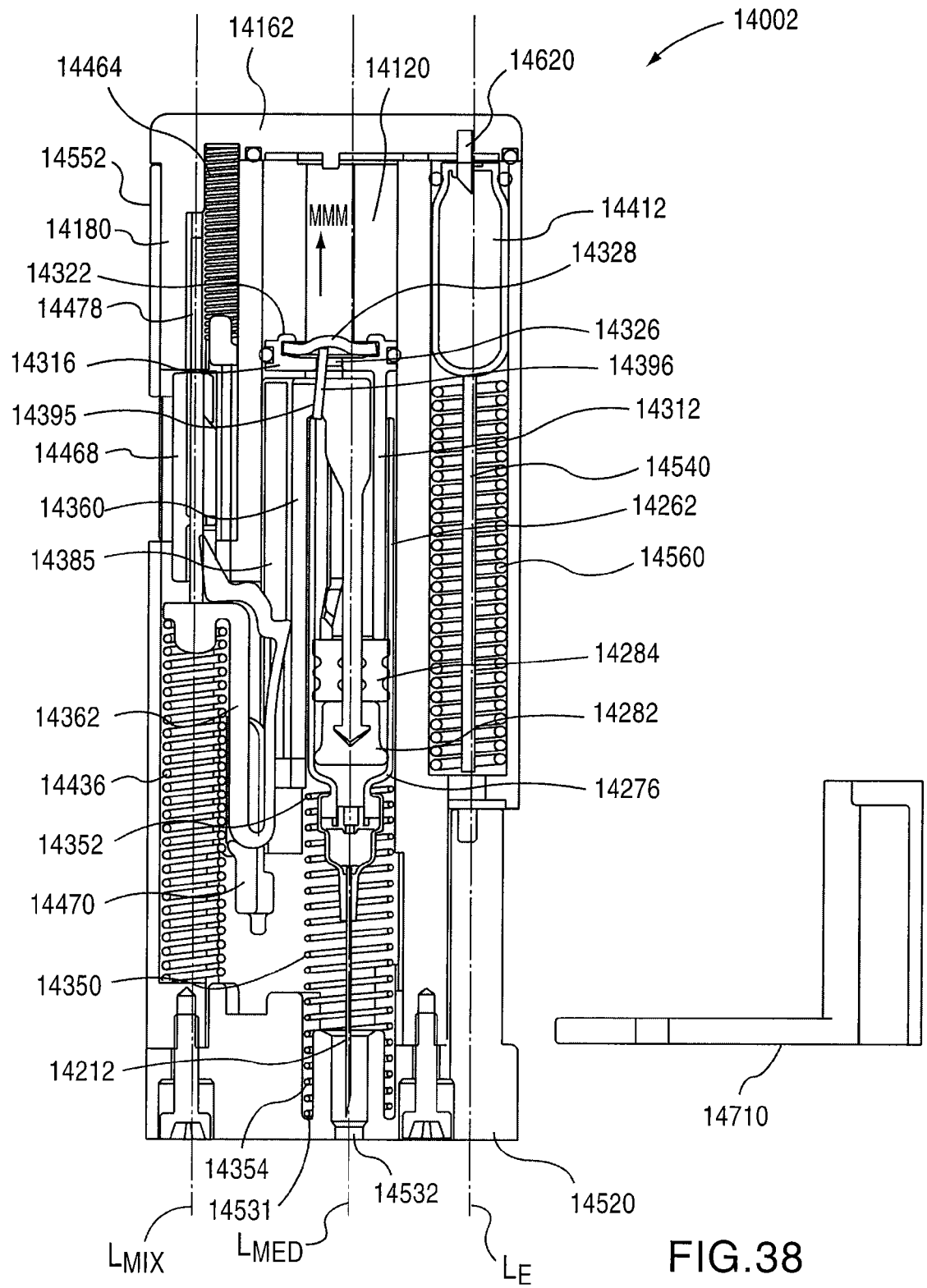

When the pressurized gas flows out of the gas chamber 14120, the pressure exerted on the surface 14322 of the movable member 14312 decreases. Accordingly, the force exerted by the retraction springs 14350 is sufficient to move the medicament injector 14210 proximally within the housing 14110, as shown by arrow MMM, into a sixth (or retracted) configuration as shown in FIG. 38. Because the medicament injector 14210 and the medicament mixer 14360 move proximally together, the pin 14396 remains engaged with the valve 14328 so that the opening 14326 remains in fluid communication with the gas chamber 14120 independent of the position of the movable member 14312. Such an arrangement ensures that all of the pressurized gas flows out of the gas chamber 14120, thereby ensuring that the medicament injector 14210 returns to the sixth configuration and does not oscillate between the sixth configuration and the fifth configuration, which could lead to the needle 14212 not being fully retracted into the housing 14110.

Although the auto-injector 14002 is shown and described as having six different configurations that are different from each other, in some embodiments, certain configuration of an auto-injector can be the same as another configuration. For example, in some embodiments, a "pre-actuation configuration can be the same as a "retracted" configuration. In other embodiments, any of the functions described above can be accomplished when an auto-injector is moved between any number of different configurations.

Figure 39:
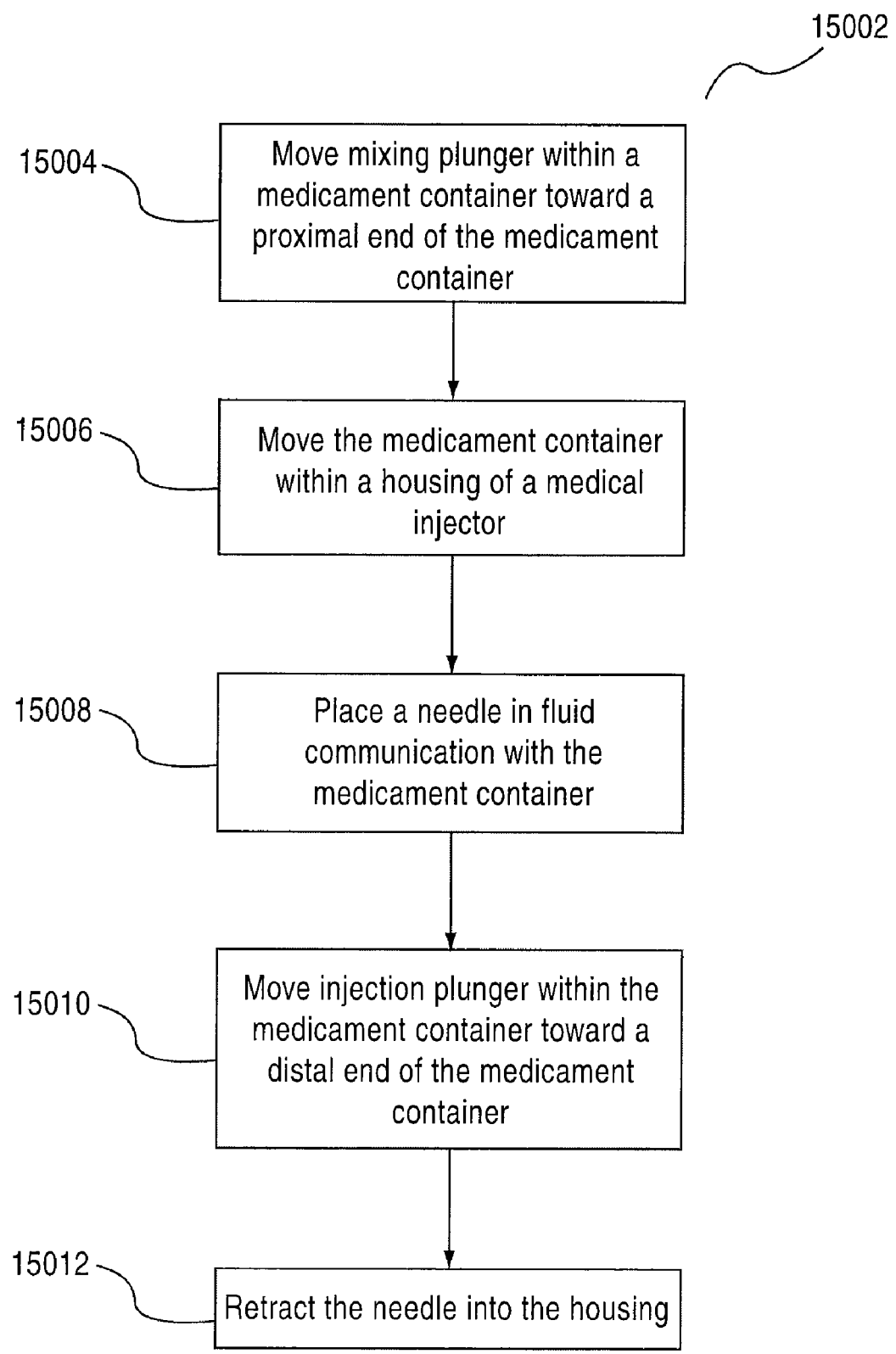
FIG. 39 is a flow chart of a method according to an embodiment of the invention.

FIG. 39 is a flow chart of a method 15002 according to an embodiment of the invention. The method 15002 includes moving a mixing plunger within a medicament container toward a proximal end of the medicament container, 15004. As described above, the medicament container includes the mixing plunger and an injection plunger. The injection plunger is disposed at the proximal end of the medicament container. The mixing plunger is disposed within the medicament container between a distal end of the medicament container and the injection plunger. In this manner, the medicament container can define a first medicament containing portion between the injection plunger and the mixing plunger. Similarly, the medicament container can define a second medicament containing portion between the mixing plunger a distal end portion of the medicament container.

The injection plunger is then moved within the medicament container toward a distal end of the medicament container to expel a medicament contained within the medicament container, 15010.

In some embodiments, the first medicament containing portion and the second medicament containing portion are placed in fluid communication when the mixing plunger moves, thereby allowing a substance contained in the first medicament containing portion to be conveyed into the second medicament containing portion. For example, in some embodiments, the first medicament containing portion can include a liquid substance and the second medicament containing portion can include a solid substance. Accordingly, when the mixing plunger moves, the solid substance can be mixed and/or combined with the liquid substance to produce the medicament.

In some embodiments, the mixing plunger can be moved without moving the injection plunger. In this manner, as described above, the total volume of the first medicament containing portion and the second medicament containing portion remains constant when the mixing plunger is moved. Accordingly, a first medicament and a second medicament can be mixed at a substantially constant volume and/or a substantially constant pressure.

In some embodiments, the mixing plunger can be moved by actuating a first energy storage member, such as, for example, a spring, an electronic actuator, a magnetic actuator, a pneumatic actuator (e.g., a compressed gas container) and/or a hydraulic actuator. Similarly, the injection plunger can be moved by actuating a second energy storage member different than the first energy storage member.

In some embodiments, the method 15002 can optionally include moving the medicament container within a housing of a medical injector, 15006. In this manner, as described above, a needle can be disposed from a distal end of the housing. Similarly, in some embodiments, the method 15002 can optionally include placing the needle in fluid communication with the medicament container, 15008. In this manner, the mixing operation (e.g., operation 15004) and the insertion operation (e.g., operation 15006) can be done independently from the injection operation (15010).

In some embodiments, the method 15002 can optionally include retracting the needle into the housing, 15012.

Figure 40:
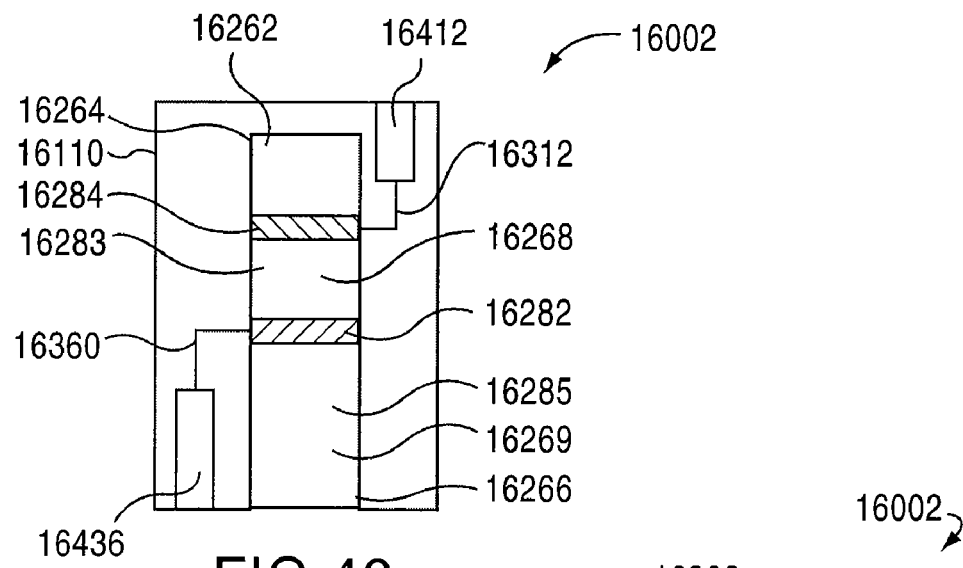
FIGS. 40-42 are schematic illustrations of a medical device according to an embodiment of the invention in a first configuration, a second configuration, and a third configuration, respectively.
Figure 41:
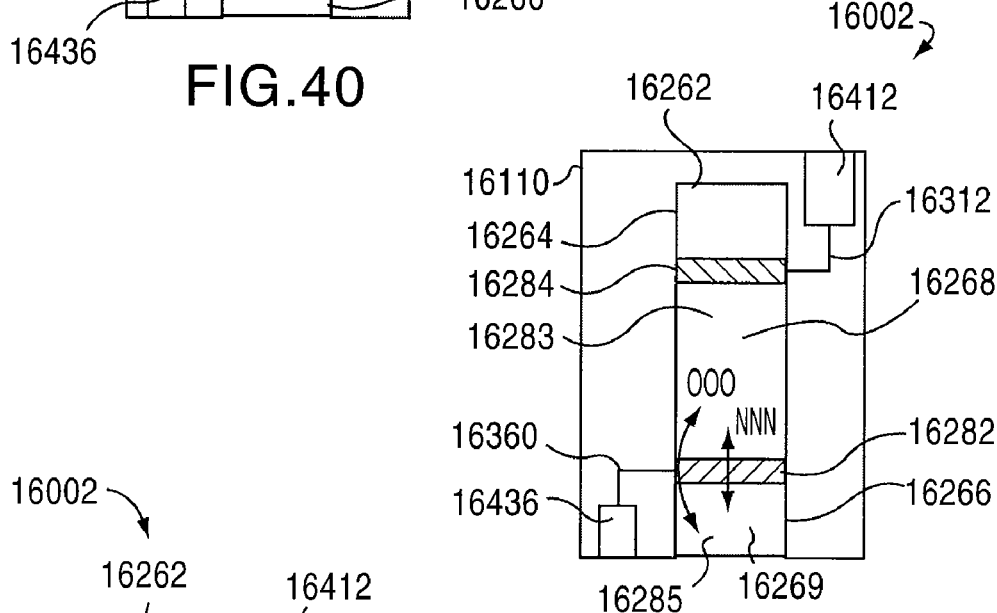
Figure 42:
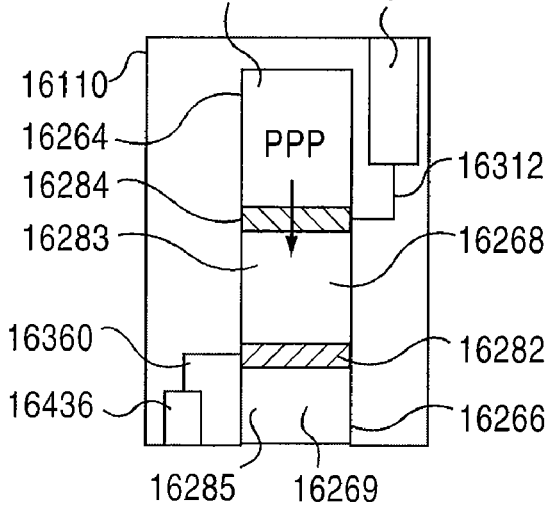

Although the auto-injectors are shown and described above as including a mixing plunger configured to move proximally within a medicament container, in some embodiments, an auto-injector can include a mixing plunger configured to move either proximally or distally within a medicament container. For example, FIGS. 40-42 are schematic illustrations of a medical device 16002 according to an embodiment of the invention in a first configuration, a second configuration and a third configuration, respectively. The medical device 16002 can be any suitable device for delivering a medicament into a body, such as for example, a syringe, a medical injector, an auto-injector or the like. The medical device 16002 includes a housing 16110 that contains a medicament container 16262, a first energy storage member 16412 and a second energy storage member 16436.

The medicament container 16262 has a proximal end portion 16264 and a distal end portion 16266. The medicament container 16262 includes a first plunger 16284 and a second plunger 16282. As shown in FIG. 40, when the medical device 16002 is in the first configuration, the first plunger 16284 is disposed in a first position within the medicament container 16262. The second plunger 16282 is disposed in a second position within the medicament container 16262. The second position is spaced apart from the first position such that a first medicament containing portion 16283 is defined between the first plunger 16284 and the second plunger 16282. Similarly, a second medicament containing portion 16285 is defined between the second plunger 16282 and the distal end portion 16266 of the medicament container 16262. As described above, in some embodiments, the first medicament containing portion 16283 can include a liquid medicament 16268, such as a water, and the second medicament containing portion 16285 can include a second medicament 16269, such as a lyophilized powder.

The first energy storage member 16412 is operatively coupled to the first plunger 16284 by a first movable member 16312. Although the first movable member 16312 is shown as being physically coupled to the first energy storage member 16412 and the first plunger 16284, in some embodiments, the first movable member 16312 can be electronically coupled to the first energy storage member 16412 and/or the first plunger 16284. Similarly, the second energy storage member 16436 is operatively coupled to the second plunger 16282 by a second movable member 16360. Although the second movable member 16360 is shown as being physically coupled to the second energy storage member 16436 and the second plunger 16282, in some embodiments, the second movable member 16360 can be electronically coupled to the second energy storage member 16436 and/or the second plunger 16282.

The first energy storage member 16412 and/or the second energy storage member 16436 can be any suitable energy storage member configured to produce a force when moved between a first configuration (FIG. 40) and a second configuration (FIGS. 41 and 42). The first energy storage member 16412 and/or the second energy storage member 16436 can be, for example, a mechanical energy storage member (e.g., a spring), an electrical energy storage member (e.g., a battery or a capacitor), a chemical energy storage member (e.g., a container containing two substances that can react to produce energy), a magnetic energy storage member or the like. In some embodiments, the first energy storage member 16412 can be of a different type than the second energy storage member 16436.

As shown in FIG. 41, when the medical device 16002 is in the second configuration, the second energy storage member 16436 is in a second configuration. Accordingly, the second energy storage member 16436 produces a force to move the second plunger 16282 within the medicament container 16262, as shown by the arrow NNN in FIG. 41. When the medical device 16002 is in the second configuration, the second plunger 16282 can be moved either proximally or distally within the medicament container.

In some embodiments, the first medicament containing portion 16283 can be fluidically isolated from the second medicament containing portion 16285 when the medical device 16002 is in the first configuration. The first medicament containing portion 16283 can be in fluid communication with the second medicament containing portion 16285 when the medical device 16002 is moving from the first configuration to the second configuration, as shown by the arrow OOO in FIG. 41. Accordingly, as described above, the medical device 16002 can combine and/or mix the first medicament 16268 with the second medicament 16269 contained in the second medicament containing portion 16285 to produce a mixture suitable for delivery via the medical device 16002.

As shown in FIG. 42, when the medical device 16002 is in the third configuration, the first energy storage member 16412 is in a second configuration. Accordingly, the first energy storage member 16412 produces a force to move the first plunger 16284 within the medicament container 16262, as shown by the arrow PPP in FIG. 42. As shown in FIG. 42, when the medical device 16002 is in the third configuration, the first plunger 16284 and the second plunger 16282 are collectively moved distally within the medicament container 16262. In this manner, the first medicament 16268 and the second medicament 16269 can be collectively expelled from the distal end portion 16266 of the medicament container 16262 (e.g., via a needle).

Because the auto-injector 16002 includes a first energy storage member 16412 and a second energy storage member 16436 different from the first energy storage member, the first plunger 16284 and the second plunger 16282 can be moved independently from each other. For example, in some embodiments, the second plunger 16282 can be repeatedly moved proximally and distally within the medicament container 16262 to mix the first medicament 16268 and the second medicament 16269. In other embodiments, the second plunger 16282 can move in a first direction (e.g., proximally) when the first plunger 16284 is moving in a second direction opposite the first direction (e.g., distally) to mix the first medicament 16268 and the second medicament 16269. This arrangement ensures that the mixing operation and the injection operations are distinct from each other.

Figure 43:
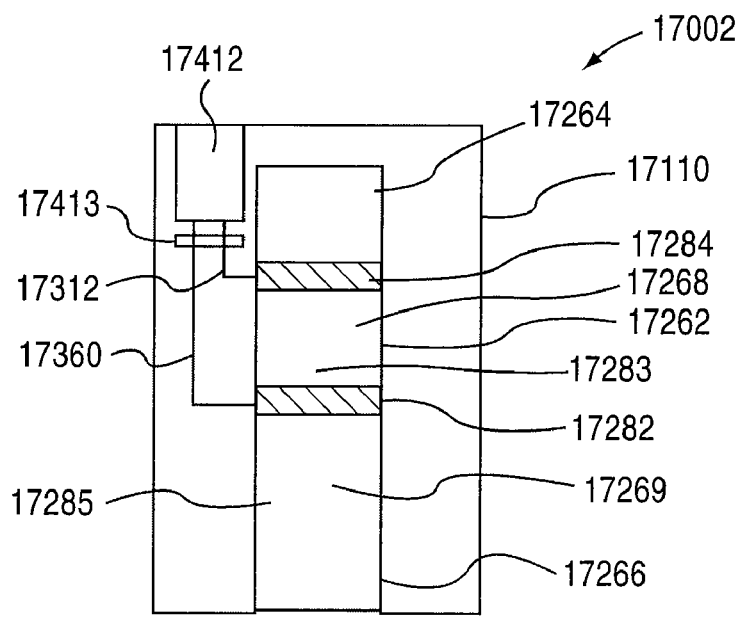
FIG. 43 is a schematic illustration of a medical device according to an embodiment of the invention.

Although the auto-injectors are shown and described above as including different energy storage members, in some embodiments an auto-injector can include one energy storage member configured to independently move a mixing plunger and an injection plunger. For example, FIG. 43 is a schematic illustration of a medical device 17002 according to an embodiment of the invention. The medical device 17002 includes a housing 17110 that contains a medicament container 17262 and an energy storage member 17412, such as, for example, a compressed gas container.

The medicament container 17262 has a proximal end portion 17264 and a distal end portion 17266. The medicament container 17262 includes a first plunger 17284 and a second plunger 17282. As described above, when the medical device 17002 is in its initial configuration, the first plunger 17284 and the second plunger 17282 are arranged within the medicament container to define a first medicament containing portion 17283 and a second medicament containing portion 17285. As described above, in some embodiments, the first medicament containing portion 17283 can include a liquid medicament 17268 and the second medicament containing portion 17285 can include a solid medicament 17269 (e.g., a lyophilized powder).

The energy storage member 17412 is operatively coupled to the first plunger 17284 by a first movable member 17312. Similarly, the energy storage member 17412 is operatively coupled to the second plunger 17282 by a second movable member 17360. A switch 17413 is operatively disposed between the first movable member 17312, the second movable member 14360 and the energy storage member 17412. In use, the switch, which can be a valve, a mechanical linkage, an electronic switch or the like, selectively transmits the force produced by the energy storage member 17412 to the first movable member 17312 and the second movable member 14360. In this manner, the first plunger 17284 and the second plunger 17282 can be moved independently from each other by the energy storage member 17412.

For example, in some embodiments, the second plunger 17282 can be moved proximally within the medicament container 17262 to mix the first medicament 16268 and the second medicament 16269. When the second movable member 17360 reaches a predetermined point, the second movable member 17360 can actuate the switch 17413, thereby operatively disconnecting the energy storage member 17412 from the second movable member 17360 and operatively coupling the energy storage member 17412 to the first movable member 17312. As described above, this arrangement ensures that the mixing operation and the injection operations are distinct from each other.

While various embodiments of the invention have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Although various embodiments have been described as having particular features and/or combinations of components, other embodiments are possible having a combination of any features and/or components from any of embodiments where appropriate. For example, in some embodiments, an auto-injector can include multiple medicament selectors and a medicament mixer. In this manner, a user can first select the type and/or amount of a first medicament and the type and/or amount of a second medicament to be mixed to produce an injectable medicament.

Certain components of the auto-injector 14002 are shown and described as being coupled together via protrusions and mating recesses. The protrusions and/or recesses can be disposed on any of the components to be coupled together and need not be limited to only a certain component. For example, the actuation safety lock 14710 is shown as defining two openings 14719 that receive corresponding protrusions 14766 extending from the distal end portion 14764 of the mixing safety lock 14760. In some embodiments, however, the protrusions can be disposed on the actuation safety lock and the mating openings can be defined by the mixing safety lock. In other embodiments, two or more components can be coupled together in any suitable way, which need not include protrusions and mating recesses. For example, in some embodiments, two or more components can be coupled together via mating shoulders, clips, adhesive and the like.

Similarly, although certain components of the auto-injector 14002 are shown and described as being constructed from multiple separate components, in some embodiments, such components can be monolithically constructed. For example, the proximal cover 14162 is shown and described as including a spring clip 14362 and a mixing actuator safety lock 14760 that are constructed separately and then coupled together. In other embodiments, a spring clip and a mixing actuator safety lock can be constructed monolithically.

Although the second plunger 14282 is shown and described as being coupled to the medicament mixer 14360 by a plunger coupling 14392 that is disposed within the second plunger 14282, in other embodiments the second plunger 14282 can be coupled to the medicament mixer 14360 by any suitable means. For example, in some embodiments, a second plunger can be coupled to a medicament mixer by an adhesive. In other embodiments, a second plunger can be pivotably coupled to a medicament mixer by a ball and socket joint. In yet other embodiments, a second plunger can be coupled to a medicament mixer by a plunger coupling that engages the distal surface of the second plunger.

Although the medicament containers shown and described above include two plunger and two medicament containing portions, in some embodiments, a medicament container can include more than two plungers and/or more than two medicament containing portions. For example, in some embodiments a medicament container can include a first medicament containing portion configured to contain a first medicament, a second medicament containing portion configured to store contain a second medicament and mixing portion configured to receive and mix the first medicament and the second medicament when the mixing actuator is actuated.

Although the rod 14540 is shown and described as being an elongated member that is released by being elastically deformed, in some embodiments, a rod can be of any suitable shape and in any suitable orientation within the housing. Moreover, in some embodiments, a rod can be released by being plastically deformed. For example, in some embodiments, a rod can be disposed along an axis that is offset from the longitudinal axis of the energy storage member. In some embodiments, the rod can be configured to break upon actuation.

Although the spring clip 14362 is shown and described above as being deformable to decouple the medicament mixer 14360 from mixing spring 14436 after the auto-injector 14002 is in the second configuration (FIG. 34), in other embodiments, the medicament mixer 14360 can be decoupled from the mixing spring 14436 in any suitable manner. For example, in some embodiments, the medicament mixer 14360 can be coupled to the mixing spring 14436 by a frangible clip configured to break when the auto-injector is in the second configuration.

Although the auto-injector 14002 is shown and described above without reference to a needle guard, in other embodiments an auto-injector can include any suitable needle guard. For example, in some embodiments, an auto-injector can include a rigid needle guard. In other embodiments, an auto-injector can include a flexible needle guard. In other embodiments, an auto-injector can include a needle guard that also functions as a mixing actuator safety cover (e.g., removal of the needle guard also enables the mixing actuator). Such needle guards can be made of any suitable material, such as, for example, polypropylene, rubber or any other elastomer.

Although the auto-injector 14002 is shown and described as including a puncturing element 14620 to puncture a portion of the compressed gas container 14412, in other embodiments any suitable gas release mechanism can be used. For example, in some embodiments, a gas release mechanism can include an actuator configured to actuate a valve that controls the flow of gas out of the compressed gas container. In some embodiments, a compressed gas container can include a spring loaded check ball and the gas release mechanism can include an actuator configured to engage and depress the check ball to release pressurized gas from the compressed gas container.

Although the auto-injector 14002 is shown and described as including a compressed gas cylinder 14412, in other embodiments an auto-injector can include any suitable energy storage member. For example, in some embodiments, an auto-injector can include a mechanical energy storage member, such as a spring, an electrical energy storage member, such as a battery or a capacitor, a chemical energy storage member, such as a container containing two substances that can react to produce energy, a magnetic energy storage member or the like. Similarly, although the auto-injector 14002 is shown and described as including a mixing spring 14436, in other embodiments an auto-injector can include any suitable energy storage member to move the medicament mixer.

Although the auto-injector 14002 has been shown and described having a housing 14110 having a substantially rectangular shape, in some embodiments, an auto-injector can have a housing having any shape. In some embodiments, for example, an auto-injector can have a substantially cylindrical shape. In other embodiments, for example, the auto-injector can have an irregular and/or asymmetrical shape.

Figures 44, 45:
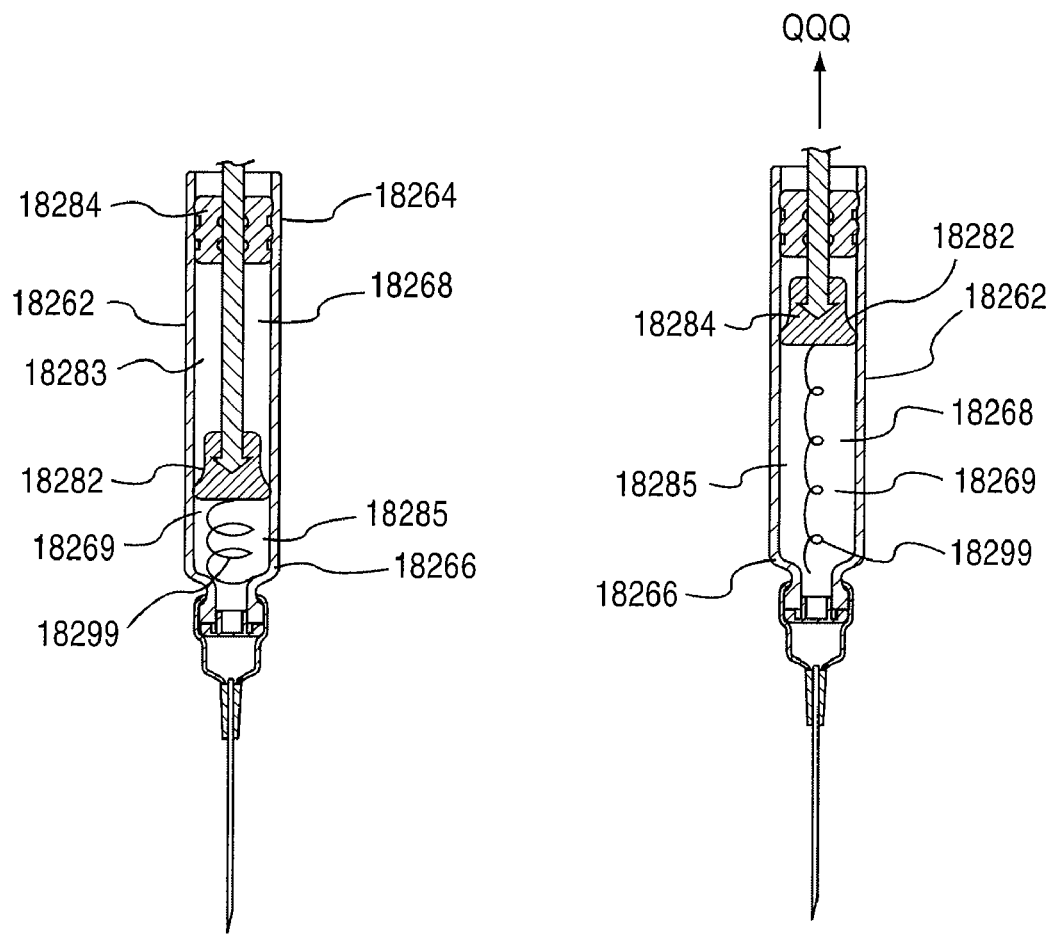
FIGS. 44 and 45 are cross-sectional front views of a portion of a medical device according to an embodiment of the invention in a first configuration and second configuration, respectively.

Although the auto-injectors are shown and described above as including a mixing plunger that moves within a medicament container to combine and/or mix a first medicament and a second medicament, in some embodiments, the user can shake the auto-injector to enhance the mixing process. In other embodiments, an auto-injector can include an agitator to enhance the mixing process. For example, FIGS. 44 and 45 show a medicament container 18262 according to an embodiment of the invention in a first configuration and a second configuration, respectively. The medicament container 18262 includes a proximal end portion 18264 and a distal end portion 18266. The medicament container 18262 includes a first plunger 18284, a second plunger 18282 and an agitator 18299.

The second plunger 18282 is disposed distally from the first plunger 18284. The first plunger 18284 and the second plunger 18282 are each movably disposed within the medicament container 18262. The agitator, which can be, for example, a flexible wire, an elastic member or the like, is coupled to the second plunger 18282.

As shown in FIG. 44, when the medical device 18002 is in the first configuration, the first plunger 18284 is disposed in a first position within the medicament container 18262. The second plunger 18282 is disposed in a second position within the medicament container 18262. The second position is spaced apart from the first position such that a first medicament containing portion 18283 is defined between the first plunger 18284 and the second plunger 18282. Similarly, a second medicament containing portion 18285 is defined between the second plunger 18282 and the distal end portion 18266 of the medicament container 18262.

As described above, when the second plunger 18282 moves within the medicament container 18262, the first medicament containing portion 18283 is placed in fluid communication with the second medicament containing portion 18285. Accordingly, when the second plunger 18282 moves, the contents of the first medicament containing portion 18283 can be mixed with the contents of the second medicament containing portion 18285.

When the medicament container 18262 moves from the first configuration (FIG. 44) to the second configuration (FIG. 45), the agitator moves from its retracted position to an expanded position. In this manner, the agitator can enhance the mixing of the medicaments contained in the medicament container 18262.

Although the agitator 18299 is described as a flexible member, in other embodiments, an agitator can include any suitable mechanism for enhancing the mixing of medicaments within the medicament container. For example, in some embodiments, an agitator can include angled flow passages within the second plunger to produce a swirl effect when the first medicament containing portion is placed in fluid communication with the second medicament containing portion. In other embodiments, fluid communication between the first medicament containing portion and the second medicament containing portion can be established by a channel within a side wall of the medicament container. In such embodiments, the channel can be a spiral channel to produce a turbulent flow to enhance the mixing of medicaments within the medicament container.

Although the auto-injector 14002 is shown and described as mixing the medicaments contained therein at a substantially constant volume, which can allow the first medicament containing portion 14283 and/or the second medicament containing portion 14285 to be devoid of a gas, in other embodiments, the first medicament containing portion 14283 and/or the second medicament containing portion 14285 can contain a gas (e.g., air). In such embodiments, an auto-injector can include an air purge valve to purge the air contained within the medicament after the medicament is mixed, but before the medicament is injected. Such an air purge valve can be operatively coupled to the actuation safety lock and/or the medicament mixer.

Although the auto-injector 14002 is shown and described as being devoid of an electronic circuit system, in other embodiments, an auto-injector can include an electronic circuit system configured to output an electronic output. Such an electronic circuit system can be an electronic circuit system of the types shown and described in U.S. patent application Ser. No. 11/671,025, entitled "Devices, Systems and Methods for Medicament Delivery," filed Feb. 5, 2007, which is incorporated herein by reference in its entirety. For example, in some embodiments, an auto-injector can include a electronic circuit system configured to sense the status of the medicaments contained therein (e.g., unmixed, partially mixed, fully mixed, or the like) and output an electronic output in response to such status. In other embodiments, an auto-injector can include an electronic circuit system configured to output an instruction associated with the mixing operation as described herein.

Although the medical device are shown and described above as being medicament delivery device including a medicament and/or a needle, in other embodiments, a medical device can be a simulated medicament delivery device. In some embodiments, for example, a simulated auto-injector can correspond to an actual auto-injector (e.g., auto-injector 14002) and can be used, for example, to train a user in the operation of the corresponding actual auto-injector.

In some embodiments, a simulated auto-injector can be devoid of a medicament and/or those components that cause the medicament to be delivered (e.g., a needle). In this manner, the simulated auto-injector can be used to train a user in the use of the actual medicament delivery device without exposing the user to a needle and/or a medicament. Moreover, the simulated auto-injector can have features to identify it as a training device to prevent a user from mistakenly believing that the simulated auto-injector can be used to deliver a medicament. Examples of such simulated auto-injectors are described in U.S. patent application Ser. No. 11/679,331, entitled "Medical Injector Simulation Device," filed Feb. 27, 2007, which is incorporated herein by reference in its entirety.

What is claimed is:

1. An apparatus, comprising:
   a housing;
   a medicament container disposed within the housing, the medicament container having a first plunger disposed within a proximal end portion of the medicament container and a second plunger disposed within the medicament container spaced apart from the first plunger, the first plunger, a portion of the medicament container and the second plunger collectively defining, at least in part, a first medicament containing portion containing a liquid medicament, the second plunger and a distal end portion of the medicament container collectively defining, at least in part, a second medicament containing portion containing a substantially dry medicament;
   a first energy storage member configured to produce a force when actuated to move at least the second plunger within the medicament container, the first medicament containing portion being placed in fluid communication with the second medicament containing portion when the second plunger is moved in response to the first energy storage member being actuated, the first energy storage member being any one of a spring or a compressed gas container; and
   a second energy storage member configured to produce a force when actuated to move the first plunger and the second plunger within the medicament container, the second energy storage member different than the first energy storage member, the second energy storage member being any one of a spring or a compressed gas container.

2. The apparatus of claim 1, wherein the second energy storage member is configured to be actuated independently from the first energy storage member.

3. The apparatus of claim 1, wherein:
the second medicament containing portion being placed in fluid communication with a needle when the first plunger and second plunger are moved in response to the second energy storage member being actuated.

4. The apparatus of claim 1, further comprising:
a first movable member operatively coupled to the first energy storage member such that the force produced by the first energy storage member acts on the first movable member to move at least the second plunger within the medicament container; and
a second movable member operatively coupled to the second energy storage member such that the force produced by the second energy storage member acts on the second movable member to move the first plunger and the second plunger within the medicament container,
a portion of the first movable member disposed within the second movable member.

5. The apparatus of claim 1, wherein:
the first energy storage member is a first spring configured to be actuated by a first actuator; and
the second energy storage member is second spring configured to be actuated by a second actuator, different than the first actuator.

6. The apparatus of claim 1, wherein the first energy storage member is configured to be actuated by an actuator movably coupled to the housing, the apparatus further comprising:
a cover configured to be disposed about at least a portion of the housing such that the actuator is obstructed by the cover.

7. The apparatus of claim 1, wherein a longitudinal axis of the second energy storage member is offset from a longitudinal axis of the medicament container.

8. The apparatus of claim 1, wherein:
substantially dry medicament includes a glucagon formulation.

9. The apparatus of claim 1, wherein the second energy storage member is further configured to move the medicament container in a first direction within the housing, the apparatus further comprising:
a coil spring configured to produce a force to move the medicament container in a second direction opposite the first direction.

10. An apparatus, comprising:
a housing;
a medicament container disposed within the housing, the medicament container including a first plunger and a second plunger, the first plunger, a portion of the medicament container and the second plunger collectively defining, at least in part, a first volume containing a first substance, the second plunger and a distal end portion of the medicament container collectively defining, at least in part, a second volume containing a second substance;
a mixing assembly including a mixing member and a first spring, the mixing assembly configured to place the first volume in fluid communication with the second volume when the mixing assembly is moved from a first mixing configuration to a second mixing configuration, the first spring configured to produce a mixing force acting on the mixing member to move the mixing assembly from the first mixing configuration to the second mixing configuration when the mixing assembly is actuated; and
an injection assembly including an injection member and a second spring, the injection assembly configured to move the first plunger within the medicament container to expel a mixture of the first substance and the second substance when the injection assembly is moved from a first injection configuration to a second injection configuration, the second spring configured to produce an injection force acting on the injection member to move the injection assembly from the first injection configuration to the second injection configuration when the injection assembly is actuated.

11. The apparatus of claim 10, wherein:
the mixing assembly is configured to move at least the second plunger within the medicament container to place the first volume in fluid communication with the second volume; and
the injection assembly configured to move the first plunger and the second plunger within the medicament container.

12. The apparatus of claim 10, further comprising:
a needle coupled to the medicament container,
the injection assembly configured to move the medicament container within the housing from a first position to a second position, the needle disposed within the housing when the medicament container is in the first position, at least a distal end portion of the needle disposed outside of the housing when the medicament container is in the second position.

13. The apparatus of claim 10, wherein:
the mixing member is configured to move the second plunger when the mixing assembly is actuated; and
the injection member is configured to move the first plunger and the second plunger within the medicament container, a portion of the mixing member disposed within the injection member.

14. The apparatus of claim 10, wherein a longitudinal axis of the second spring is offset from a longitudinal axis of the medicament container.

15. The apparatus of claim 10, wherein:
the mixing assembly is configured to be actuated by a first actuator; and
the injection assembly is configured to be actuated by a second actuator, different than the first actuator.

16. The apparatus of claim 10, wherein the mixing assembly is configured to be actuated by an actuator movably coupled to the housing, the apparatus further comprising:
a cover configured to be movably disposed about at least a portion of the housing such that the actuator is obstructed by the cover.

17. The apparatus of claim 10, wherein the first substance is a liquid and the second substance is a substantially dry glucagon formulation.

18. The apparatus of claim 10, further comprising:
a needle coupled to the medicament container, the injection assembly configured to move the medicament container within the housing from a first position to a second position, the needle disposed within the housing when the medicament container is in the first position, at least a distal end portion of the needle disposed outside of the housing when the medicament container is in the second position; and
a retraction spring configured to produce a force to move the medicament container from the second position back towards the first position.

19. An apparatus, comprising:
a housing;
a medicament container disposed within the housing, the medicament container including a first plunger and a second plunger, the first plunger, a portion of the medicament container and the second plunger collectively defining, at least in part, a first volume, the second plunger and a distal end portion of the medicament container collectively defining, at least in part, a second volume;
a mixing member having a portion in contact with the first plunger, the mixing member configured to move, at least partially within the medicament container, from a first position to a second position to move at least the second plunger within the medicament container;
a first spring configured to produce a first force to move the mixing member;
an injection member configured to move the first plunger and the second plunger within the medicament container; and
a second spring configured to produce a second force to move the injection member,
the mixing member configured to move relative to the injection member when moved from its first position to its second position.

20. The apparatus of claim 19, wherein:
the portion of the mixing member is a first portion; and
a second portion of the mixing member is slidably disposed within the injection member.

21. The apparatus of claim 19, further comprising:
a mixing actuator assembly configured to initiate movement of the mixing member, the mixing actuator assembly including a release member movably disposed within the housing, a longitudinal axis of the release member being offset from a longitudinal axis of the medicament container.

22. The apparatus of claim 19, further comprising:
an injection actuator assembly configured to initiate movement of the injection member, the injection actuator assembly including a release member movably disposed within the housing, a longitudinal axis of the release member being offset from a longitudinal axis of the medicament container.

23. The apparatus of claim 19, further comprising:
an actuator member disposed at least partially outside of the housing, the actuator member configured to initiate movement of the mixing member when the actuator member is manipulated by a user; and
a cover configured to be movably disposed about at least a portion of the housing such that the actuator member is obstructed by the cover.

24. The apparatus of claim 19, wherein:
a longitudinal axis of the first spring is offset from a longitudinal axis of the second spring.

25. The apparatus of claim 19, wherein:
the first volume contains a liquid;
the second volume contains a substantially dry glucagon formulation; and
the first volume is placed in fluid communication with the second volume when the second plunger is moved within the medicament container in response to the mixing member moving from its first position to its second position.

26. An apparatus, comprising:
a housing;
a medicament container disposed within the housing, the medicament container including a first plunger and a second plunger, the first plunger, a portion of the medicament container and the second plunger collectively defining, at least in part, a first volume, the second plunger and a distal end portion of the medicament container collectively defining, at least in part, a second volume;
a mixing member having a portion configured to move within the medicament container from a first position to a second position to move the second plunger within the medicament container;
a first spring configured to produce a first force to move the mixing member;
an injection member configured to move the first plunger and the second plunger within the medicament container; and
a second springy, configured to produce a second force to move the injection member,
the portion the mixing member being slidably disposed within the injection member.

27. The apparatus of claim 26, wherein the mixing member is configured to be actuated independently from the injection member.

28. The apparatus of claim 26, further comprising:
a mixing actuator assembly configured to initiate movement of the mixing member, the mixing actuator assembly including a release member movably disposed within the housing, a longitudinal axis of the release member being offset from a longitudinal axis of the medicament container.

29. The apparatus of claim 26, further comprising:
an injection actuator assembly configured to initiate movement of the injection member, the injection actuator assembly including a release member movably disposed within the housing, a longitudinal axis of the release member being offset from a longitudinal axis of the medicament container.

30. The apparatus of claim 26, further comprising:
an actuator member disposed at least partially outside of the housing, the actuator member configured to initiate movement of the mixing member when the actuator member is manipulated by a user; and
a cover configured to be movably disposed about at least a portion of the housing such that the actuator member is obstructed by the cover.

* * * * *

UNITED STATES PATENT AND TRADEMARK OFFICE
CERTIFICATE OF CORRECTION

PATENT NO. : 8,123,719 B2
APPLICATION NO. : 11/692359
DATED : February 28, 2012
INVENTOR(S) : Eric S. Edwards et al.

It is certified that error appears in the above-identified patent and that said Letters Patent is hereby corrected as shown below:

In the Claims:

Column 33, line 36 (Claim 8), before "substantially" insert -- the --;
Column 36, line 23 (Claim 26), change "springy" to -- spring --.

Signed and Sealed this
Eighth Day of October, 2013

Teresa Stanek Rea
*Deputy Director of the United States Patent and Trademark Office*